(12) United States Patent
DeHennis et al.

(10) Patent No.: US 12,369,824 B2
(45) Date of Patent: Jul. 29, 2025

(54) DETECTING AND CORRECTING FOR INTERFERENCE IN AN ANALYTE MONITORING SYSTEM

(71) Applicant: Senseonics, Incorporated, Germantown, MD (US)

(72) Inventors: Andrew DeHennis, Germantown, MD (US); Mark Mortellaro, Germantown, MD (US); Abhi Chavan, Germantown, MD (US); Venkata Velvadapu, Germantown, MD (US); Philip Huffstetler, Germantown, MD (US); James Masciotti, Germantown, MD (US); Patricia Sanchez, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 666 days.

(21) Appl. No.: 17/825,137

(22) Filed: May 26, 2022

(65) Prior Publication Data
US 2022/0287597 A1 Sep. 15, 2022

Related U.S. Application Data

(63) Continuation-in-part of application No. 17/092,830, filed on Nov. 9, 2020, now Pat. No. 11,517,230,
(Continued)

(51) Int. Cl.
*A61B 5/1495* (2006.01)
*A61B 5/00* (2006.01)
(Continued)

(52) U.S. Cl.
CPC .......... *A61B 5/1495* (2013.01); *A61B 5/0031* (2013.01); *A61B 5/076* (2013.01);
(Continued)

(58) Field of Classification Search
CPC . A61B 5/1455; A61B 5/14556; A61B 5/1495; A61B 5/14532; A61B 5/1459;
(Continued)

(56) References Cited

U.S. PATENT DOCUMENTS 6,002,954 A    12/1999   Van Antwerp et al.
6,216,022 B1 *   4/2001   Tyrrell ................ A61B 5/1459
                                                               600/316
(Continued)

FOREIGN PATENT DOCUMENTS

EP            2779900 B1    9/2015
JP          2013/059483 A    4/2013
(Continued)

OTHER PUBLICATIONS

Mortellaro, Mark et al., "Performance characterization of an abiotic and fluorescent-based continuous glucose monitoring system in patients with type 1 diabetes," Biosensors and Bioelectronics, vol. 61, pp. 227-231 (2014).
(Continued)

*Primary Examiner* — Eric F Winakur
(74) *Attorney, Agent, or Firm* — Rothwell, Figg, Ernst & Manbeck, P.C.

(57) ABSTRACT

A sensor, system, and method for detecting and correcting for an effect on an analyte indicator of an analyte sensor. The analyte indicator may be configured to exhibit a first detectable property that varies in accordance with an analyte concentration and an effect on (e.g., degradation of) the analyte indicator. The analyte sensor may also include an interferent indicator configured to exhibit a second detectable property (e.g., absorption) that varies in accordance the effect on the analyte indicator. The analyte sensor may generate (i) an analyte measurement based on the first detectable property exhibited by the analyte indicator and
(Continued)

(ii) an interferent measurement based on the second detectable property exhibited by the interferent indicator. The analyte sensor may be part of a system that also includes a transceiver. The transceiver may use the analyte and interferent measurements to calculate an analyte level.

40 Claims, 27 Drawing Sheets

Related U.S. Application Data which is a continuation of application No. 15/957,604, filed on Apr. 19, 2018, now Pat. No. 10,827,962.

(60) Provisional application No. 63/193,784, filed on May 27, 2021, provisional application No. 62/487,289, filed on Apr. 19, 2017.

(51) Int. Cl.
*A61B 5/07* (2006.01)
*A61B 5/145* (2006.01)
*A61B 5/1455* (2006.01)
*A61B 5/1459* (2006.01)
*A61B 5/1473* (2006.01)

(52) U.S. Cl.
CPC ...... *A61B 5/14532* (2013.01); *A61B 5/14556* (2013.01); *A61B 5/1459* (2013.01); *A61B 5/14546* (2013.01); *A61B 5/1473* (2013.01); *A61B 2560/0219* (2013.01); *A61B 2560/0266* (2013.01)

(58) Field of Classification Search
CPC . A61B 5/14546; A61B 5/6846; A61B 5/6861; A61B 5/7271; A61B 5/0031
See application file for complete search history.

(56) References Cited

U.S. PATENT DOCUMENTS

| | | |
|---|---|---|
| 6,330,464 B1 | 12/2001 | Colvin, Jr. et al. |
| 7,060,503 B2 | 6/2006 | Colvin, Jr. |
| 8,073,548 B2 | 12/2011 | Colvin, Jr. et al. |
| 8,143,068 B2 | 3/2012 | Colvin, Jr. et al. |
| 8,320,983 B2 * | 11/2012 | Martini ............... A61B 5/1459 600/316 |
| 9,414,775 B2 | 8/2016 | Colvin, Jr. et al. |
| 9,427,181 B2 | 8/2016 | Emken et al. |
| 9,427,182 B2 | 8/2016 | Emken et al. |
| 9,611,504 B2 | 4/2017 | Petrich et al. |
| 9,693,714 B2 | 7/2017 | DeHennis et al. |
| 9,778,190 B2 | 10/2017 | Huffstetler et al. |
| 10,827,962 B2 | 11/2020 | DeHennis et al. |
| 2008/0188725 A1 | 8/2008 | Markle et al. |
| 2011/0081727 A1 | 4/2011 | Colvin, Jr. et al. |
| 2012/0238842 A1 | 9/2012 | Colvin, Jr. et al. |
| 2012/0265035 A1 | 10/2012 | Bohm et al. |
| 2013/0241745 A1 | 9/2013 | Colvin, Jr. et al. |
| 2014/0018644 A1 | 1/2014 | Colvin, Jr. et al. |
| 2014/0088383 A1 | 3/2014 | Colvin, Jr. et al. |
| 2014/0128694 A1 | 5/2014 | Gallant et al. |
| 2016/0312033 A1 | 10/2016 | Yang et al. |
| 2017/0049371 A1 | 2/2017 | Emken et al. |
| 2021/0052202 A1 | 2/2021 | DeHennis et al. |
| 2021/0137420 A1 | 5/2021 | Masciotti et al. |

FOREIGN PATENT DOCUMENTS

| | | |
|---|---|---|
| WO | 03/010510 A2 | 2/2003 |
| WO | 2016/154034 A1 | 9/2016 |
| WO | 2017/105927 A1 | 6/2017 |

OTHER PUBLICATIONS

Bryan C Dickinson et al., "Preparation and use of MitoPY1 for imaging hydrogen peroxide in mitochondria of live cells," Nat Protoc. Jun. 2013 ; 8(6): 1249-1259. doi:10.1038/nprot.2013.064.

* cited by examiner

DETECTING AND CORRECTING FOR INTERFERENCE IN AN ANALYTE MONITORING SYSTEM

CROSS-REFERENCE TO RELATED APPLICATION

The present application claims the benefit of priority to U.S. Provisional Application Ser. No. 63/193,784, filed on May 27, 2021, which is incorporated herein by reference in its entirety. In addition, this application is a continuation-in-part of U.S. application Ser. No. 17/092,830, filed on Nov. 9, 2020, which is a continuation of U.S. application Ser. No. 15/957,604, filed on Apr. 19, 2018, now U.S. Pat. No. 10,827,962, issued on Nov. 10, 2020, which claims the benefit of priority to U.S. Provisional Application Ser. No. 62/487,289, filed on Apr. 19, 2017, all of which are incorporated herein by reference in their entireties.

BACKGROUND

Field of Invention

The present invention relates generally to detecting and correcting for interference in an analyte monitoring system. The interference may include blood in a medium (e.g., interstitial fluid) and/or an effect (e.g., oxidation-induced degradation) on an analyte indicator in the analyte monitoring system.

Discussion of the Background

Analyte monitoring systems may be used to monitor analyte levels, such as analyte concentrations (e.g., glucose concentrations). One type of analyte monitoring system is a continuous analyte monitoring system. A continuous analyte monitoring system measures analyte levels throughout the day and can be very useful in the management of diseases, such as diabetes.

Some analyte monitoring systems include an analyte sensor, which may be implanted (fully or partially) in an animal and may include an analyte indicator. Blood in interstitial fluid in proximity to the analyte indicator and/or an effect on the analyte indicator may interfere with the accurate measurement of the analyte (e.g., glucose) by the analyte sensor. For example, the analyte sensor may lose sensitivity while implanted in the animal as a result of changes in sensitivity parameters (e.g., calibration constants). The changes in sensitivity parameters may be due to, for example, degradation of the analyte indicator. The degradation may be caused by, for example, oxidation of the analyte indicator induced by cellular generated reactive oxygen species (ROS). See, e.g., U.S. Pat. Nos. 8,143,068, 9,427,181, and U.S. Patent Application Publication No. 2012/0238842, each of which are incorporated by reference herein in their entireties. The rate in vivo sensitivity loss can be reduced by, for example, using oxidation resistant indicator molecules, integrating catalytic protection, and/or using a membrane that catalyzes degradation of reactive oxygen species (ROS). However, the reducing the rate of in vivo sensitivity loss does not completely prevent sensitivity loss. The gradual change in sensitivity parameters over time may negatively affect analyte sensing accuracy and may necessitate re-calibrations using reference analyte measurements (e.g., self-monitoring blood glucose measurements), which may be uncomfortable and/or otherwise undesirable for a user.

SUMMARY

The present invention overcomes the disadvantages of prior systems by providing an analyte monitoring system capable of detecting and correcting for one or more interferents. In some aspects, the one or more interferents may interfere with the accurate measurement of an analyte (e.g., glucose) in a medium (e.g., interstitial fluid). In some aspects, the one or more interferents may include blood in the medium. In some aspects, the one or more interferents may include an effect on an analyte indicator of the analyte sensor. In contrast with prior art systems that can only correct for one or more interferents at the time of a re-calibration that uses a reference analyte measurement, the analyte monitoring system may provide, among other advantages, the ability to correct for one or more interferents without the need for a reference analyte measurement. In some aspects, the analyte monitoring system may include an analyte sensor that measures the one or more interferents using an interferent indicator. In some aspects, the interferent indicator not be sensitive to the analyte. In some aspects, the interferent indicator may have one or more properties that vary with the effect (e.g., degradation by reactive oxygen species (ROS)) on the analyte indicator. In some aspects, the one or more properties of the interferent indicator may include an absorption that varies in accordance with the effect on the analyte indicator. In some aspects, the one or more properties of the interferent indicator may include optical properties that vary in accordance with the effect on the analyte indicator. In some aspects, the interferent indicator may be used as a reference dye for measuring and correcting for the effect on the analyte indicator. In some aspects, the analyte monitoring system may correct for the one or more interferents using an empiric correlation established through laboratory testing.

One aspect of the invention may provide an analyte sensor for measurement of an analyte in a medium within a living animal. The analyte sensor may include an analyte indicator, a degradation indicator, and sensor elements. The analyte indicator may be configured to exhibit a first detectable property that varies in accordance with (i) an amount or concentration of the analyte in the medium and (ii) an extent to which the analyte indicator has degraded. The degradation indicator may be configured to exhibit a second detectable property that varies in accordance with an extent to which the degradation indicator has degraded. The extent to which the degradation indicator has degraded may correspond to the extent to which the analyte indicator has degraded. The sensor elements may be configured to generate (i) an analyte measurement based on the first detectable property exhibited by the analyte indicator and (ii) a degradation measurement based on the second detectable property exhibited by the degradation indicator.

In some aspects, the extent to which the degradation indicator has degraded may be proportional to the extent to which the analyte indicator has degraded. In some aspects, degradation to the analyte indicator may include reactive oxidation species (ROS)-induced oxidation, and degradation to the degradation indicator includes ROS-induced oxidation. In some aspects, the analyte indicator may be a phenylboronic-based analyte indicator. In some aspects, the degradation indicator may be a phenylboronic-based degradation indicator.

In some aspects, the analyte sensor may further include an indicator element comprising the analyte indicator and the degradation indicator. In some aspects, the analyte indicator may include analyte indicator molecules distributed throughout the indicator element, and the degradation indicator may include degradation indicator molecules distributed throughout the indicator element. In some aspects, the second detectable property does not vary in accordance with the amount or concentration of the analyte in the medium.

In some aspects, the sensor elements may include a first light source and a first photodetector. The first light source may be configured to emit first excitation light to the analyte indicator. The first photodetector configured to receive first emission light emitted by the analyte indicator and output the analyte measurement. The analyte measurement may be indicative of an amount of first emission light received by the first photodetector. In some aspects, the sensor elements may include a second light source and a second photodetector. The second light source may be configured to emit second excitation light to the degradation indicator. The second photodetector may be configured to receive second emission light emitted by the degradation indicator and output the degradation measurement. The degradation measurement may be indicative of an amount of second emission light received by the second photodetector. In some aspects, the first photodetector may be configured to receive second excitation light reflected from the indicator element and output a first reference signal indicative of an amount of reflected second excitation light received by the first photodetector. In some aspects, the sensor elements may include a third photodetector configured to receive first excitation light reflected from the indicator element and output a second reference signal indicative of an amount of reflected first excitation light received by the third photodetector.

Another aspect of the invention may provide a method including using an analyte indicator of an analyte sensor to measure an amount or concentration of an analyte in a medium. The method may include using a degradation indicator of the analyte sensor to measure an extent to which the degradation indicator has degraded. The method may include using a sensor interface device of a transceiver to receive from the analyte sensor an analyte measurement indicative of the amount or concentration of the analyte in the medium. The method may include using the sensor interface device of the transceiver to receive from the analyte sensor a degradation measurement indicative of the extent to which the degradation indicator has degraded. The method may include using a controller of the transceiver to calculate an extent to which the analyte indicator of the analyte sensor has degraded based at least on the received degradation measurement. The method may include using the controller of the transceiver to adjust a conversion function based on the calculated extent to which the analyte indicator has degraded. The method may include using the controller of the transceiver to calculate an analyte level using the adjusted conversion function and the received analyte measurement. The method may include displaying the calculated analyte level.

Still another aspect of the invention may provide an analyte monitoring system including an analyte sensor and a transceiver. The analyte sensor may include an analyte indicator, a degradation indicator, sensor elements, and a transceiver interface device. The analyte indicator may be configured to exhibit a first detectable property that varies in accordance with (i) an amount or concentration of an analyte in a medium and (ii) an extent to which the analyte indicator has degraded. The degradation indicator may be configured to exhibit a second detectable property that varies in accordance with an extent to which the degradation indicator has degraded. The sensor elements may be configured to generate (i) an analyte measurement based on the first detectable property exhibited by the analyte indicator and (ii) a degradation measurement based on the second detectable property exhibited by the degradation indicator. The transceiver may include a sensor interface device and a controller. The controller may be configured to: (i) receive the analyte measurement from the analyte sensor via the transceiver interface device of the analyte sensor and the sensor interface device; (ii) receive the degradation measurement from the analyte sensor via the transceiver interface device of the analyte sensor and the sensor interface device; (iii) calculate an extent to which the analyte indicator of the analyte sensor has degraded based at least on the received degradation measurement; (iv) adjust a conversion function based on the calculated extent to which the analyte indicator has degraded; and (v) calculate an analyte level using the adjusted conversion function and the received analyte measurement.

In some aspects, the analyte sensor may further include an indicator element, and the indicator element may include the analyte indicator and the degradation indicator. In some aspects, the second detectable property does not vary in accordance with the amount or concentration of the analyte in the medium.

Yet another aspect of the invention may provide an analyte monitoring system including an analyte indicator, an interferent indicator, sensor elements, and a controller. The analyte indicator may have a first detectable property that varies in accordance with at least (i) an amount or concentration of an analyte in a medium and (ii) an effect on the analyte indicator. The interferent indicator may have an absorption that varies in accordance with the effect on the analyte indicator. The sensor elements may be configured to generate (i) an analyte measurement based on the first detectable property of the analyte indicator and (ii) a reference measurement based on at least the absorption of the interferent indicator. The controller may be configured to: (i) calculate the effect on the analyte indicator based at least on the reference measurement, (ii) adjust a conversion function based on at least the calculated effect on the analyte indicator, and (iii) calculate an analyte level using the adjusted conversion function and the analyte measurement.

In some aspects, the effect on the analyte indicator may be degradation of the analyte indicator. In some aspects, the system may further include an indicator element that comprises the analyte indicator and the interferent indicator, the analyte indicator may include analyte indicator molecules distributed throughout the indicator element, and the interferent indicator may include interferent indicator molecules distributed throughout the indicator element.

In some aspects, the sensor elements a first light source configured to emit first excitation light to the analyte indicator and a signal photodetector configured to receive first emission light emitted by the analyte indicator and output the analyte measurement, and the analyte measurement may be indicative of an amount of the first emission light received by the signal photodetector. In some aspects, the sensor elements may further include a second light source configured to emit second excitation light to the interferent indicator. In some aspects, the signal photodetector may be further configured to receive an amount of the second excitation light and output the reference measurement, the reference measurement may be indicative of the amount of the received second excitation light, and the amount of the received second excitation light may be indicative of the absorption of the interferent indicator. In some aspects, the sensor elements may further include a reference photodetector configured to receive an amount of the second excitation light and output the reference measurement, the reference measurement may be indicative of the amount of the received second excitation light, and the amount of the received second excitation light may be indicative of the absorption of the interferent indicator.

In some aspects, the sensor elements may further include an interferent photodetector configured to receive second emission light emitted by the interferent indicator and output an interferent measurement indicative of an amount of the second emission light received by the interferent photodetector. In some aspects, the second emission light may vary in accordance with the effect on the analyte indicator. In some aspects, the sensor elements may include a first reference photodetector configured to receive an amount of the first excitation light and output a first reference measurement indicative of the amount of the received first excitation light. In some aspects, the second emission light emitted by the interferent indicator does not vary in accordance with the amount or concentration of the analyte in the medium. In some aspects, the processor may be configured to calculate the effect on the analyte indicator based at least on the reference measurement and the interferent measurement. In some aspects, the processor may be configured to calculate the effect on the analyte indicator based at least on a ratio of the interferent measurement and the reference measurement.

In some aspects, the processor may be further configured to calculate an amount of blood in the medium. In some aspects, the processor may be configured to adjust the conversion function based on at least the calculated effect on the analyte indicator and the calculated amount of blood in the medium. In some aspects, the reference measurement may be a second reference measurement, and the sensor elements may include a first light source, a second light source, a first reference photodetector, and a signal photodetector. In some aspects, the first light source may be configured to emit first excitation light to the analyte indicator, the second light source may be configured to emit second excitation light to the interferent indicator, the first reference photodetector may be configured to receive an amount of the first excitation light and output a first reference measurement indicative of the amount of the received first excitation light, and the signal photodetector may be configured to (i) receive first emission light emitted by the analyte indicator and output the analyte measurement and (ii) receive an amount of the second excitation light and output the second reference measurement. In some aspects, the analyte measurement may be indicative of the amount of the received first emission light, and the second reference measurement may be indicative of the amount of the received second excitation light.

In some aspects, the reference measurement may be a second reference measurement, and the sensor elements include a first light source, a second light source, a first reference photodetector, and a signal photodetector. In some aspects, the first light source may be configured to emit first excitation light to the analyte indicator, the second light source may be configured to emit second excitation light to the interferent indicator, the first reference photodetector may be configured to receive an amount of the first excitation light and output a first reference measurement indicative of the amount of the received first excitation light, the signal photodetector may be configured to receive first emission light emitted by the analyte indicator and output the analyte measurement, the analyte measurement may be indicative of an amount of the received first emission light, the second reference photodetector may be configured to receive an amount of the second excitation light and output the second reference measurement, and the second reference measurement may be indicative of the amount of the received second excitation light.

In some aspects, the processor may be configured to calculate the amount of blood in the medium based on at least the first and second reference measurements. In some aspects, the processor may be configured to calculate the amount of blood in the medium based on at least a ratio of the first and second reference measurements. In some aspects, the sensor elements may include an interferent photodetector configured to receive emission light emitted by the interferent indicator and output an interferent measurement indicative of an amount of the emission light received by the interferent photodetector, and the processor may be configured to calculate the amount of blood in the medium based on at least the interferent measurement.

In some aspects, the interferent indicator may have a second detectable property that varies in accordance with the effect on the analyte indicator, the sensor elements may be further configured to generate an interferent measurement based on the second detectable property of the analyte indicator, and the processor may be configured to calculate the effect on the analyte indicator based at least on the reference measurement and the interferent measurement. In some aspects, the processor may be configured to calculate the effect on the analyte indicator at least based on a ratio of the interferent measurement and the reference measurement.

Still another aspect of the invention may provide a method including using an analyte indicator to generate an analyte measurement indicative of an amount or concentration of an analyte in a medium, and the analyte measurement may vary in accordance with at least an effect on the analyte indicator. The method may include using an interferent indicator to generate a reference measurement indicative of an absorption of the interferent indicator, and the absorption may vary in accordance with the effect on the analyte indicator. The method may include calculating the effect on the analyte indicator based at least on the reference measurement. The method may include adjusting a conversion function based on at least the calculated effect on the analyte indicator. The method may include calculating an analyte level using the adjusted conversion function and the analyte measurement.

In some aspects, the effect on the analyte indicator may be degradation of the analyte indicator.

In some aspects, using the analyte indicator to generate the analyte measurement may include emitting first excitation light to the analyte indicator and using a signal photodetector configured to receive first emission light emitted by the analyte indicator and output the analyte measurement, and the analyte measurement may be indicative of an amount of the first emission light received by the signal photodetector. In some aspects, using the interferent indicator to generate the reference measurement may include emitting second excitation light to the interferent indicator. In some aspects, using the interferent indicator to generate the reference measurement may further include using the signal photodetector to receive an amount of the second excitation light and output the reference measurement, the reference measurement may be indicative of the amount of the received second excitation light, and the amount of the received second excitation light may be indicative of the absorption of the interferent indicator. In some aspects, using the interferent indicator to generate the reference measurement may further include using a reference photodetector to receive an amount of the second excitation light and output the reference measurement, the reference measurement may be indicative of the amount of the received second excitation light, and the amount of the received second excitation light may be indicative of the absorption of the interferent indicator.

In some aspects, the method may further include using an interferent photodetector to receive second emission light emitted by the interferent indicator and output an interferent measurement indicative of an amount of the second emission light received by the interferent photodetector. In some aspects, the second emission light may vary in accordance with the effect on the analyte indicator. In some aspects, the method may further include using a first reference photodetector to receive an amount of the first excitation light and output a first reference measurement indicative of the amount of the received first excitation light. In some aspects, the effect on the analyte indicator may be calculated based at least on the reference measurement and the interferent measurement. In some aspects, the effect on the analyte indicator may be calculated based at least on a ratio of the interferent measurement and the reference measurement.

In some aspects, the method may further include calculating an amount of blood in the medium. In some aspects, the conversion function may be adjusted based on at least the calculated effect on the analyte indicator and the calculated amount of blood in the medium. In some aspects, the reference measurement may be a second reference measurement, and using the analyte indicator to generate the analyte measurement may include: emitting first excitation light to the analyte indicator, using a first reference photodetector to receive an amount of the first excitation light and output a first reference measurement indicative of the amount of the received first excitation light, and using a signal photodetector to receive first emission light emitted by the analyte indicator and output the analyte measurement. In some aspects, the analyte measurement may be indicative of the amount of the received first emission light. In some aspects, using the interferent indicator to generate the reference measurement may include: emitting second excitation light to the interferent indicator, and using the signal photodetector to receive an amount of the second excitation light and output the second reference measurement. In some aspects, the second reference measurement may be indicative of the amount of the received second excitation light, and the amount of blood in the medium may be calculated based on at least the first and second reference measurements.

In some aspects, the reference measurement may be a second reference measurement, and using the analyte indicator to generate the analyte measurement may include: emitting first excitation light to the analyte indicator, using a first reference photodetector to receive an amount of the first excitation light and output a first reference measurement indicative of the amount of the received first excitation light, and using a signal photodetector to receive first emission light emitted by the analyte indicator and output the analyte measurement. In some aspects, the analyte measurement may be indicative of the amount of the received first emission light. In some aspects, using the interferent indicator to generate the reference measurement may include: emitting second excitation light to the interferent indicator and using a second reference photodetector to receive an amount of the second excitation light and output the second reference measurement. In some aspects, the second reference measurement may be indicative of the amount of the received second excitation light. In some aspects, the amount of blood in the medium may be calculated based on at least the first and second reference measurements.

In some aspects, the amount of blood in the medium may be calculated based on at least a ratio of the first and second reference measurements. In some aspects, the method may further include using an interferent photodetector to receive emission light emitted by the interferent indicator and output an interferent measurement indicative of an amount of the emission light received by the interferent photodetector, and the amount of blood in the medium may be calculated based on at least the interferent measurement.

Yet another aspect of the invention may provide an analyte monitoring system. The system may include an indicator element including an analyte indicator and a degradation indicator. The analyte indicator may have a detectable property that varies in accordance with at least an amount or concentration of an analyte in a medium. The system may include a first light source configured to emit first excitation light to the analyte indicator. The system may include a second light source configured to emit second excitation light to the degradation indicator. The system may include one or more photodetectors configured to (i) receive emission light emitted by the analyte indicator and output an analyte measurement indicative of an amount of emission light received by the one or more photodetectors and (ii) receive second excitation light reflected from the indicator element and output a reference measurement indicative of an amount of reflected second excitation light received by the one or more photodetectors. The reference measurement is indicative of an opacity of the indicator element. The system may include a controller configured to: (i) adjust a conversion function based on the reference measurement and (ii) calculate an analyte level using the adjusted conversion function and the analyte measurement.

In some aspects, the one or more photodetectors may include a signal photodetector configured to (i) receive the first emission light and output the analyte measurement and (ii) receive the reflected second excitation light and output the reference measurement. In some aspects, the one or more photodetectors comprise (i) a signal photodetector configured to receive the first emission light and output the analyte measurement and (ii) a reference photodetector configured to receive the reflected second excitation light and output the reference measurement.

In some aspects, the emission light may be first emission light, the one or more photodetectors may be further configured to receive second emission light emitted by the degradation indicator and output a degradation measurement indicative of an amount of second emission light received by the one or more photodetectors, the controller may be further configured to calculate an extent to which the analyte indicator has degraded based at least on the degradation measurement, and the controller may be configured to adjust the conversion function based on the reference measurement and the calculated extent to which the analyte indicator has degraded.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting aspects of the present invention. In the drawings, like reference numbers indicate identical or functionally similar elements.

DETAILED DESCRIPTION OF PREFERRED EMBODIMENTS

Figure 1:
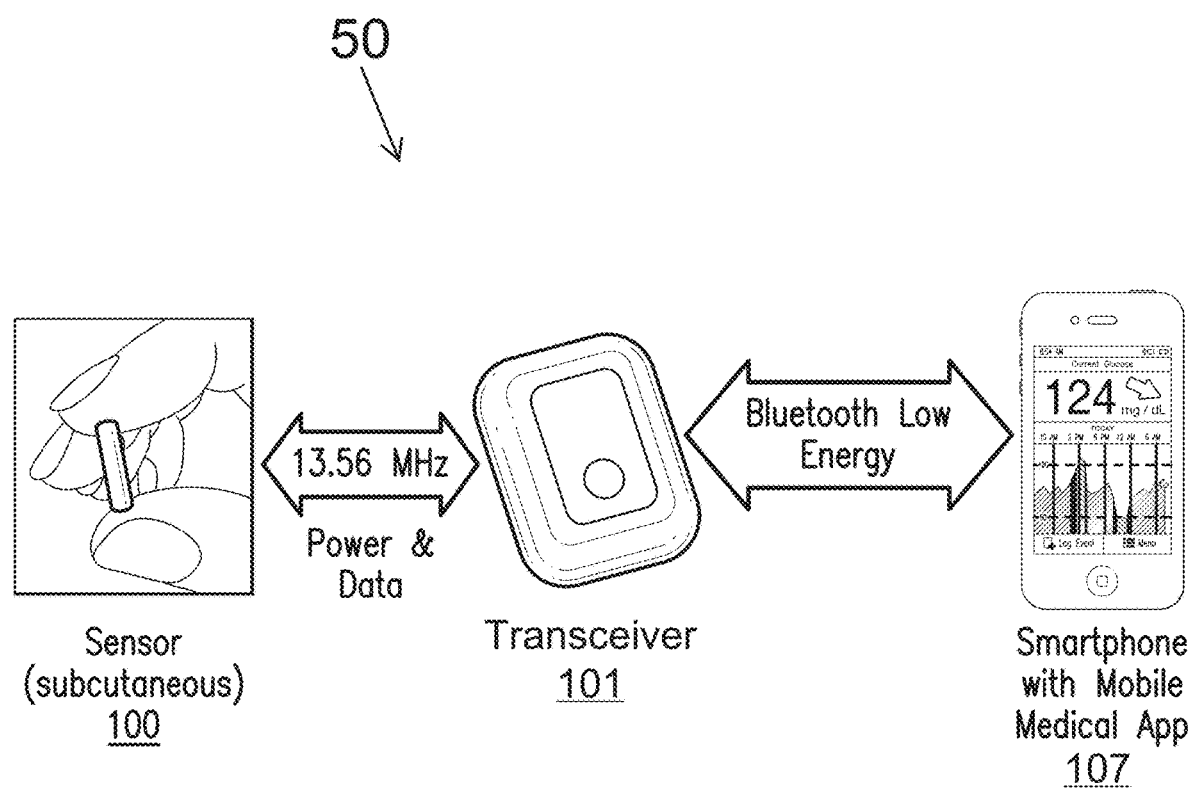
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some aspects, the analyte monitoring system 50 may include one or more of an analyte sensor 100, a transceiver 101, and a display device 107. In some aspects, the analyte sensor 100 may be a small, fully subcutaneously implantable sensor that measures the amount or concentration of an analyte (e.g., glucose) in a medium (e.g., interstitial fluid) of a living animal (e.g., a living human). However, this is not required, and, in some alternative aspects, the analyte sensor 100 may be a partially implantable (e.g., transcutaneous) sensor or a fully external sensor. In some aspects, the transceiver 101 may be an externally worn transceiver (e.g., attached via an armband, wristband, waistband, or adhesive patch). In some aspects, the transceiver 101 may remotely power and/or communicate with the sensor 100 to initiate and receive the measurements (e.g., via near field communication (NFC)). However, this is not required, and, in some alternative aspects, the transceiver 101 may power and/or communicate with the analyte sensor 100 via one or more wired connections. In some non-limiting aspects, the transceiver 101 may be a smartphone (e.g., an NFC-enabled smartphone). In some aspects, the transceiver 101 may communicate information (e.g., one or more analyte measurements) wirelessly (e.g., via a Bluetooth™ communication standard such as, for example and without limitation Bluetooth Low Energy) to a hand held application running on a display device 107 (e.g., smartphone).

Figure 2A:
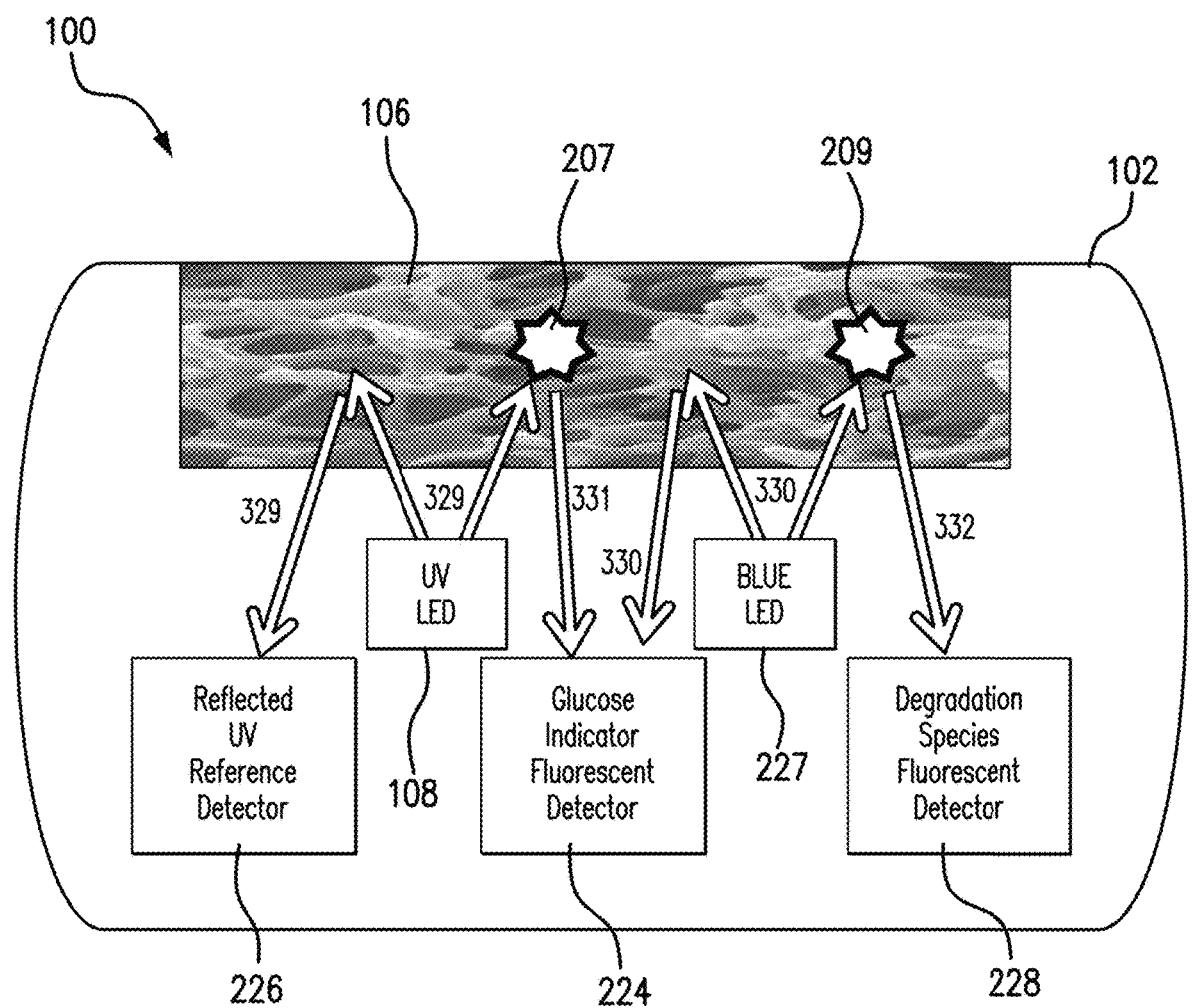
FIGS. 2A and 2B are schematic views each illustrating an analyte sensor embodying aspects of the present invention.
Figure 3:
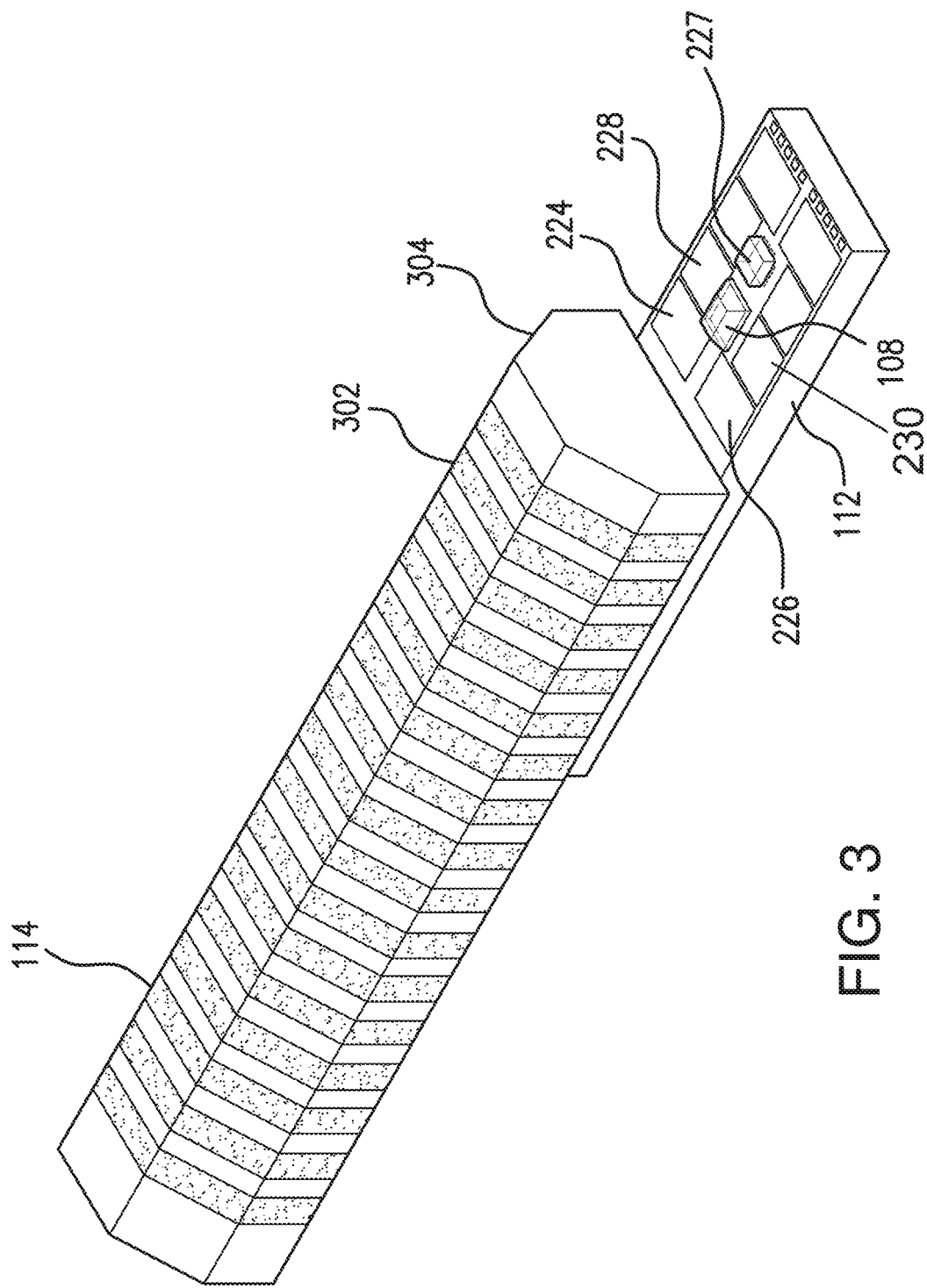
FIG. 3 is a perspective view illustrating elements of an analyte sensor embodying aspects of the present invention.

FIG. 2A is a schematic view illustrating of an analyte sensor 100 embodying aspects of the present invention, and FIG. 3 is a perspective view illustrating elements of an analyte sensor 100 embodying aspects of the present invention. In some aspects, the analyte sensor 100 may detect the presence, amount, and/or concentration of an analyte (e.g., glucose, oxygen, cardiac markers, low-density lipoprotein (LDL), high-density lipoprotein (HDL), or triglycerides). In some non-limiting aspects, the analyte sensor 100 may be optical sensors (e.g., fluorometers). In some aspects, the analyte sensor 100 may be chemical or biochemical sensors. In some aspects, the analyte sensor 100 may be a radio frequency identification (RFID) device. The analyte sensor 100 may be powered by a radio frequency (RF) signal from the transceiver 101.

The analyte sensor 100 may communicate with the transceiver 101. The transceiver 101 may be an electronic device that communicates with the analyte sensor 100 to power the analyte sensor 100 and/or receive measurement data (e.g., photodetector and/or temperature sensor readings) from the analyte sensor 100. The measurement data may include one or more readings from one or more photodetectors of the analyte sensor 100 and/or one or more readings from one or more temperature sensors of the analyte sensor 100. In some aspects, the transceiver 101 may calculate analyte concentrations from the measurement data received from the analyte sensor 100. However, it is not required that the transceiver 101 perform the analyte concentration calculations itself, and, in some alternative aspects, the transceiver 101 may instead convey/relay the measurement data received from the analyte sensor 100 to another device (e.g., display device 107) for calculation of analyte concentrations. In other alternative aspects, the analyte sensor 100 may perform the analyte concentration calculations and convey the calculated analyte concentrations to the transceiver 101.

In some aspects (e.g., aspects in which the analyte sensor 100 is a fully implantable sensing system), the transceiver 101 may implement a passive telemetry for communicating with the implantable analyte sensor 100 via an inductive magnetic link for power and/or data transfer. In some aspects, as shown in FIG. 3, the analyte sensor 100 may include an inductive element 114, which may be, for example, a ferrite based micro-antenna. In some aspects, as shown in FIG. 3, the inductive element 114 may include a conductor 302 in the form of a coil and a magnetic core 304. In some non-limiting aspects, the core 304 may be, for example and without limitation, a ferrite core. In some aspects, the inductive element 114 may be connected to analyte detection circuitry of the analyte sensor 100. For example, in some aspects, where the analyte sensor 100 is an optical sensors, the inductive element 114 may be connected to micro-fluorimeter circuitry (e.g., an application specification integrated circuit (ASIC)) and a related optical detection system of the analyte sensor 100. In some aspects, the analyte sensor 100 may not include a battery, and, as a result, the analyte sensor 100 may rely on the transceiver 101 to provide power for the analyte sensor 100 of the sensor system 105 and a data link to convey analyte-related data from the analyte sensor 100 to transceiver 101. However, this is not required, and, in some alternative aspects, the analyte sensor 100 may include a battery.

In some non-limiting aspects, the analyte sensor 100 may be a passive, fully implantable multisite sensing system having a small size. For an analyte sensor 100 that is a fully implantable sensing system having no battery power source, the transceiver 101 may provide energy to run the analyte sensor 100 via a magnetic field. In some aspects, the magnetic transceiver-sensing system link can be considered as "weakly coupled transformer" type. The magnetic transceiver-sensing system link may provide energy and a link for data transfer using amplitude modulation (AM). Although in some aspects, data transfer is carried out using AM, in alternative aspects, other types of modulation may be used. The magnetic transceiver-sensor link may have a low efficiency of power transfer and, therefore, may require relatively high power amplifier to energize the analyte sensor 100 at longer distances. In some non-limiting aspects, the transceiver 101 and analyte sensor 100 may communicate using near field communication (e.g., at a frequency of 13.56 MHz, which can achieve high penetration through the skin and is a medically approved frequency band) for power transfer. However, this is not required, and, in other aspects, different frequencies may be used for powering and communicating with the analyte sensor 100.

Figure 7:
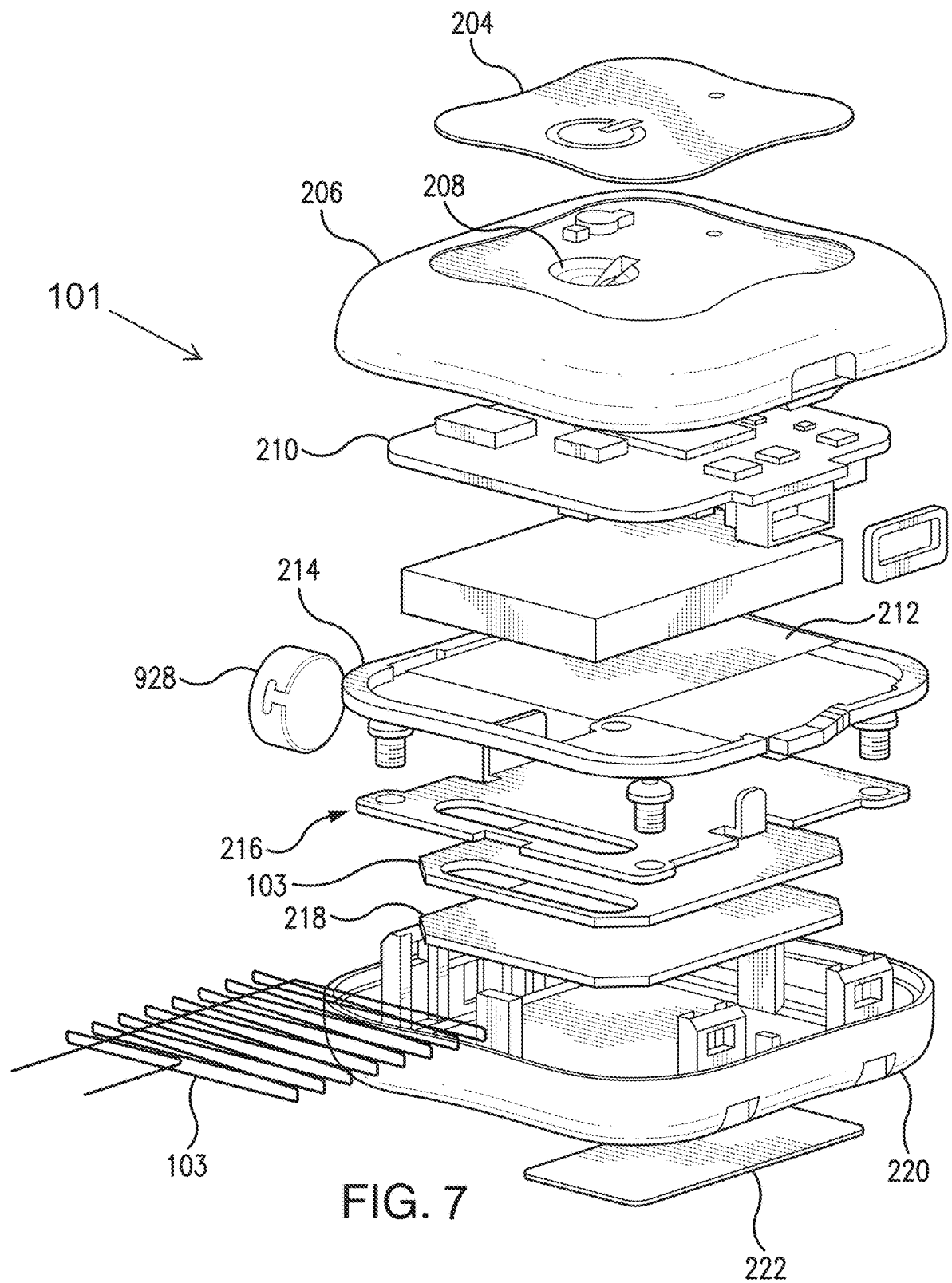
FIG. 7 is an exploded, perspective view of a transceiver embodying aspects of the invention.

In some aspects, as shown in FIG. 7, the transceiver 101 may include an inductive element 103, such as, for example, a coil. The transceiver 101 may generate an electromagnetic wave or electrodynamic field (e.g., by using a coil 103) to induce a current in an inductive element 114 of the analyte sensor 100, which powers the analyte sensor 100. The transceiver 101 may also convey data (e.g., commands) to the analyte sensor 100. For example, in a non-limiting aspect, the transceiver 101 may convey data by modulating the electromagnetic wave used to power the analyte sensor 100 (e.g., by modulating the current flowing through a coil of the transceiver 101). The modulation in the electromagnetic wave generated by the transceiver 101 may be detected/extracted by the analyte sensor 100. Moreover, the transceiver 101 may receive data (e.g., measurement information) from the analyte sensor 100. For example, in a non-limiting aspect, the transceiver 101 may receive data by detecting modulations in the electromagnetic wave generated by the analyte sensor 100, e.g., by detecting modulations in the current flowing through the coil 103 of the transceiver 101.

In some non-limiting aspects, as illustrated in FIG. 2A, the analyte sensor 100 may include a sensor housing 102 (i.e., body, shell, capsule, or encasement), which may be rigid and biocompatible. In one non-limiting aspect, the sensor housing 102 may be a silicon tube. However, this is not required, and, in other aspects, different materials and/or shapes may be used for the sensor housing 102. In some aspects, the analyte sensor 100 may include a transmissive optical cavity. In some non-limiting aspects, the transmissive optical cavity may be formed from a suitable, optically transmissive polymer material, such as, for example, acrylic polymers (e.g., polymethylmethacrylate (PMMA)). However, this is not required, and, in other aspects, different materials may be used for the transmissive optical cavity.

In some aspects, as shown in FIG. 2A, the analyte sensor 100 may include an indicator element 106, such as, for example, a polymer graft or hydrogel coated, diffused, adhered, embedded, or grown on or in at least a portion of the exterior surface of the sensor housing 102. In some non-limiting aspects, the sensor housing 102 may include one or more cutouts or recesses, and the indicator elements 106 may be located (partially or entirely) in the cutouts or recesses. In some aspects, the indicator element 106 may be porous and may allow the analyte (e.g., glucose) in a medium (e.g., interstitial fluid) to diffuse into the indicator element 106.

In some aspects, the indicator element 106 (e.g., polymer graft or hydrogel) of the sensor 100 may include one or more of an analyte indicator 207 and an interferent indicator 209 (e.g., a degradation indicator). In some aspects, the analyte indicator 207 may exhibit one or more detectable properties (e.g., optical properties) that vary in accordance with (i) the amount or concentration of the analyte in proximity to the indicator element 106 and (ii) an effect on the analyte indicator 207 (e.g., changes to the analyte indicator 207). In some aspects, the changes to the analyte indicator 207 may comprise the extent to which the analyte indicator 207 has degraded. In some non-limiting aspects, the degradation may be (at least in part) ROS-induced oxidation. In some aspects, the analyte indicator 207 may include one or more analyte indicator molecules (e.g., fluorescent analyte indicator molecules), which may be distributed throughout the indicator element 106. In some non-limiting aspects, the analyte indicator 207 may be a phenylboronic-based analyte indicator. However, a phenylboronic-based analyte indicator is not required, and, in some alternative aspects, the analyte sensor 100 may include a different analyte indicator, such as, for example and without limitation, glucose oxidase-based indicators, glucose dehydrogenase-based indicators, and glucose binding protein-based indicators.

In some aspects, the interferent indicator 209 may exhibit one or more detectable properties (e.g., optical properties) that vary in accordance with changes to the interferent indicator 209. In some aspects, the interferent indicator 209 is not sensitive to the amount of concentration of the analyte in proximity to the indicator element 106. That is, in some aspects, the one or more detectable properties exhibited by the interferent indicator 209 do not vary in accordance with the amount or concentration of the analyte in proximity to the indicator element 106. However, this is not required, and, in some alternative aspects, the one or more detectable properties exhibited by the interferent indicator 209 may vary in accordance with the amount or concentration of the analyte in proximity to the indicator element 106.

In some aspects, the changes to the interferent indicator 209 may comprise the extent to which the interferent indicator 209 has degraded. In some aspects, the degradation may be (at least in part) ROS-induced oxidation. In some aspects, the interferent indicator 209 may include one or more interferent indicator molecules (e.g., fluorescent interferent indicator molecules), which may be distributed throughout the indicator element 106. In some non-limiting aspects, the interferent indicator 209 may be a phenylboronic-based interferent indicator. However, a phenylboronic-based interferent indicator is not required, and, in some alternative aspects, the analyte sensor 100 may include a different interferent indicator, such as, for example and without limitation, amplex red-based interferent indicators, dichlorodihydrofluorescein-based indicators, dihydrorhodamine-based indicators, and scopoletin-based interferent indicators.

In some non-limiting aspects, an interferent indicator molecule may be a fluorescent probe compound having a wavelength of excitation between about 450 nm and about 550 nm, a Stokes shift between about 500 nm and about 650 nm, and a half-life of between about 50 days and about 150 days. In some non-limiting aspects, an interferent indicator molecule may be a compound of formula I:

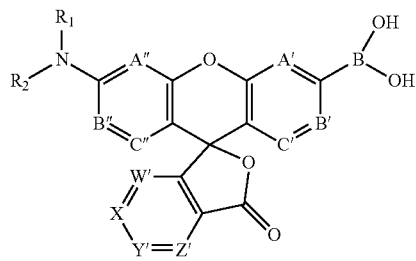

wherein A″, B″, C″, A′, B′, C′, W′, X, Y′, and Z′ represent —CH, wherein the hydrogen may optionally and independently be substituted with an alkyl group, $R_1$ and $R_2$ are independently selected from one or more vinyl groups, alkyl vinyl groups, acrylamide groups, methacrylamide groups, or other polymerizable groups.

Exemplary and non-limiting compounds include the following:

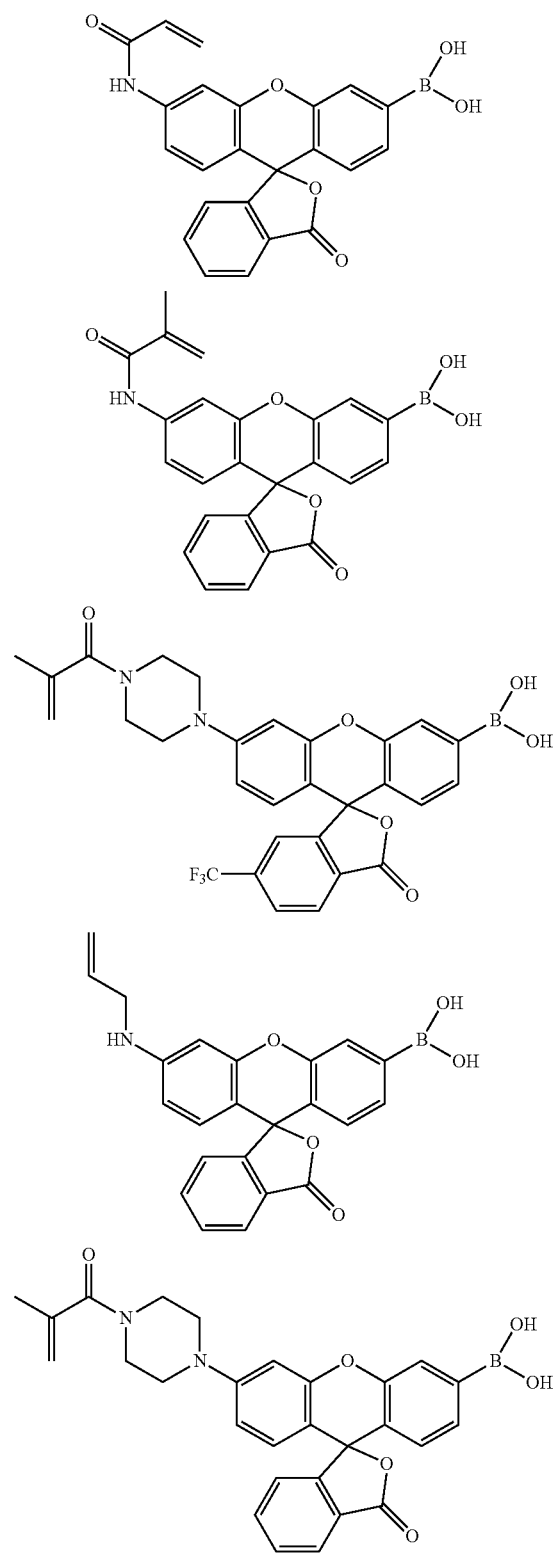

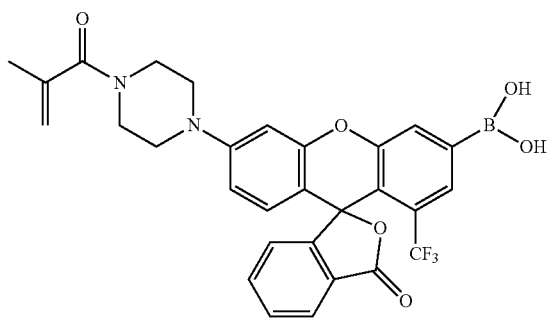
In further non-limiting aspects, an interferent indicator molecule may include exemplary compounds such as the following:
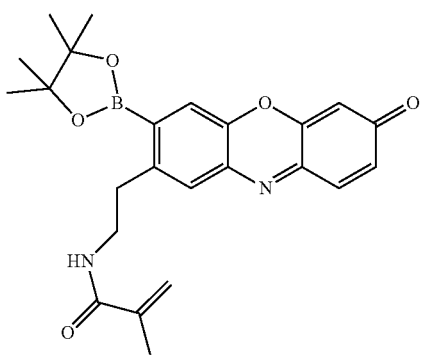
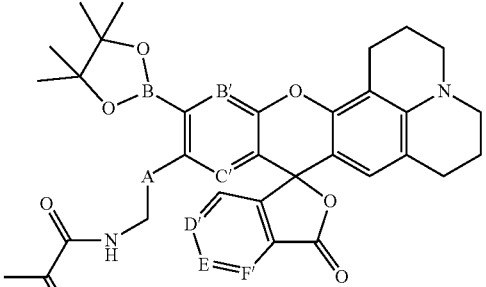
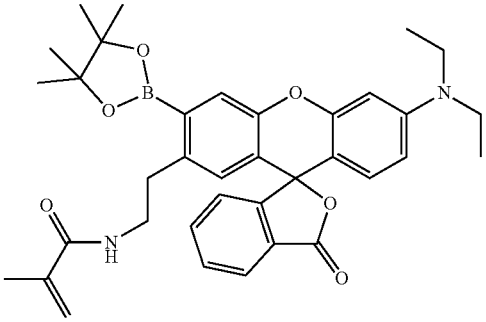
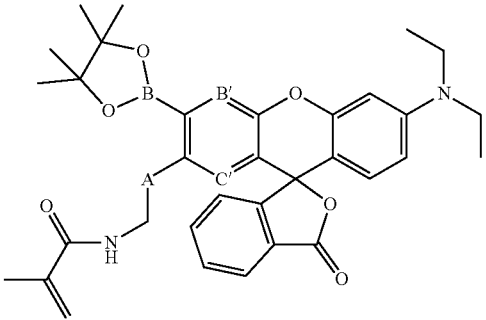
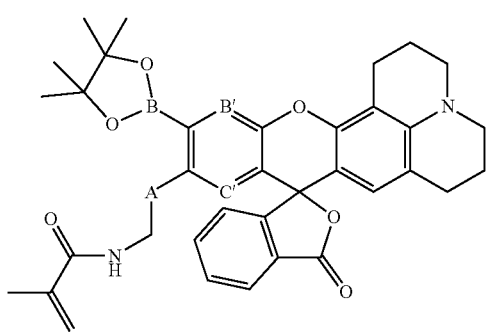
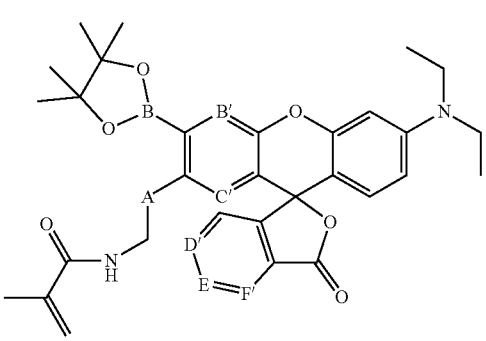

-continued

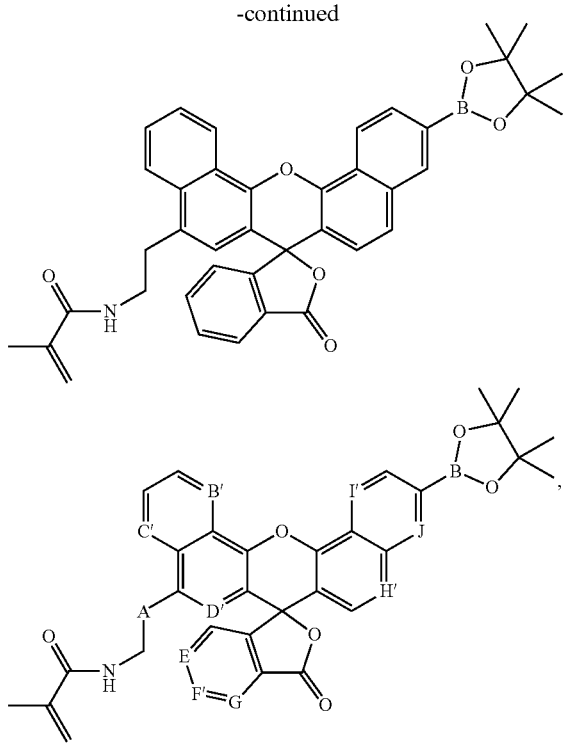

wherein A, B', C', D', E, F', G, H', I', and J represent —CH, wherein the hydrogen may optionally and independently be substituted with an alkyl group.

Compounds may be synthesized using the synthetic techniques known in the art such as in "Preparation and use of MitoPY1 for imaging hydrogen peroxide in mitochondria of live cells," Dickinson, et al. *Nat Protoc.* 2013 June; 8(6): 1249-1259 and U.S. pre-grant publication number US2016/0312033 (application. Ser. No. 15/135,788, Yang et al., Oct. 27, 2016), the disclosures of which are incorporated herein by reference in their entireties.

In some alternative aspects, the molecules of the interferent indicator 209 may be a compound having a different formula having a wavelength of excitation between about 450 nm and about 550 nm, a Stokes shift between about 500 nm and about 650 nm, and a half-life of between about 50 days and about 150 days.

Figure 10:
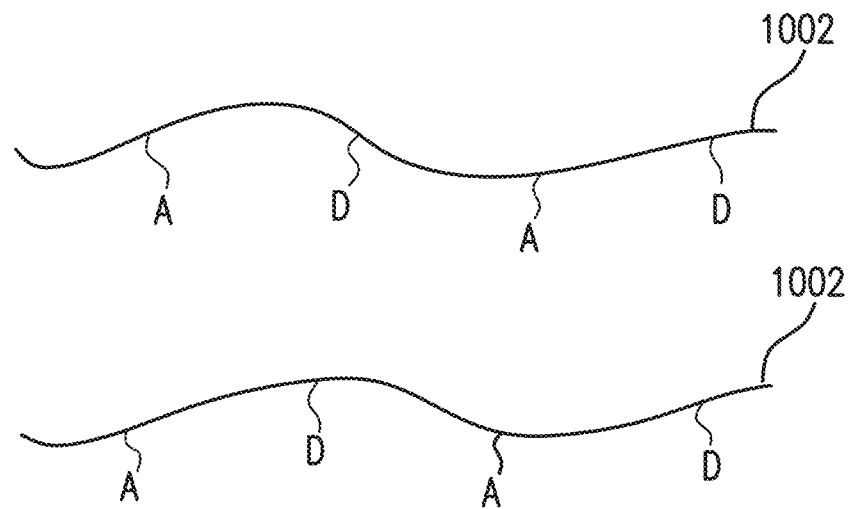
FIGS. 10-12 are schematic diagrams illustrating non-limiting examples of structures of indicator elements 106 embodying aspects of the present invention.
Figure 11:
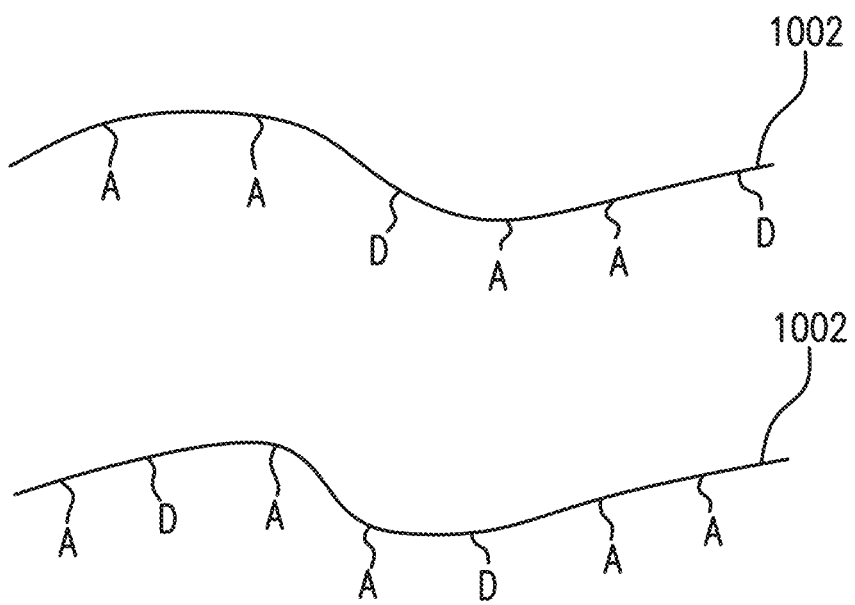
Figure 12:
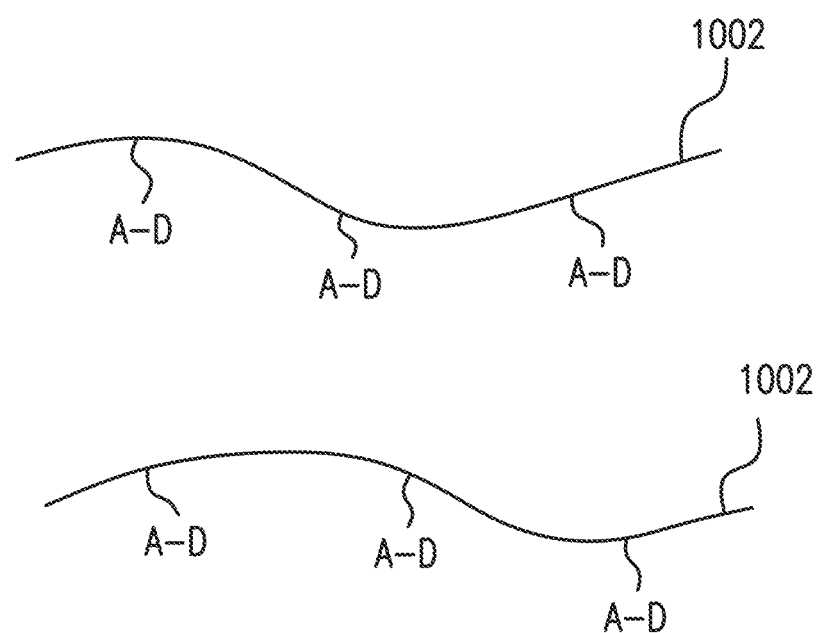

In some non-limiting aspects, as shown in FIGS. 10-12, the indicator element 106 may include one or more polymer backbones 1002. In some non-limiting aspects, the polymer backbones 1002 may be polymer chains. In some aspects, as shown in FIGS. 10 and 11, the indicator element 106 may include one or more analyte indicator molecules A and one or more interferent indicator molecules D. In some aspects, as shown in FIGS. 10 and 11, the analyte indicator molecules A and interferent indicator molecules D may be monomers polymerized individually to a polymer backbone 1002. In some non-limiting aspects, the indicator element 106 may include an equal number of analyte indicator molecules A and interferent indicator molecules D (see FIG. 10) or a different number of analyte indicator molecules A and interferent indicator molecules D (see FIG. 11). In some aspects, there may be a ratio of analyte indicator molecules A to interferent indicator molecules D, such as, for example and without limitation, 1:1 as shown in FIG. 10, 2:1 as shown in FIG. 11, 1:2, 3:1, 5:1, 10:1, etc.

In some alternative aspects, as shown in FIG. 12, one or more interferent indicator molecules D may be chemically bonded to an analyte indicator molecule A (e.g., via a covalent bond), and the analyte indicator molecule A may be chemically bonded to a polymer backbone 1002. In one non-limiting alternative aspect, the analyte indicator molecules A and interferent indicator molecules D may be monomers, and the analyte indicator molecules A may be polymerized to the polymer backbone 1002. In some other alternative aspects, one or more analyte indicator molecules A may be chemically bonded to an interferent indicator molecules D, and the interferent indicator molecule D may be chemically bonded to a polymer backbone 1002. In one non-limiting alternative aspect, the analyte indicator molecules A and interferent indicator molecules D may be monomers, and the interferent indicator molecules D may be polymerized to the polymer backbone 1002.

In some aspects, the analyte sensor 100 may measure changes to the analyte indicator 207 indirectly using the interferent indicator 209, which may by sensitive to degradation by reactive oxygen species (ROS) but not sensitive to the analyte. In some aspects, the interferent indicator 209 may have one or more optical properties that change with extent of oxidation and may be used as a reference dye for measuring and correcting for extent of oxidation of the analyte indicator. In some aspects, the extent to which the interferent indicator 209 has degraded may correspond to the extent to which the analyte indicator 207 has degraded. For example, in some non-limiting aspects, the extent to which the interferent indicator 209 has degraded may be proportional to the extent to which the analyte indicator 207 has degraded. In some non-limiting aspects, the extent to which the analyte indicator 207 has degraded may be calculated based on the extent to which the interferent indicator 209 has degraded. In some aspects, the analyte monitoring system 50 may correct for changes in the analyte indicator 207 using an empiric correlation established through laboratory testing.

In some aspects, as shown in FIG. 2A, the analyte sensor 100 may include one or more first light sources 108 that emit first excitation light 329 over a range of wavelengths that interact with the analyte indicator 207 in the indicator element 106. In some non-limiting aspects, the first excitation light 329 may be ultraviolet (UV) light. In some aspects, the analyte sensor 100 may include one or more light sources 227 that emit second excitation light 330 over a range of wavelengths that interact with the interferent indicator 209 in the indicator element 106. In some non-limiting aspects, the second excitation light 330 may be blue light.

In some aspects, as shown in FIG. 2A, the analyte sensor 100 may also include one or more photodetectors 224, 226, 228 (e.g., photodiodes, phototransistors, photoresistors, or other photosensitive elements). In some aspects, the analyte sensor 100 may include one or more signal photodetectors 224 sensitive to first emission light 331 (e.g., fluorescent light) emitted by the analyte indicator 207 of the indicator element 106 such that a signal generated by a photodetector 224 in response thereto that is indicative of the level of first emission light 331 of the analyte indicator 207 and, thus, the amount of analyte of interest (e.g., glucose). In some non-limiting aspects, the analyte sensor 100 may include one or more reference photodetectors 226 may be sensitive to first excitation light 329 that may be reflected from the indicator element 106 such that a signal generated by a photodetector 226 in response thereto is indicative of the level of reflected first excitation light 329. In some aspects, the analyte sensor 100 may include one or more interferent photodetectors 228 sensitive to second emission light 332 (e.g., fluorescent light) emitted by the interferent indicator 209 of the indicator element 106 such that a signal generated by an interferent photodetector 228 in response thereto is indicative of the level of second emission light 332 of the interferent indicator 209 and, thus, the amount of degradation (e.g., oxidation). In some non-limiting aspects, the one or more signal photodetectors 224 may be sensitive to second excitation light 330 that may be reflected from the indicator element 106. In this way, the one or more signal photodetectors 224 may act as reference photodetectors when the one or more light sources 227 are emitting second excitation light 330.

Figure 2B:
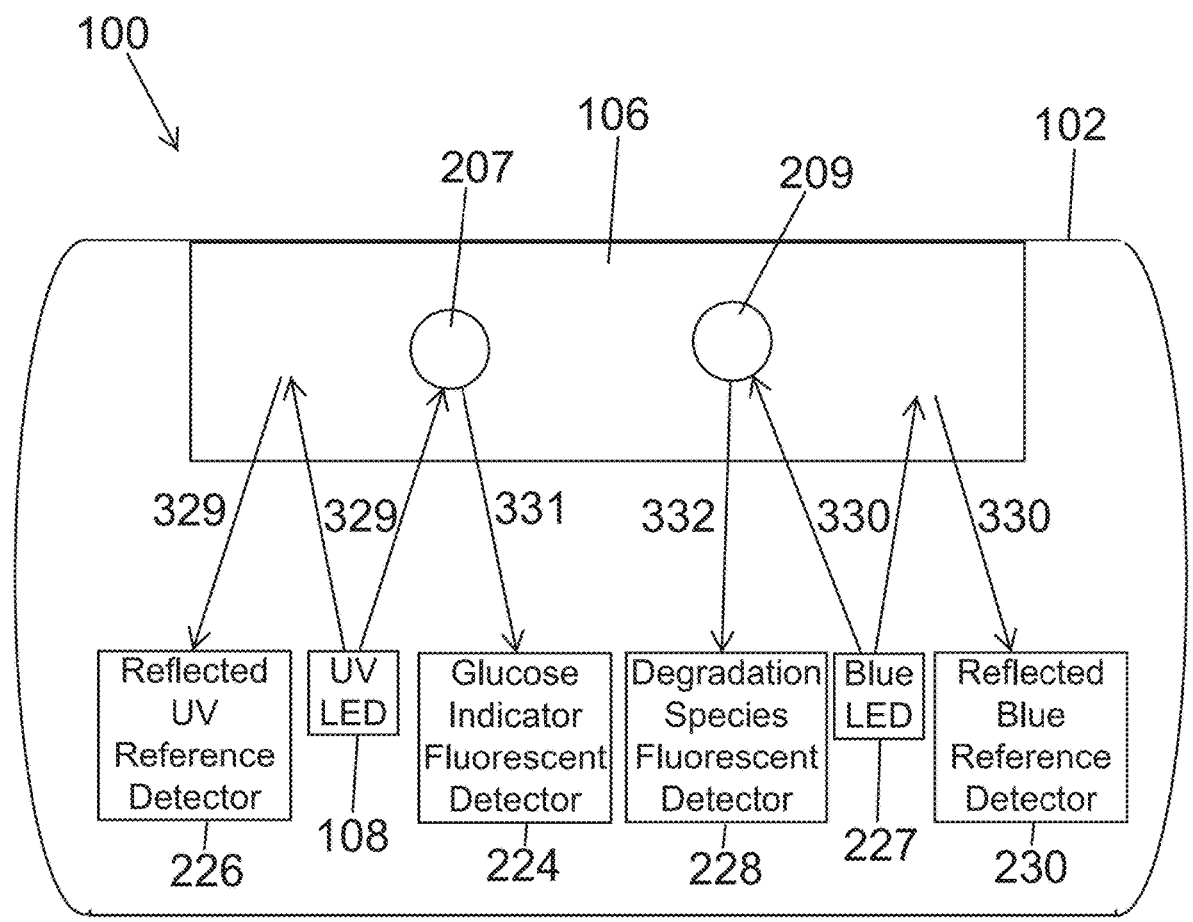

However, it is not required that the one or more signal photodetectors 224 act as reference photodetectors when the one or more light sources 227 are emitting second excitation light 330. In some alternative aspects, as shown in FIG. 2B, the analyte sensor 100 may include one or more second reference photodetectors 230 that act as reference photodetectors when the one or more light sources 227 are emitting second excitation light 330. In some aspects, the one or more second reference photodetectors 230 may be sensitive to second excitation light 330 that may be reflected from the indicator element 106 such that a signal generated by a photodetector 230 in response thereto is indicative of the level of reflected second excitation light 330.

In some aspects, the first excitation light 329 may be over a first wavelength range, and the second excitation light 330 over a second wavelength range, which may different than the first wavelength range. In some non-limiting aspects, the first and second wavelength ranges do not overlap, but this not required, and, in some alternative aspects, the first and second wavelength ranges may overlap. In some aspects, the first emission light 331 may be over a third wavelength range, and the second emission light 332 may be over a fourth wavelength range, which may be different than the third wavelength range. In some non-limiting aspects, the third and fourth wavelength ranges do not overlap, but this is not required, and, in some alternative aspects, the third and fourth wavelength ranges may overlap. In some aspects, the first and third wavelength ranges may be different. In some non-limiting aspects, the first and third wavelength ranges do not overlap, but this is not required, and, in some alternative aspects, the first and third wavelength ranges may overlap. In some aspects, the second and fourth wavelength ranges may be different. In some non-limiting aspects, the second and fourth wavelength ranges do not overlap, but this is not required, and, in some alternative aspects, the second and fourth wavelength ranges may overlap. In some aspects, the second and third wavelength ranges may be different. In some non-limiting aspects, the second and third wavelength ranges may overlap, but this is not required and, in some alternative aspects, the second and third wavelength ranges do not overlap.

In some aspects, one or more of the photodetectors 224, 226, 228, 230 may be covered by one or more filters that allow only a certain subset of wavelengths of light to pass through and reflect (or absorb) the remaining wavelengths. In some non-limiting aspects, one or more filters on the one or more signal photodetectors 224 may allow only a subset of wavelengths corresponding to first emission light 331 and/or the reflected second excitation light 330. In some non-limiting aspects, one or more filters on the one or more reference photodetectors 226 may allow only a subset of wavelengths corresponding to the reflected first excitation light 329. In some non-limiting aspects, one or more filters on the one or more interferent photodetectors 228 may allow only a subset of wavelengths corresponding to second emission light 332. In some non-limiting aspects in which the analyte sensor 100 includes one or more second reference photodetectors 230, one or more filters on the one or more second reference photodetectors 230 may allow only a subset of wavelengths corresponding to the reflected second excitation light 330.

Figure 5:
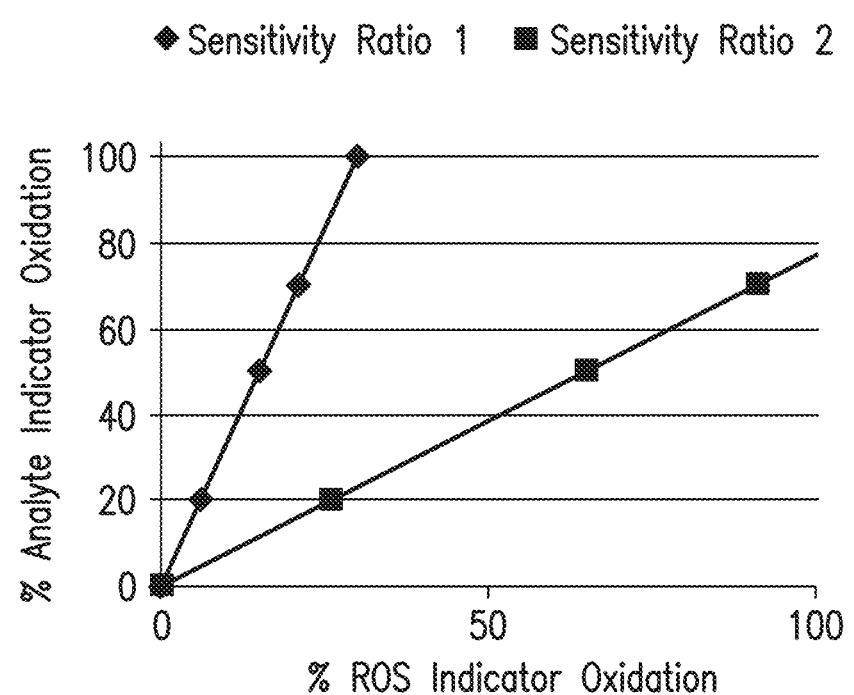
FIG. 5 is a chart illustrating non-limiting examples of sensitivity ratios correlating an analyte indicator to interferent indicators embodying aspects of the present invention.

In some aspects, the interferent indicator 209 may be used as a reference dye for measuring and correcting for extent of oxidation of the analyte indicator 207. In some aspects, the analyte monitoring system 50 may correct for changes in the analyte indicator 207 using an empiric correlation established through laboratory testing. FIG. 5 is a chart illustrating non-limiting examples of sensitivity ratios correlating an analyte indicator 207 to an interferent indicator 209. In some aspects, as shown by the sensitivity ratio 1 in FIG. 5, the interferent indicator 209 may be more sensitive to oxidation than the analyte indicator 207. However, this is not required, and, in some alternative aspects, as shown by the sensitivity ratio 2 in FIG. 5, the interferent indicator 209 may be less sensitive to oxidation than the analyte indicator 207. In some other alternative aspects, the interferent indicator 209 and analyte indicator 207 may be equally sensitive to oxidation.

Figure 4:
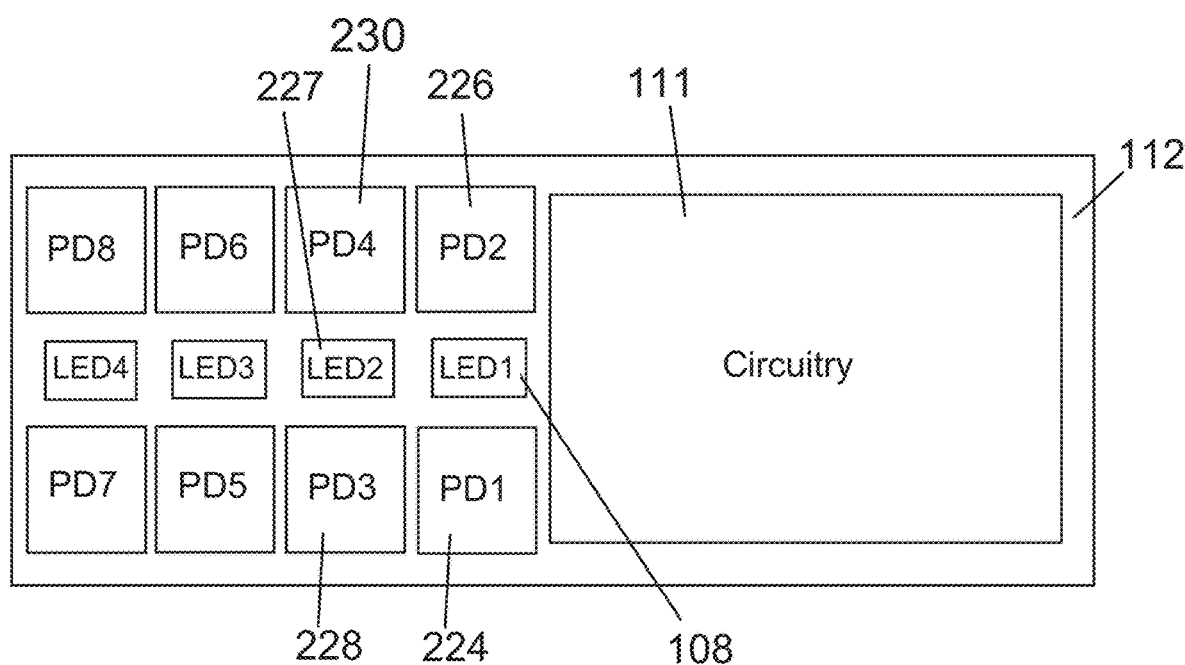
FIG. 4 is a schematic view illustrating the layout of a semiconductor substrate of an analyte sensor embodying aspects of the present invention.

In some aspects, as shown in FIG. 4, the substrate 112 may be a circuit board (e.g., a printed circuit board (PCB) or flexible PCB) on which one or more of the circuit components 111 (e.g., analog and/or digital circuit components) may be mounted or otherwise attached. However, in some alternative aspects, the substrate 112 may be a semiconductor substrate having one or more of the circuit components 111 fabricated therein. For instance, the fabricated circuit components may include analog and/or digital circuitry. Also, in some aspects in which the substrate 112 is a semiconductor substrate, in addition to the circuit components fabricated in the semiconductor substrate, circuit components may be mounted or otherwise attached to the semiconductor substrate. In other words, in some semiconductor substrate aspects, a portion or all of the circuit components 111, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components 111 is secured to the semiconductor substrate, which may provide communication paths between the various secured components.

In some aspects, the analyte sensor 100 may include one or more light sources 108, 227, and one or more of the light sources 108, 227 may be mounted on or fabricated within in the substrate 112. In some aspects, the analyte sensor 100 may include one or more photodetectors 224, 226, 228, 230, and one or more of the photodetectors 224, 226, 228, 230 may be mounted on or fabricated in the substrate 112. In some non-limiting aspects, one or more light sources 108, 227 may be mounted on the substrate 112, one or more photodetectors may be fabricated within the substrate 112, and all or a portion of the circuit components 111 may be fabricated within the substrate 112.

In some aspects, the one or more of the indicator element 106, light source(s) 108, 227, photodetectors 224, 226, 228, 230, circuit components 111, and substrate 112 of the analyte sensor 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the sensor housing 102, analyte sensor 100, and/or transceiver 101 may be as described in one or more of U.S. application Ser. Nos. 13/761,839, 13/937,871, 13/650,016, and 14/142,017. For instance, the sensor housing 102 may have one or more hydrophobic, hydrophilic, opaque, and/or immune response blocking membranes or layers on the exterior thereof.

Although in some aspects, as illustrated in FIG. 1, the analyte sensor 100 may be a fully implantable sensor, this is not required, and, in some alternative aspects, the analyte sensor 100 may be a transcutaneous sensing system having a wired connection to the transceiver 101. For example, in some alternative aspects, the analyte sensor 100 may be located in or on a transcutaneous needle (e.g., at the tip thereof). In these aspects, instead of wirelessly communicating using inductive elements 103 and 114, the analyte sensor 100 and transceiver 101 may communicate using one or more wires connected between the transceiver 101 and the transceiver transcutaneous needle that includes the analyte sensor 100. For another example, in some alternative aspects, the analyte sensor 100 may be located in a catheter (e.g., for intravenous blood glucose monitoring) and may communicate (wirelessly or using wires) with the transceiver 101.

In some aspects, the analyte sensor 100 may include a transceiver interface device. In some aspects, the transceiver interface device may include the antenna (e.g., inductive element 114) of the analyte sensor 100. In some of the transcutaneous aspects where there exists a wired connection between the analyte sensor 100 and the transceiver 101, the transceiver interface device may include the wired connection.

Figure 6:
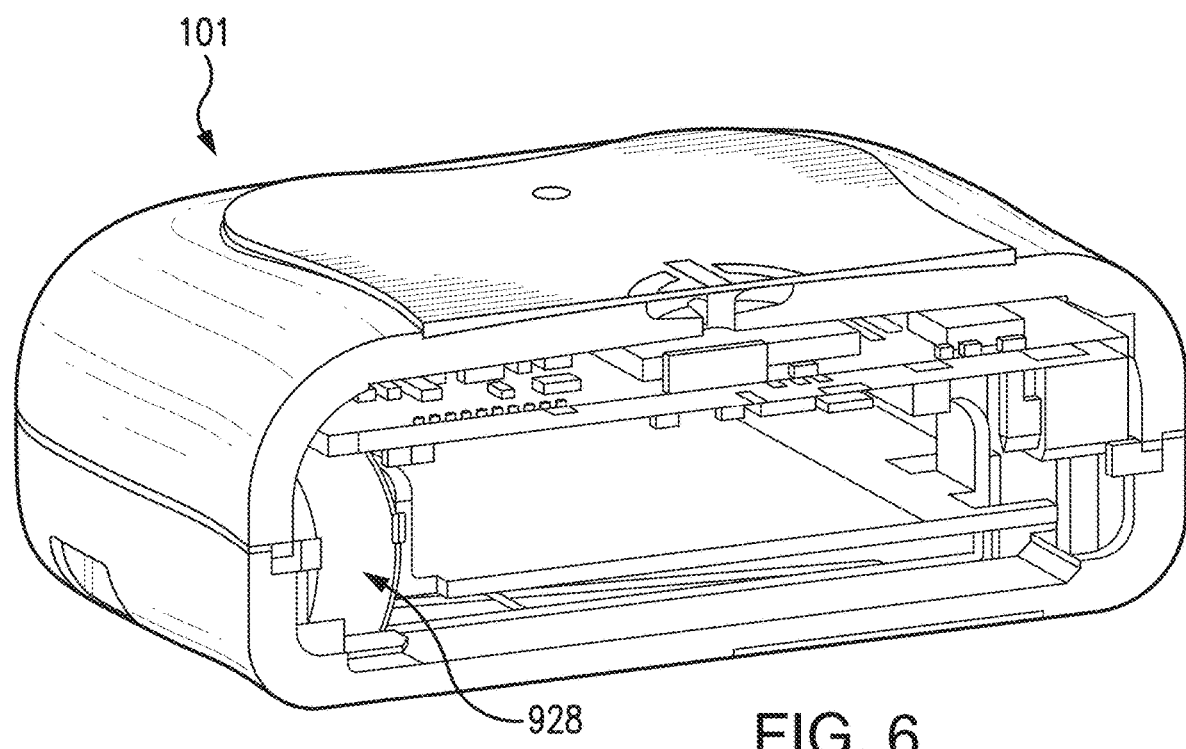
FIG. 6 is cross-sectional, perspective view of a transceiver embodying aspects of the invention.

FIGS. 6 and 7 are cross-sectional and exploded views, respectively, of a non-limiting aspect of the transceiver 101, which may be included in the analyte monitoring system 50 illustrated in FIG. 1. As illustrated in FIG. 7, in some non-limiting aspects, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting aspects, the vibration motor 928 may be attached to the front housing 206 or back housing 220 such that the battery 212 does not dampen the vibration of vibration motor 928. In a non-limiting aspect, the transceiver electronics may be assembled using standard surface mount device (SMD) reflow and solder techniques. In one aspect, the electronics and peripherals may be put into a snap together housing design in which the front housing 206 and back housing 220 may be snapped together. In some aspects, the full assembly process may be performed at a single external electronics house. However, this is not required, and, in alternative aspects, the transceiver assembly process may be performed at one or more electronics houses, which may be internal, external, or a combination thereof. In some aspects, the assembled transceiver 101 may be programmed and functionally tested. In some aspects, assembled transceivers 101 may be packaged into their final shipping containers and be ready for sale.

In some aspects, as illustrated in FIGS. 6 and 7, the antenna 103 may be contained within the housing 206 and 220 of the transceiver 101. In some aspects, the antenna 103 in the transceiver 101 may be small and/or flat so that the antenna 103 fits within the housing 206 and 220 of a small, lightweight transceiver 101. In some aspects, the antenna 103 may be robust and capable of resisting various impacts. In some aspects, the transceiver 101 may be suitable for placement, for example, on an abdomen area, upper-arm, wrist, or thigh of a patient body. In some non-limiting aspects, the transceiver 101 may be suitable for attachment to a patient body by means of a biocompatible patch. Although, in some aspects, the antenna 103 may be contained within the housing 206 and 220 of the transceiver 101, this is not required, and, in some alternative aspects, a portion or all of the antenna 103 may be located external to the transceiver housing. For example, in some alternative aspects, antenna 103 may wrap around a user's wrist, arm, leg, or waist such as, for example, the antenna described in U.S. Pat. No. 8,073,548, which is incorporated herein by reference in its entirety.

Figure 8:
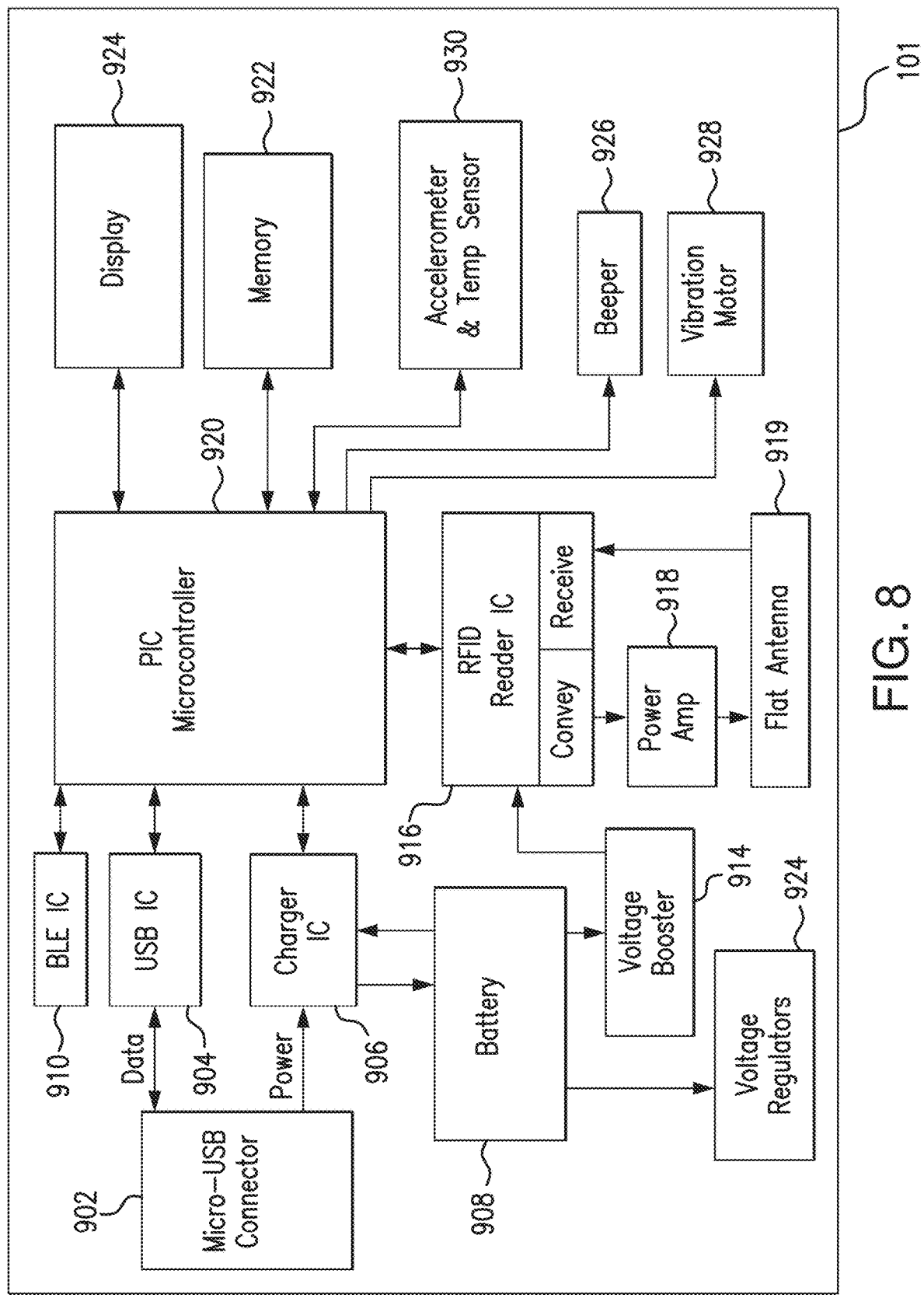
FIG. 8 is a schematic view illustrating a transceiver embodying aspects of the present invention.

FIG. 8 is a schematic view of an external transceiver 101 according to a non-limiting aspect. In some aspects, the transceiver 101 may have a connector 902, such as, for example, a Micro-Universal Serial Bus (USB) connector. The connector 902 may enable a wired connection to an external device, such as a personal computer (e.g., personal computer 109) or a display device 107 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some aspects, the battery 908 may be rechargeable, may have a short recharge duration, and/or may have a small size.

In some aspects, the transceiver 101 may include one or more connectors in addition to (or as an alternative to) Micro-USB connector 904. For example, in one alternative aspect, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 107 (e.g., a smartphone) and/or to receive power, which may be used, for example, to charge the battery 908.

In some aspects, the transceiver 101 may have a wireless communication IC 910, which enables wireless communication with an external device, such as, for example, one or more personal computers (e.g., personal computer 109) or one or more display devices 107 (e.g., a smartphone). In one non-limiting aspect, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting aspects, the wireless communication IC 910 may be configured to wirelessly transmit data at a frequency greater than 1 gigahertz (e.g., 2.4 or 5 GHz). In some aspects, the wireless communication IC 910 may include an antenna (e.g., a Bluetooth antenna). In some non-limiting aspects, the antenna of the wireless communication IC 910 may be entirely contained within the housing (e.g., housing 206 and 220) of the transceiver 101. However, this is not required, and, in alternative aspects, all or a portion of the antenna of the wireless communication IC 910 may be external to the transceiver housing.

In some aspects, the transceiver 101 may include a display interface device, which may enable communication by the transceiver 101 with one or more display devices 107. In some aspects, the display interface device may include the antenna of the wireless communication IC 910 and/or the connector 902. In some non-limiting aspects, the display interface device may additionally include the wireless communication IC 910 and/or the connector IC 904.

In some aspects, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting aspects, the sensor 100 and transceiver 101 may communicate using near field communication (NFC) (e.g., at a frequency of 13.56 MHz). In the illustrated aspect, the inductive element 103 is a flat antenna. In some non-limiting aspects, the antenna may be flexible. However, as noted above, the inductive element 103 of the transceiver 101 may be in any configuration that permits adequate field strength to be achieved when brought within adequate physical proximity to the inductive element 114 of the sensor 100. In some aspects, the transceiver 101 may include a power amplifier 918 to amplify the signal to be conveyed by the inductive element 103 to the sensor 100.

In some aspects, the transceiver 101 may include a peripheral interface controller (PIC) controller 920 and memory 922 (e.g., Flash memory), which may be non-volatile and/or capable of being electronically erased and/or rewritten. The PIC controller 920 may control the overall operation of the transceiver 101. For example, the PIC controller 920 may control the connector IC 904 or wireless communication IC 910 to transmit data via wired or wireless communication and/or control the RFID reader IC 916 to convey data via the inductive element 103. The PIC controller 920 may also control processing of data received via the inductive element 103, connector 902, or wireless communication IC 910.

In some aspects, the transceiver 101 may include a sensor interface device, which may enable communication by the transceiver 101 with a sensor 100. In some aspects, the sensor interface device may include the inductive element 103. In some non-limiting aspects, the sensor interface device may additionally include the RFID reader IC 916 and/or the power amplifier 918. However, in some alternative aspects where there exists a wired connection between the sensor 100 and the transceiver 101 (e.g., transcutaneous aspects), the sensor interface device may include the wired connection.

In some aspects, the transceiver 101 may include a display 924 (e.g., liquid crystal display and/or one or more light emitting diodes), which PIC controller 920 may control to display data (e.g., analyte concentration values). In some aspects, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor that may be used in the processing performed by the PIC controller 920.

Figure 9:
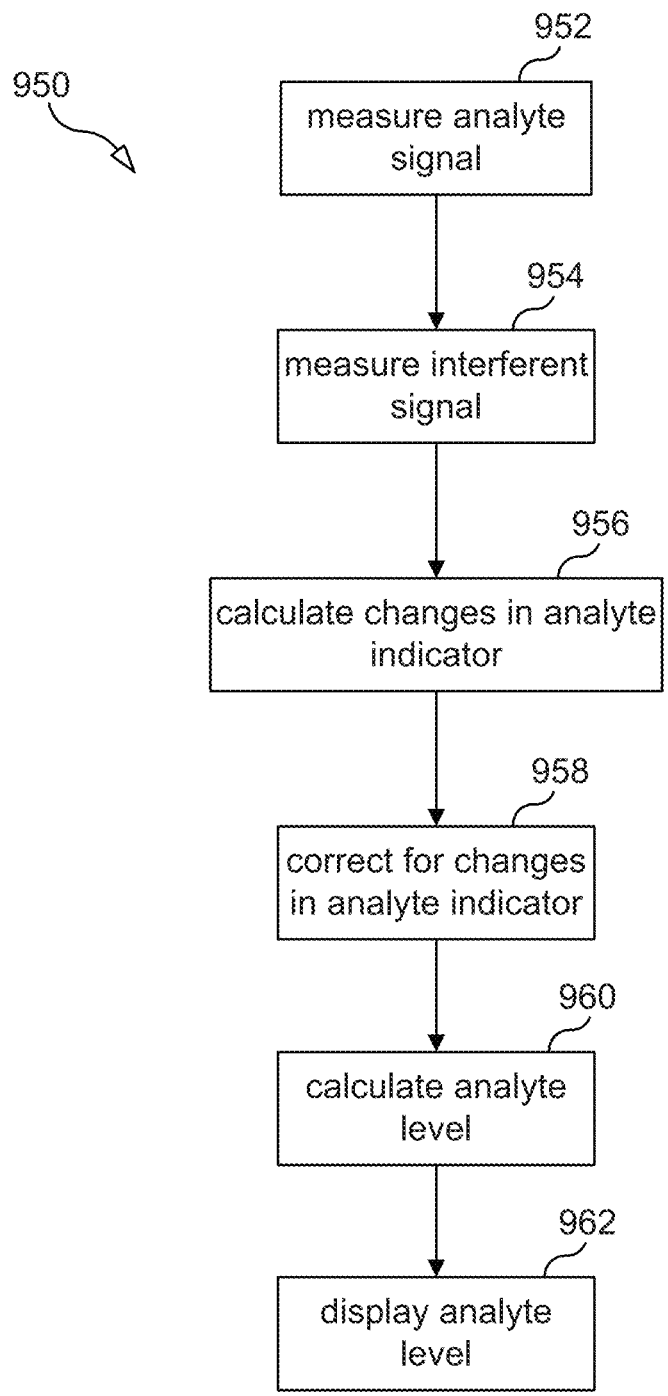
FIG. 9 is a flow chart illustrating a process for detecting and correcting for changes to an analyte indicator embodying aspects of the present invention.

FIG. 9 illustrates non-limiting aspect of an analyte monitoring process 950 that may be performed by the analyte monitoring system 50. In some aspects, the process 950 may detect and correct for an effect on the analyte indicator 207.

In some aspects, the process 950 may include a step 952 in which the analyte monitoring system 50 measures an analyte signal. In some aspects, the step 952 may include the transceiver 101 conveying an analyte measurement command to the analyte sensor 100. In some aspects, the step 952 may include the analyte sensor 100, in response to receiving and decoding the analyte measurement command, using the first light source 108 to emit first excitation light 329 to the indicator element 106. The analyte indicator 207 of the indicator element 106 may receive the first excitation light 329 and emit first emission light 331. The signal photodetector 224 may receive the first emission light 331 and generate an analyte measurement signal based on the amount of first emission light 331 received by the signal photodetector 224. In some aspects, the step 952 may include the analyte sensor 100 using the reference photodetector 226 to receive first excitation light 329 that was reflected from the indicator element 106 and generate a reference signal indicative of the amount of reflected first excitation light 329 received by the reference photodetector 226.

In some aspects, the process 950 may include a step 954 in which the analyte monitoring system 50 measures an interferent signal. In some aspects, the step 954 may include the transceiver 101 conveying an interferent measurement command to the analyte sensor 100. In some aspects, the step 954 may include the analyte sensor 100, in response to receiving and decoding the interferent measurement command, using the second light source 227 to emit second excitation light 330 to the indicator element 106. The interferent indicator 209 of the indicator element 106 may receive the second excitation light 330 and emit second emission light 332. The interferent photodetector 228 may receive the second emission light 332 and generate an interferent measurement signal based on the amount of second emission light 332 received by the interferent photodetector 228. In some aspects, the step 954 may include the analyte sensor 100 using the signal photodetector 224 (and/or the second reference photodetector 230) to receive second excitation light 330 that was reflected from the indicator element 106 and generate a reference signal indicative of the amount of reflected second excitation light 330 received by the signal photodetector 224 (and/or the second reference photodetector 230).

In some alternative aspects, the step 954 may not include conveying an interferent measurement command to the analyte sensor 100, and the analyte sensor 100 may use the second light source 227 to emit the second excitation light 330 to the indicator element 106 in response to receiving and decoding an analyte measurement command (instead of in response to receiving and decoding a separate interferent measurement command). In some alternative aspects, steps 952 and 954 may be performed simultaneously, and the analyte sensor 100 may use the first and second light sources 108, 227 to emit simultaneously the first and second excitation lights 329, 330 to the indicator element 106. In some alternative aspects, step 954 may be performed before step 952.

In some aspects, the process 950 may include a step 956 in which the analyte monitoring system 50 calculates changes in the analyte indicator 207. In some aspects, the step 956 may include the transceiver 101 receiving sensor data from the analyte sensor 100. In some aspects, the sensor data may include one or more of an analyte measurement, a first reference measurement, an interferent measurement, a second reference measurement, and a temperature measurement. In some aspects, the analyte measurement may correspond to the amount of first emission light 331 received by the signal photodetector 224, the first reference measurement may correspond to the amount of reflected first excitation light 329 received by the reference photodetector 226, the interferent measurement may correspond to the amount of second emission light 332 received by the interferent photodetector 228, and the second reference measurement may correspond to the amount of reflected second excitation light 330 received by the signal photodetector 224. In some alternative aspects, one or more of the analyte measurement and the first reference measurement may be received during step 952, and one or more of the interferent measurement and the second reference measurement may be received during step 954.

In some aspects, the step 956 may include the transceiver 101 (e.g., the microcontroller 910 of the transceiver 101) determining the extent that the analyte indicator 207 has degraded based at least on the received interferent measurement. In some non-limiting aspects, the step 956 may include the transceiver 101 determining (i) the extent that the interferent indicator 209 has been degraded based on the received interferent measurement and (ii) the extent that the analyte indicator 207 has been degraded based on the determined extent to which the interferent indicator 209 has been degraded. In some non-limiting aspects, the transceiver 101 may additionally or alternatively use one or more previous interferent measurements and/or one or more previous determinations of the extent to which the interferent indicator 209 has degraded to determine the extent to which the analyte indicator 207 has degraded.

In some aspects, the process 950 may include a step 958 in which the analyte monitoring system 50 corrects for the calculated changes to the analyte indicator 207 and/or the calculated amount of blood in the ISF. In some non-limiting aspects, the transceiver 101 (e.g., the microcontroller 910 of the transceiver 101) may correct for the calculated changes to the analyte indicator 207 and/or the calculated amount of blood in the ISF by adjusting a conversion function used to calculate an analyte level based on an analyte measurement. In some aspects, adjusting the conversion function may include adjusting one or more parameters of the conversion function. In some aspects, in step 958, the transceiver 101 may additionally or alternatively adjust the conversion function based on the first reference measurement, which may be indicative of in-vivo hydration of the indicator element 106 and/or wound healing kinetics. In some aspects, in step 958, the transceiver 101 may additionally or alternatively adjust the conversion function based on the second reference measurement, which may be a measurement of the opacity of the indicator element 106 in the wavelength range of the first emission light 331.

In some aspects, the process 950 may include a step 960 in which the analyte monitoring system 50 calculates an analyte level (e.g., an analyte concentration). In some aspects, in step 960, the transceiver 101 (e.g., the microcontroller 910 of the transceiver 101) may calculate the analyte level using at least the adjusted conversion function and the analyte measurement. In some aspects, the transceiver 101 may additionally use the temperature measurement to calculate the analyte level.

In some aspects, the process 950 may include a step 962 in which the analyte monitoring system 50 displays the calculated analyte level. In some aspects, in step 962, the transceiver 101 may display the analyte level on the display 924. In some aspects, in step 962, the transceiver 101 may additionally or alternatively convey the calculated analyte level to the display device 107, and the display device 107 may additionally or alternatively convey the calculated analyte level.

EXAMPLE

Compound A was copolymerized with an indicator molecule onto a hydrogel. Methods of copolymerizing are described in U.S. Pat. No. 7,060,503 (Colvin) and U.S. Pat. No. 9,778,190 (Huffstetler et al.), which are incorporated by reference in their entireties.

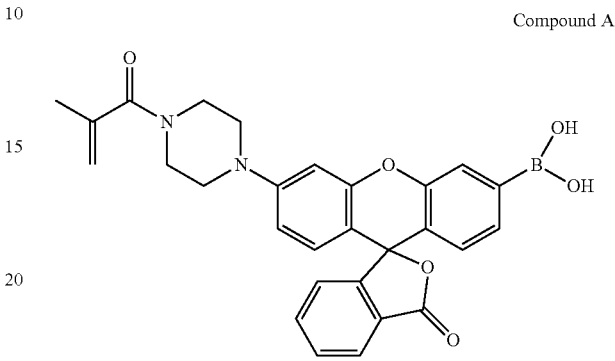

Compound A

Figure 14B:
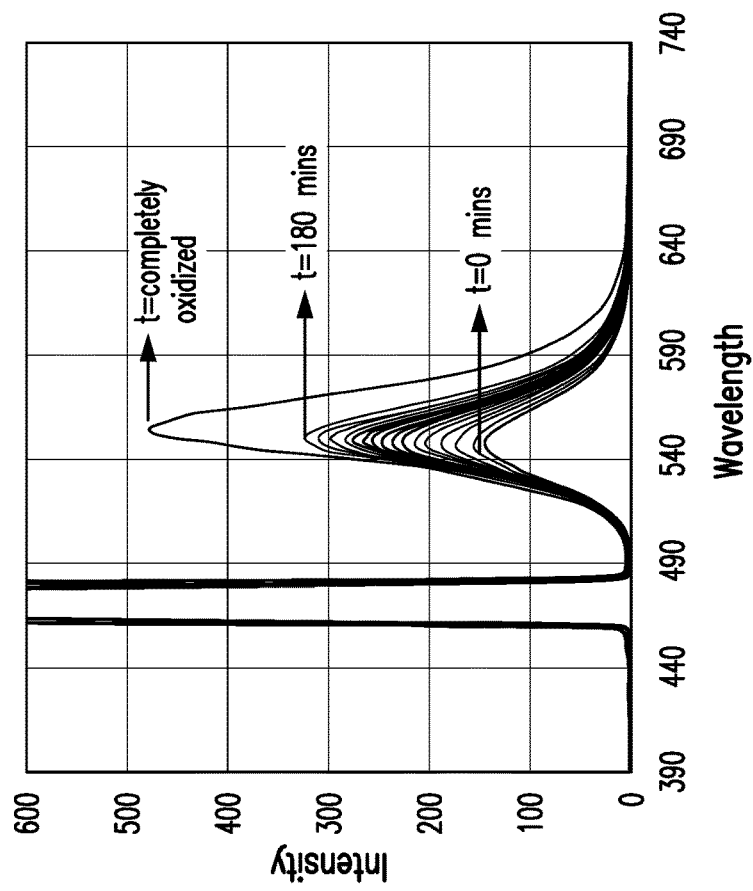
FIGS. 14A and 14B show fluorimeter readings demonstrating decrease in fluorescence intensity of indicator molecule (excitation wavelength 380 nm) at 2 mM glucose and 50 uM hydrogen peroxide with simultaneous increase in the fluorescence intensity of Compound A (excitation wavelength 470 nm) at a 1:1 ratio of indicator molecule:Compound A demonstrating the use of Compound A as a copolymerizable reference dye.
Figure 14A:
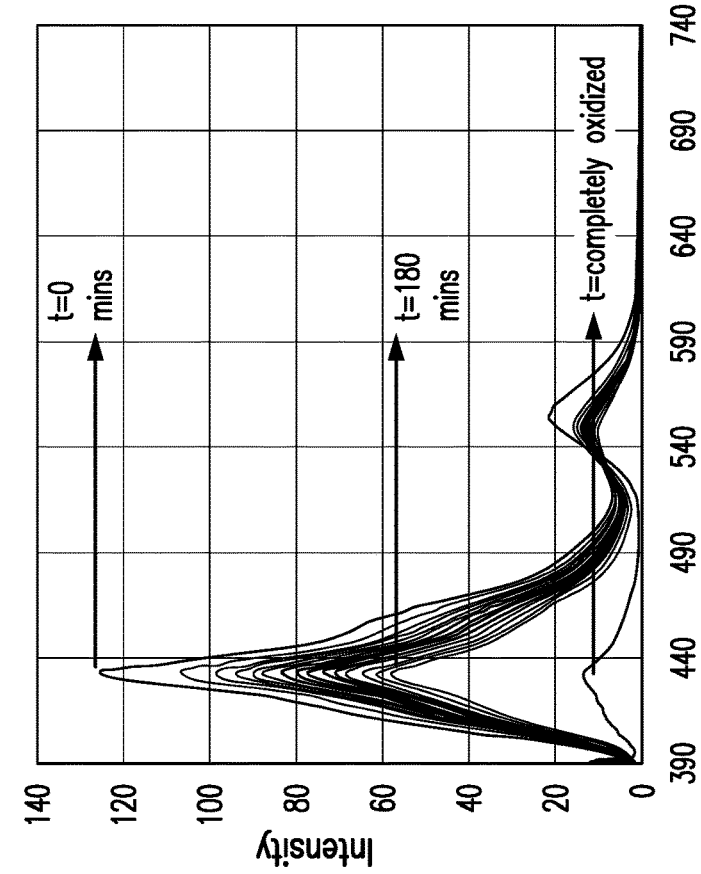

Initial characterization followed by subsequent oxidation test helped in understanding the degradation kinetics of both the reference dye (Compound A) and the indicator as shown in FIGS. 14A and 14B. Initial fluorimeter work was performed with a 1:1 ratio of indicator (TFM):Compound A demonstrating the use of Compound A as a copolymerizable reference dye. The plots in FIG. 14A and FIG. 14B demonstrate decreases in fluorescence intensity of indicator molecule (excitation wavelength 380 nm) at 2 mM glucose and 50 uM hydrogen peroxide with simultaneous increase in the fluorescence intensity of Compound A (excitation wavelength 470 nm). TFM has a chemical name of 9-[N-[6-(4,4,5,5-tetramethyl-1,3,2-dioxaborolano)-3-(trifluoromethyl)benzyl]-N-[3-(methacrylamido)propylamino]methyl]-10-[N-[6-(4,4,5,5-tetramethyl-1,3,2-dioxaborolano)-3-trifluoromethyl)benzyl]-N-[2-(carboxyethyl)amino]methyl]anthracene sodium salt.

An in vivo study was performed in 18 female guinea pigs using mock sensors having a 1:1 ratio of the copolymerized indicator:Compound A in a hydrogel thereon were implanted into the guinea pigs to assess performance of Compound A in response to in vivo oxidation and its correlation to degradation of the indicator molecule. Implantation was executed subcutaneously in the back of each guinea pig (2 samples per guinea pig) with the Senseonics implant tool kit according to the implant training file. The subjects were divided into three groups of explant time points, which were at day 30, 60 and 90. Once the samples were explanted, they were washed and disinfected using ENZOL® enzymatic detergent and glutaraldehyde solution. The explanted samples were then analyzed by fluorimetry to evaluate fluorescence intensity change in Compound A and to correlate % increase in Compound A intensity to % modulation loss in the indicator.

Figure 13:
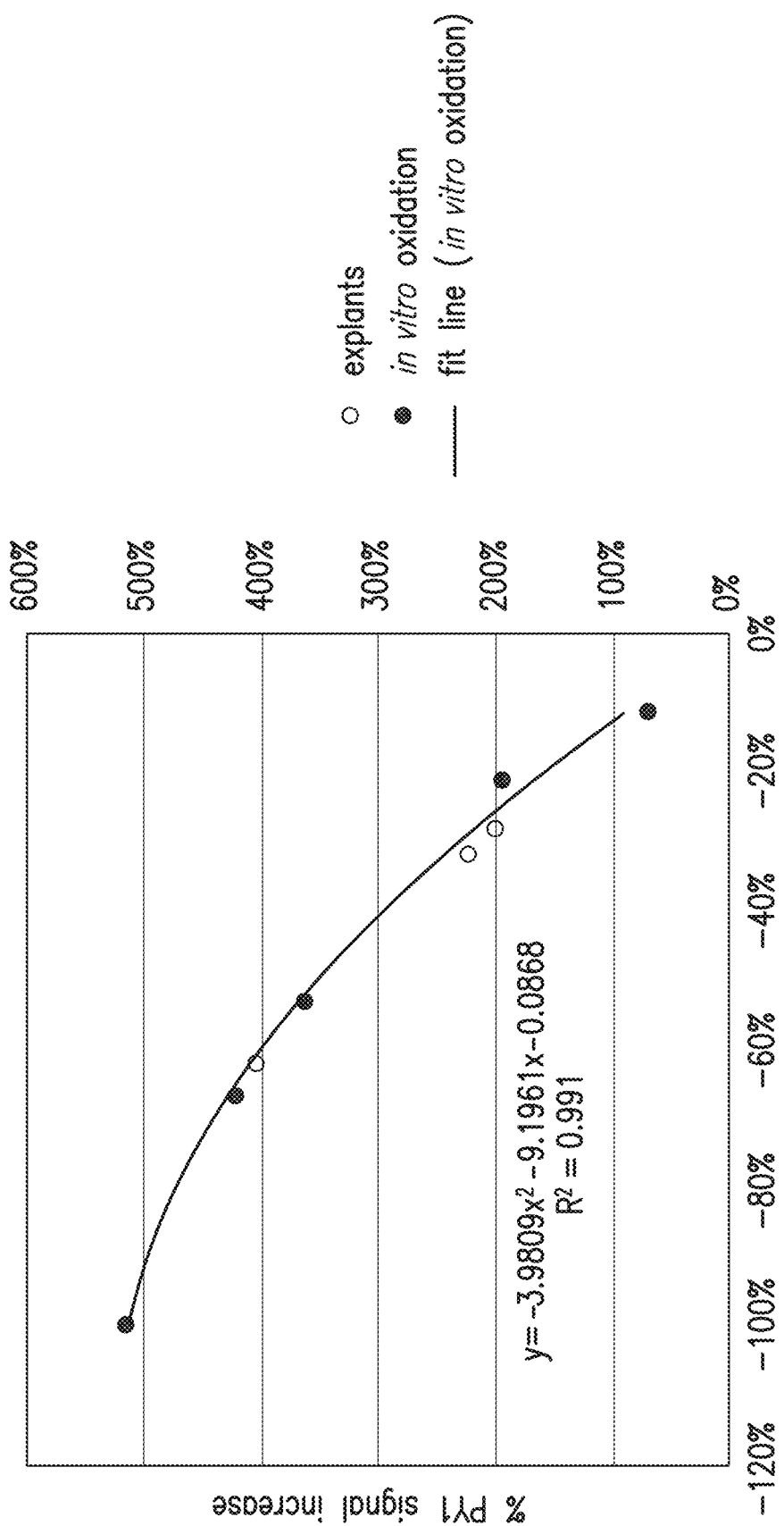
FIG. 13 is a graph illustrating a correlation plot of the rates of interferent of the indicator and the reference dyes according to one non-limiting aspect of the invention.

An in vitro study was performed as follows: An initial 0-18 modulations were done prior to oxidation test to collect the initial modulation data. A known concentration of hydrogen peroxide was used to deliberately oxidize the sensor partially. After partial oxidation, the 0-18 modulations were performed again to collect the modulation data and record the loss in modulation. This procedure was repeated for 3-5 cycles where the same sensor undergoes further partial oxidation and at each oxidized step a 0-18 modulation data was collected. A correlation plot of the rates of degradation of both indicator and the reference dye is shown in FIG. 13.

In explant analysis of the samples, the samples showed a strong correlation between the in vitro and in vivo oxidized samples. This correlation is useful for determining the amount of modulation left at the signal channel by analyzing the amount of the indicator dye oxidation thereby reducing the number of calibrations that are performed.

Additional Aspects

Figure 15A:
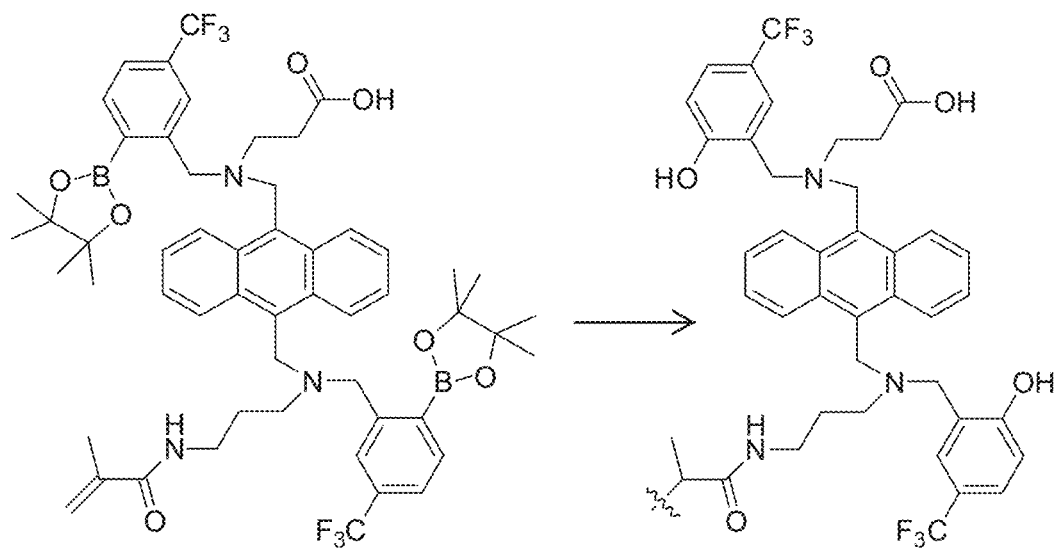
FIG. 15A shows a non-limiting example of an analyte indicator molecule of the analyte indicator before and after degradation caused by reactive oxygen species (ROS) according to aspects of the present invention.

In some aspects, the intensity or amount of emission light (e.g., first emission light 331) emitted by the analyte indicator 207 may change (e.g., increase or decrease) as degradation of the analyte indicator 207 increases. For instance, FIG. 15A shows a non-limiting example of an analyte indicator molecule of the analyte indicator 207 before and after degradation caused by reactive oxygen species (ROS). In some aspects, as shown in FIG. 14A, the intensity or amount of emission light (e.g., first emission light 331) emitted by an analyte indicator 207 including the analyte indicator molecule shown in FIG. 15A may decrease as degradation of the analyte indicator 207 increases over time.

Figure 15B:
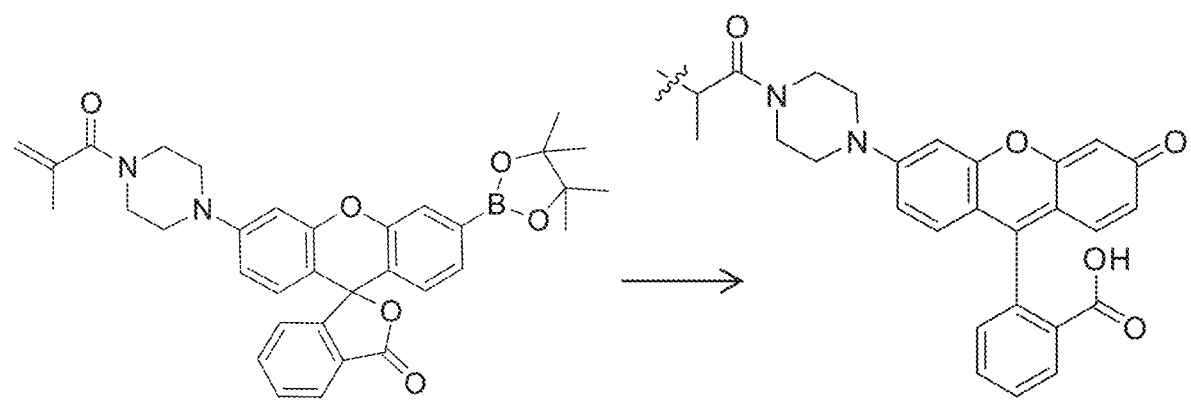
FIG. 15B shows a non-limiting example of an interferent indicator molecule of the interferent indicator before and after degradation caused by ROS according to aspects of the present invention.

In some aspects, the intensity or amount of emission light (e.g., second emission light 332) emitted by the interferent indicator 209 may change (e.g., increase or decrease) as degradation of the interferent indicator 209 increases. In some aspects, the extent of the degradation of the interferent indicator 209 may correspond to the extent of degradation of the analyte indicator 207. Accordingly, in some aspects, the extent of the change in the intensity or amount of emission light emitted by the interferent indicator 209 may correspond to the change in the intensity or amount of emission light emitted by the analyte indicator 207. For instance, FIG. 15B shows a non-limiting example of an interferent indicator molecule of the interferent indicator 209 before and after degradation caused by ROS. In some aspects, as shown in FIG. 14B, the intensity or amount of emission light (e.g., second emission light 332) emitted by an interferent indicator 209 including the analyte indicator molecule shown in FIG. 15B may increase as degradation of the interferent indicator 209 increases over time. However, this is not required, and, in some alternative aspects, the intensity or amount of emission light (e.g., second emission light 332) emitted by an interferent indicator 209 may decrease as degradation of the interferent indicator 209 increases over time.

Figure 16A:
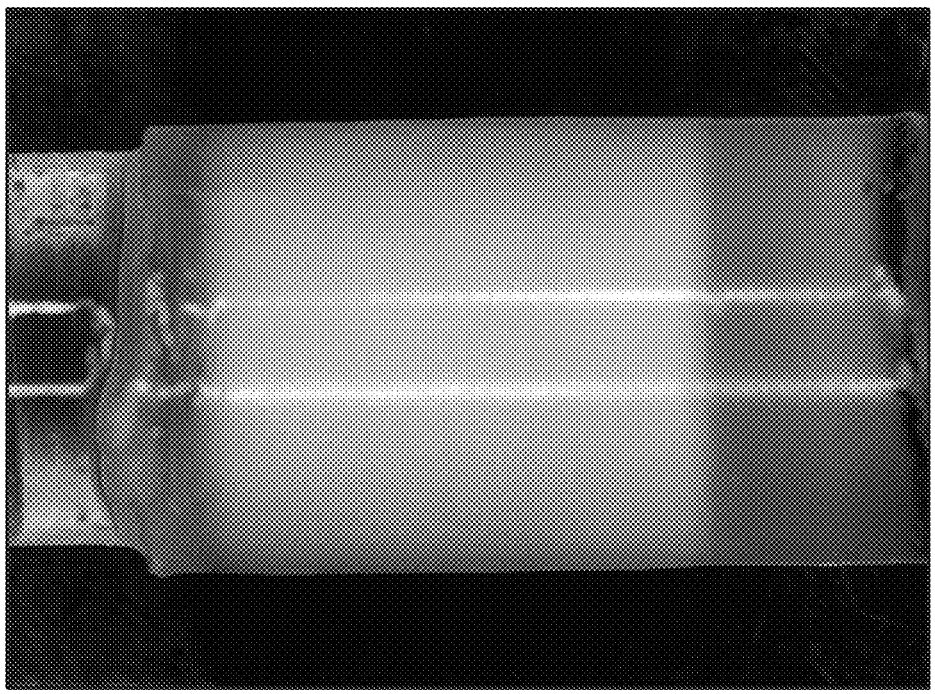
FIGS. 16A and 16B illustrate the white color of an indicator element with no oxidation and the yellow color of the oxidized indicator element, respectively, for an indicator element including an interferent indicator embodying aspects of the present invention.
Figure 16B:
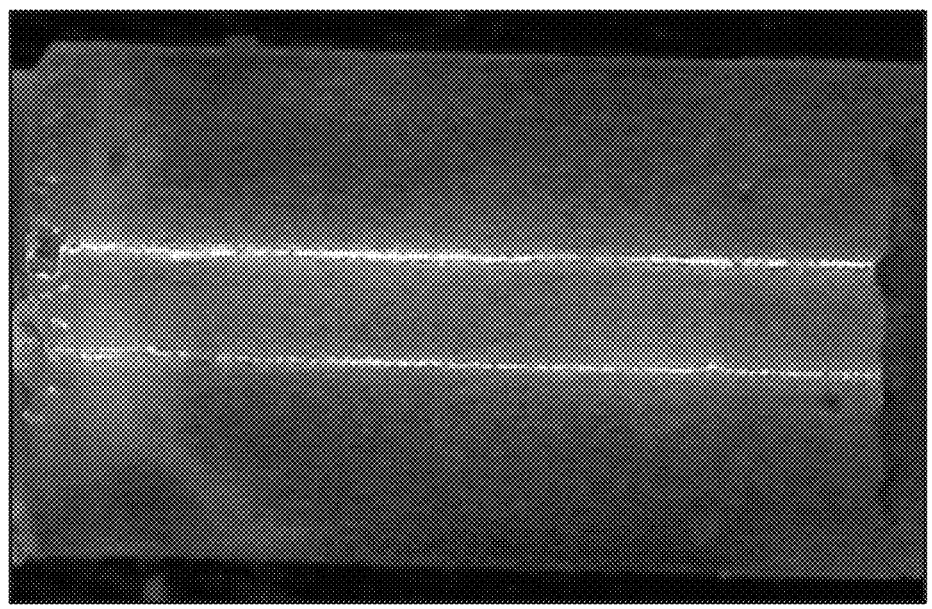

In some aspects, in addition to (or as an alternative to) the intensity or amount of emission light (e.g., second emission light 332) emitted by the interferent indicator 209 changing as degradation of the interferent indicator 209 increases, the absorption of the interferent indicator 209 may change (e.g., increase or decrease) as degradation of the interferent indicator 209 increases. In some aspects, the extent of the degradation of the interferent indicator 209 may correspond to the extent of degradation of the analyte indicator 207. Accordingly, in some aspects, the extent of the change in the absorption of the interferent indicator 209 (e.g., as measured by the amount of second excitation light 330 reflected from and not absorbed by the indicator element 106) may correspond to the change in the intensity or amount of emission light emitted by the analyte indicator 207. In some aspects, as degradation (e.g., oxidation) of the interferent indicator 209 increases, the color of the interferent indicator 209 (and, therefore, the color of the indicator element 106 including the interferent indicator 209) may change. For example, in some aspects, the color of the indicator element 106 may change from white with no oxidation, as shown in FIG. 16A, to yellow when oxidized, as shown in FIG. 16B. However, a change from white to yellow is not required, and, in some alternative aspects, different color changes may occur with degradation (e.g., white to yellow, white to orange, yellow to red, orange to brown, etc.). In some aspects, the change in the color of the interferent indicator 209 (and, therefore, the color of the indicator element 106 including the interferent indicator 209) may change the absorption of the interferent indicator 209 (and, therefore, the absorption of the indicator element 106 including the interferent indicator 209).

Figure 17A:
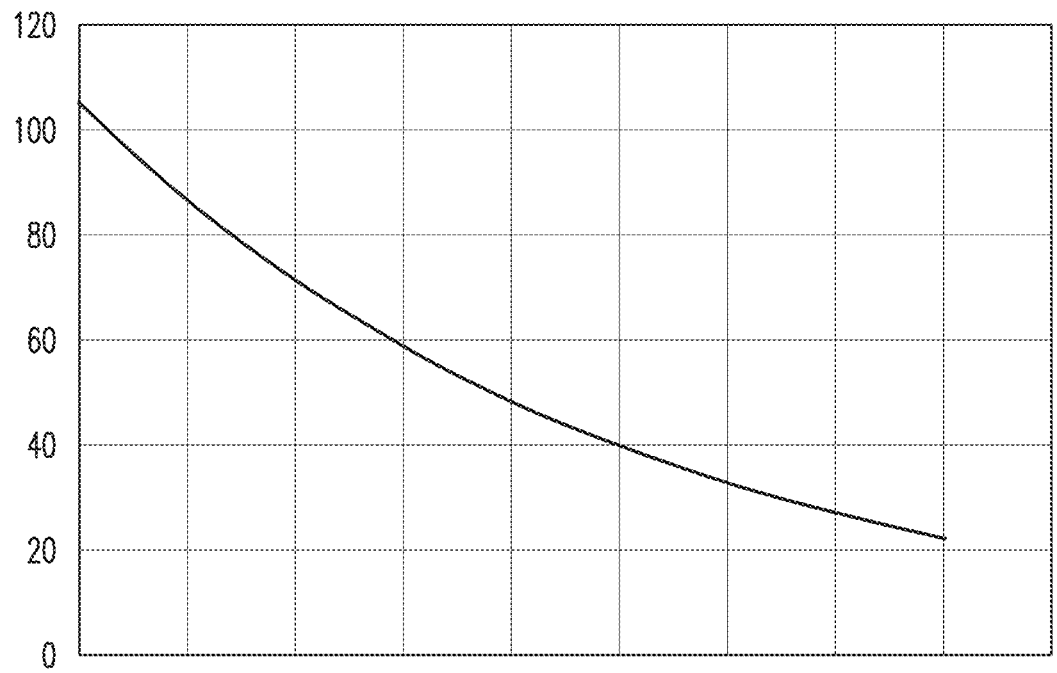
FIG. 17A illustrates a decrease in the intensity or amount of light emitted by an analyte indicator over time according to aspects of the present invention.
Figure 17B:
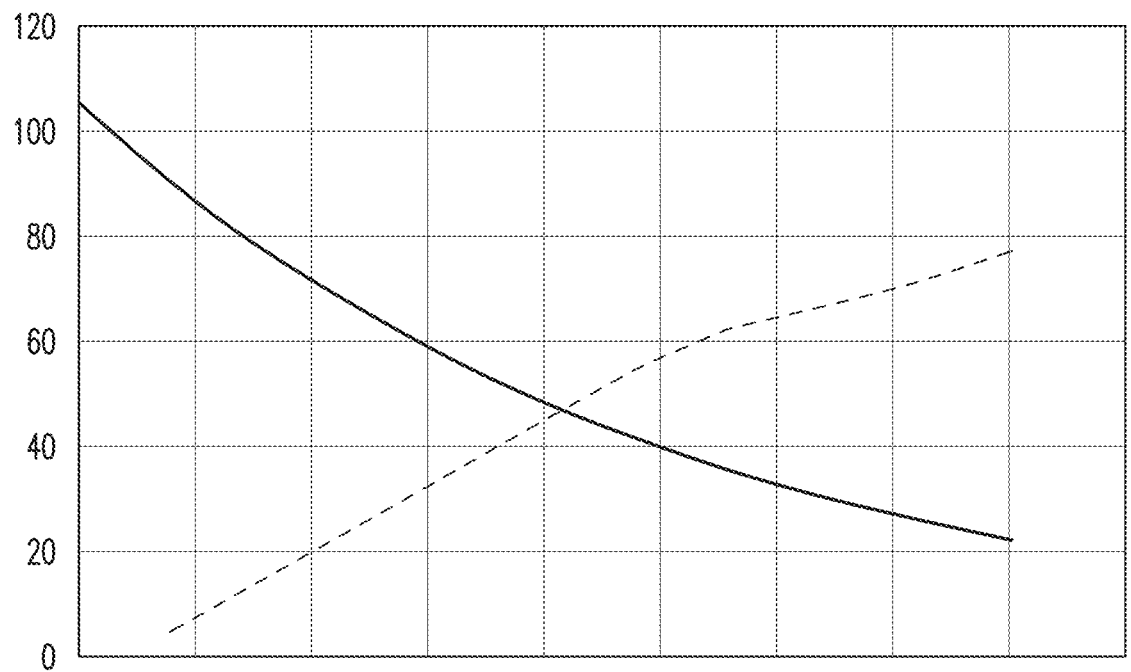
FIG. 17B illustrates an increase in the absorption of an indicator element over time and a decrease in the intensity or amount of the second excitation light reflected by the indicator element over time according to aspects of the present invention.

In some aspects, as shown by FIG. 17A, the intensity or amount of the emission light 331 emitted by the analyte indicator 207 may decrease over time (e.g., as degradation, such as oxidation, of the analyte indicator 207 increases). In some aspects, as shown by the yellow line of FIG. 17B, the absorption of the indicator element 106 may increase over time (e.g., as degradation, such as oxidation, of the interferent indicator 209 increases). In some aspects, as shown by the blue line of FIG. 17B, the intensity or amount of the second excitation light 330 reflected by the indicator element 106 may decrease over time (e.g., as degradation, such as oxidation, of the interferent indicator 209 increases). In some aspects, as shown in FIGS. 17A and 17B, the increase in the absorption of the indicator element 106 and the decrease in the intensity or amount of the second excitation light 330 reflected by the indicator element 106 may correspond to the decrease in the intensity or amount of emission light 331 emitted by the analyte indicator 207.

Figure 18:
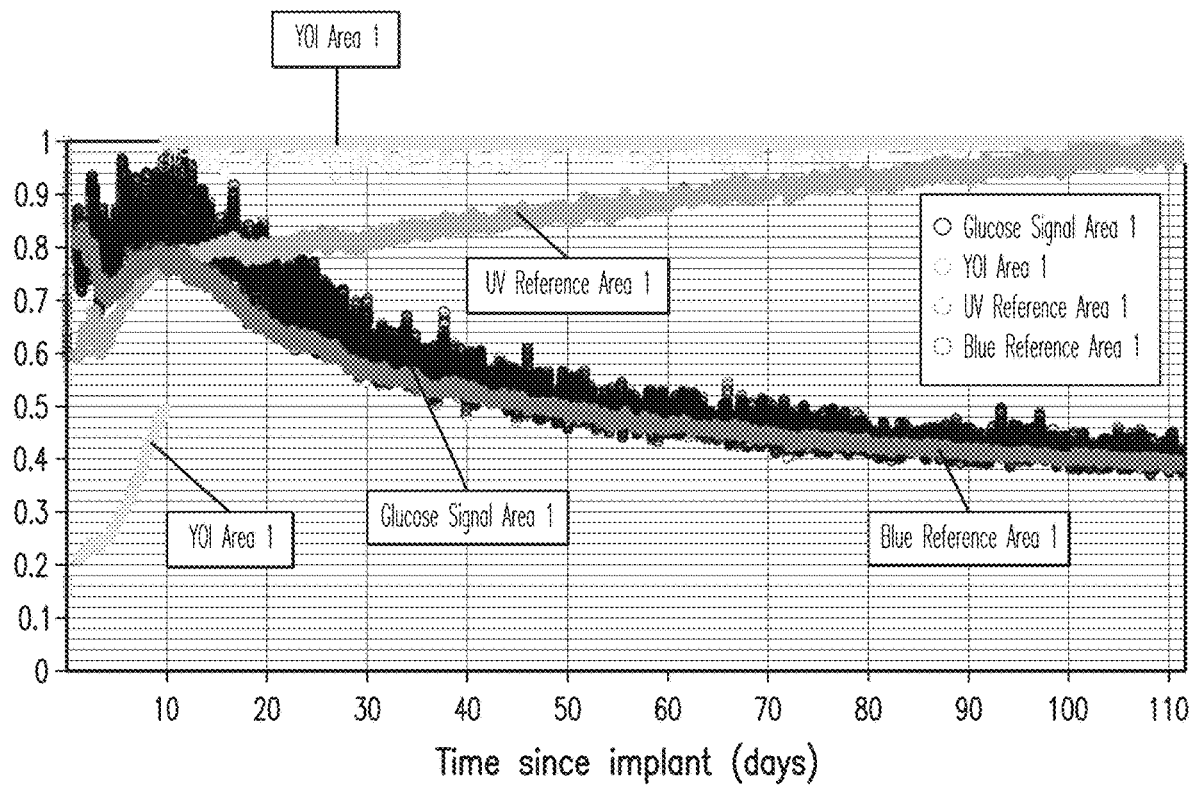
FIG. 18 is a graph illustrating experimental data from a clinical trial in which an analyte sensor 100 was implanted subcutaneously in the body of a living human

FIG. 18 illustrates a graph with experimental data from a clinical trial in which an analyte sensor 100 was implanted subcutaneously in the body of a living human. The glucose signal area of FIG. 18 illustrates analyte measurements indicative of amounts of the first emission light 331 emitted by the analyte indicator 207 and received by the one or more signal photodetectors 224 over time. As shown in FIG. 18, the analyte measurements may fluctuate initially (e.g., during a wound healing period after implantation of the analyte sensor 100 when there may be an increased amount of blood in the interstitial fluid in proximity to the sensor 100). The analyte measurements may then decrease over time due to an increase of an effect on the analyte indicator 207 (e.g., degradation of the analyte indicator 207).

The UV reference area of FIG. 18 illustrates first reference measurements indicative of amounts of first excitation light 329 reflected by the indicator element 106 and received by the one or more first reference photodetectors 226 over time. As shown in FIG. 18, the first reference measurements may fluctuate initially (e.g., during a wound healing period after implantation of the analyte sensor 100 when there may be an increased amount of blood in the interstitial fluid in proximity to the sensor 100).

The yellow oxidation indicator (YOI) area of FIG. 18 illustrates interferent measurements indicative of amounts of second emission light 332 emitted by the interferent indicator 209 and received by the one or more interferent photodetectors 228. In the experiment, the interferent measurements were cut off starting on day 10 but were expected to increase over time as degradation of the interferent indicator 209 increased. However, experimental data from in vitro oxidation studies have demonstrated an increase in the intensity or amount of the light emitted by the interferent indicator 209 over time as degradation of the interferent indicator 209 increased. Moreover, experimental data from in vitro oxidation studies have demonstrated that the increase in the intensity or amount of the light emitted by the interferent indicator 209 over time corresponds to the decrease in the intensity or amount of the light emitted by the analyte indicator 207 over time as degradation of the analyte indicator 207 increased.

The blue reference area of FIG. 18 illustrates second reference measurements indicative of amounts of second excitation light 330 reflected by the indicator element 106 and received by one or more photodetectors (e.g., the one or more signal photodetectors 224 of FIG. 2A or the one or more second reference photodetectors 230 of FIG. 2B) over time. As shown in FIG. 18, the second reference measurements may fluctuate initially (e.g., during a wound healing period after implantation of the analyte sensor 100 when there may be an increased amount of blood in the interstitial fluid in proximity to the sensor 100). The second reference measurements may then decrease over time as the absorption of the interferent indicator 209 (and therefore the absorption of the indicator element 106 that includes the interferent indicator 209) increases (e.g., due to degradation, such as oxidation, of the interferent indicator 209). As shown in FIG. 18, the decrease of the second reference measurements over time corresponds to the decrease of the analyte measurements over time. Thus, the experimental data confirms that measurements of the absorption of an indicator element 106 including the interferent indicator 209 can be used to calculate an effect on (e.g., degradation of) the analyte indicator 207 of the indicator element 106.

Figure 20:
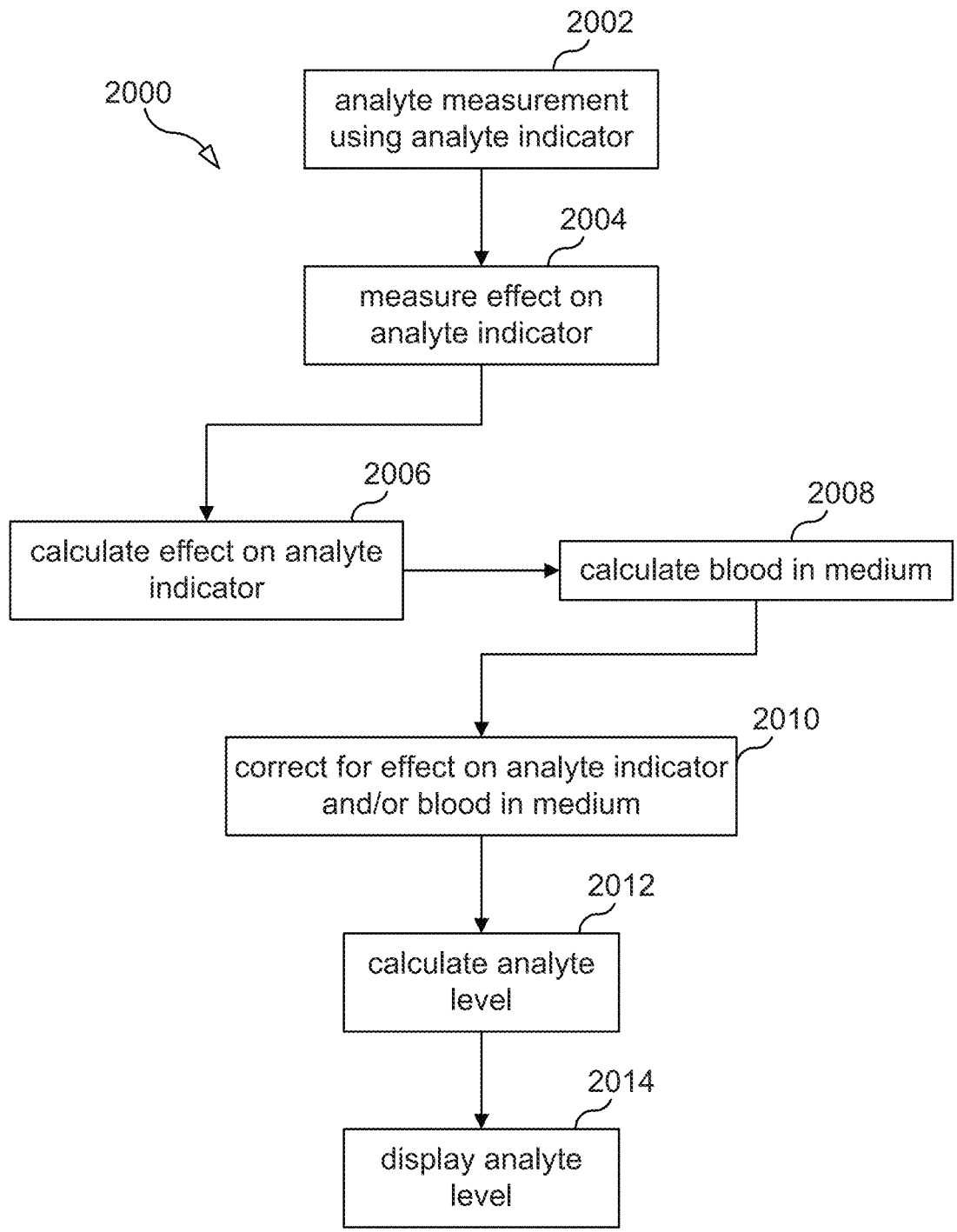
FIG. 20 is a flow chart illustrating a process for detecting and correcting for an effect on an analyte indicator embodying aspects of the present invention.

FIG. 20 illustrates non-limiting aspect of a process 2000 that may be performed by the analyte monitoring system 50. In some aspects, the process 2000 may detect and correct for an effect on the analyte indicator 207. In some aspects, the process 2000 may additionally or alternatively detect and correct for blood in the medium (e.g., interstitial fluid) in proximity to the analyte indicator 207.

In some aspects, the process 2000 may include a step 2002 in which the analyte monitoring system 50 performs an analyte measurement. In some aspects, step 2002 may include the analyte monitoring system 50 (e.g., the analyte sensor 100) using an analyte indicator 207 to generate an analyte measurement indicative of an amount or concentration of an analyte in a medium. In some aspects, the analyte measurement may vary in accordance with at least an effect on the analyte indicator 207. In some aspects, the effect on the analyte indicator 207 may be degradation of the analyte indicator 207. In some aspects, the degradation may be include oxidation-induced degradation, such as, for example, degradation by reactive oxygen species (ROS).

In some aspects, using the analyte indicator 207 to generate the analyte measurement in step 2002 may include using one or more first light sources 108 to emit first excitation light 329 to the analyte indicator 207 and using a signal photodetector 224 configured to receive first emission light 331 emitted by the analyte indicator 207 and output the analyte measurement. In some aspects, the analyte measurement may be indicative of an amount of the first emission light 331 received by the signal photodetector 224.

In some aspects, the step 2002 may include the analyte monitoring system 50 (e.g., the analyte sensor 100) using one or more first reference photodetectors 226 to receive an amount of the first excitation light 329 and output a first reference measurement indicative of the amount of the received first excitation light 329. In some aspects, the first excitation light 329 received by the first reference photodetector 226 may have been emitted by the one or more first light sources 108 and reflected from the first analyte indicator 207).

In some aspects, the step 2002 may include the transceiver 101 conveying and the analyte sensor 100 receiving an analyte measurement command. In some aspects, the step 2002 may include the analyte sensor 100, in response to receiving and decoding the analyte measurement command, using the first light source 108 to emit first excitation light 329 to the indicator element 106. The analyte indicator 207 of the indicator element 106 may receive the first excitation light 329 and emit first emission light 331. The signal photodetector 224 may receive the first emission light 331 and generate the analyte measurement signal based on the amount of first emission light 331 received by the signal photodetector 224. In some aspects, the reference photodetector 226 may receive first excitation light 329 that was reflected from the indicator element 106 and generate first reference measurement.

In some aspects, the process 2000 may include a step 2004 in which the analyte monitoring system 50 measures an effect on the analyte indicator 207. In some aspects, the step 2004 may include the analyte monitoring system 50 (e.g., the analyte sensor 100) using an interferent indicator 209 to generate a second reference measurement. In some aspects, the second reference measurement may be indicative of an absorption of the interferent indicator 209. In some aspects, the absorption of the interferent indicator 209 may vary in accordance with the effect on (e.g., degradation of) the analyte indicator 207. In some aspects, the second reference measurement generated in step 2004 may be in addition to the first reference measurement, which may be generated in step 2002 and may be indicative of the amount of first excitation light 329 received by the one or more first reference photodetectors 226). However, the second reference measurement may be generated in step 2004 even in aspects in which the first reference measurement is not generated in step 2002.

In some aspects, using the interferent indicator 209 to generate the second reference measurement in step 2004 may include using one or more second lights sources 227 to emit second excitation light 330 to the interferent indicator 209. In some aspects, using the interferent indicator 209 to generate the second reference measurement may include using one or more photodetectors (e.g., one or more signal photodetectors 224 as shown in FIG. 2A or one or more second reference photodetectors 230 as shown in FIG. 2B) to receive an amount of the second excitation light 330 and output the second reference measurement. In some aspects, the second reference measurement may be indicative of the amount of the received second excitation light 330, and the amount of the received second excitation light 330 may be indicative of the absorption of the interferent indicator 209.

In some aspects, the step 2004 may include (in addition or as an alternative to generating the second reference measurement) the analyte monitoring system 50 (e.g., the analyte sensor 100) using the interferent indicator 209 to generate an interferent measurement. In some aspects, generating an interferent measurement may include using one or more second lights sources 227 to emit second excitation light 330 to the interferent indicator 209. In some aspects, generating an interferent measurement may include using an interferent photodetector 228 to receive second emission light 332 emitted by the interferent indicator 209 and output an interferent measurement indicative of an amount of the second emission light 332 received by the interferent photodetector 228. In some aspects, the second emission light 332 may vary in accordance with the effect on (e.g., degradation of) the analyte indicator 331.

In some aspects, the step 2004 may include the transceiver 101 conveying and the analyte sensor 100 receiving an interferent measurement command. In some aspects, the step 2004 may include the analyte sensor 100, in response to receiving and decoding the interferent measurement command, measures the effect on the analyte indicator 207. In some aspects, measuring the effect on the analyte indicator may include using the second light source 227 to emit second excitation light 330 to the indicator element 106. The interferent indicator 209 of the indicator element 106 may receive the second excitation light 330 and emit second emission light 332. The interferent photodetector 228 may receive the second emission light 332 and generate the interferent measurement signal based on the amount of second emission light 332 received by the interferent photodetector 228. The signal photodetector 224 (and/or the second reference photodetector 230) may receive second excitation light 330 that was reflected from the indicator element 106 and generate the second reference signal. In some alternative aspects, the step 2004 may not include the transceiver 101 conveying and the analyte sensor 100 receiving an interferent measurement command, and the analyte sensor 100 may measures the effect on the analyte indicator 207 in response to receiving and decoding an analyte measurement command (instead of in response to receiving and decoding an interferent measurement command).

In some aspects, step 2002 may be performed before step 2004. In some alternative aspects, steps 2002 and 2004 may be performed simultaneously, and the analyte sensor 100 may use the first and second light sources 108, 227 to emit simultaneously the first and second excitation lights 329, 330 to the indicator element 106. In some other alternative aspects, step 2004 may be performed before step 2002.

In some aspects, the process 2000 may include a step 2006 in which the analyte monitoring system 50 (e.g., the transceiver 101) calculates the effect on the analyte indicator 207 (e.g., the extent to which the analyte indicator 207 has degraded). In some aspects, the step 2006 may include the analyte sensor 100 conveying and the transceiver 101 receiving sensor data. In some aspects, the sensor data may include one or more of the analyte measurement, the first reference measurement, the interferent measurement, the second reference measurement, and a temperature measurement. In some alternative aspects, the step 2002 may include the analyte sensor 100 conveying and the transceiver 101 receiving sensor data (e.g., the analyte measurement, the first reference measurement, and/or the temperature measurement), and/or the step 2004 may include the analyte sensor 100 conveying and the transceiver 101 receiving sensor data (e.g., the interferent measurement and/or the second reference measurement).

In some aspects, the analyte monitoring system 50 (e.g., the transceiver 101) may calculate the effect on the analyte indicator 207 in step 2006 based at least on one or more measurements generated in step 2004 (e.g., the second reference measurement indicative of the absorption of the interferent indicator 209 and/or the interferent measurement indicative of the emission of the interferent indicator 209). In some aspects, the system 50 may calculate the effect on the analyte indicator 106 based on a change in the absorption of the analyte indicator 106, which may be indicated by the second reference measurement. In some aspects, the system 50 may calculate the effect on the analyte indicator 207 based on a ratio of the interferent measurement and the second reference measurement. In some aspects, the step 2006 may additionally or alternatively include the system 50 using one or more previous interferent measurements and/or one or more previous calculations of the effect on the analyte indicator 207 to calculate the effect (e.g., the current effect) on the analyte indicator 207.

In some aspects, the process 2000 may include a step 2008 in which the analyte monitoring system 50 (e.g., the transceiver 101) calculates an amount of blood in the medium (e.g., interstitial fluid (ISF)). In some aspects, the amount of blood in the medium may be calculated in step 2008 based on the second reference measurement, which may be indicative of an amount of received second excitation light 330. In some aspects, the second reference measurement may be indicative of an absorption of the interferent indicator 209. In some aspects, the amount of blood in the medium may additionally or alternatively be calculated based on the first reference measurement, which may be indicative of the amount of received first excitation light 329. In some aspects, the amount of blood in the medium may be calculated in step 2008 based on at least a ratio of the first and second reference measurements. In some aspects, the amount of blood in the medium may additionally or alternatively be calculated in step 2008 based on the interferent measurement, which may be indicative of the amount of received second emission light 332.

Figure 19A:
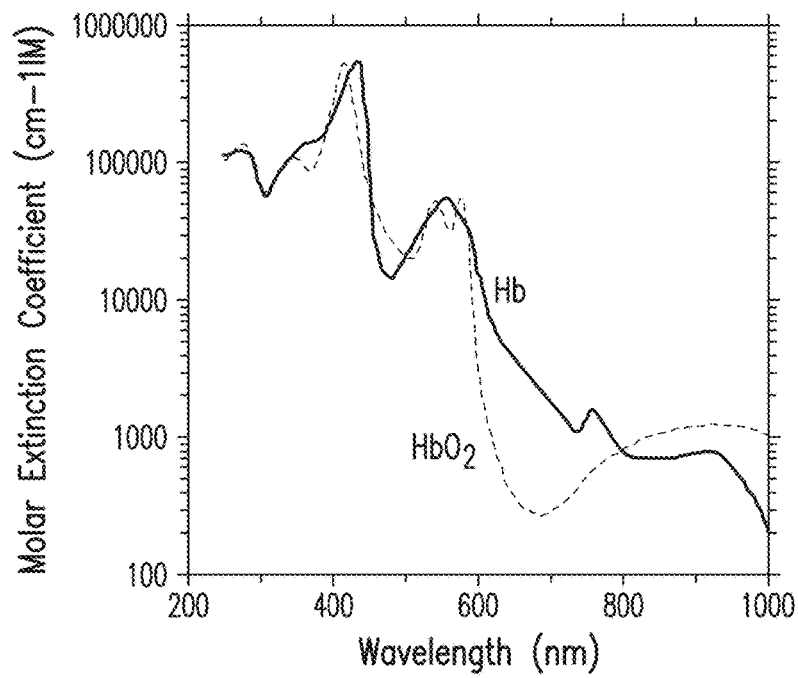
FIG. 19A is a graph illustrating oxy-hemoglobin and de-oxy hemoglobin extinction coefficients at different wavelengths.
Figure 19B:
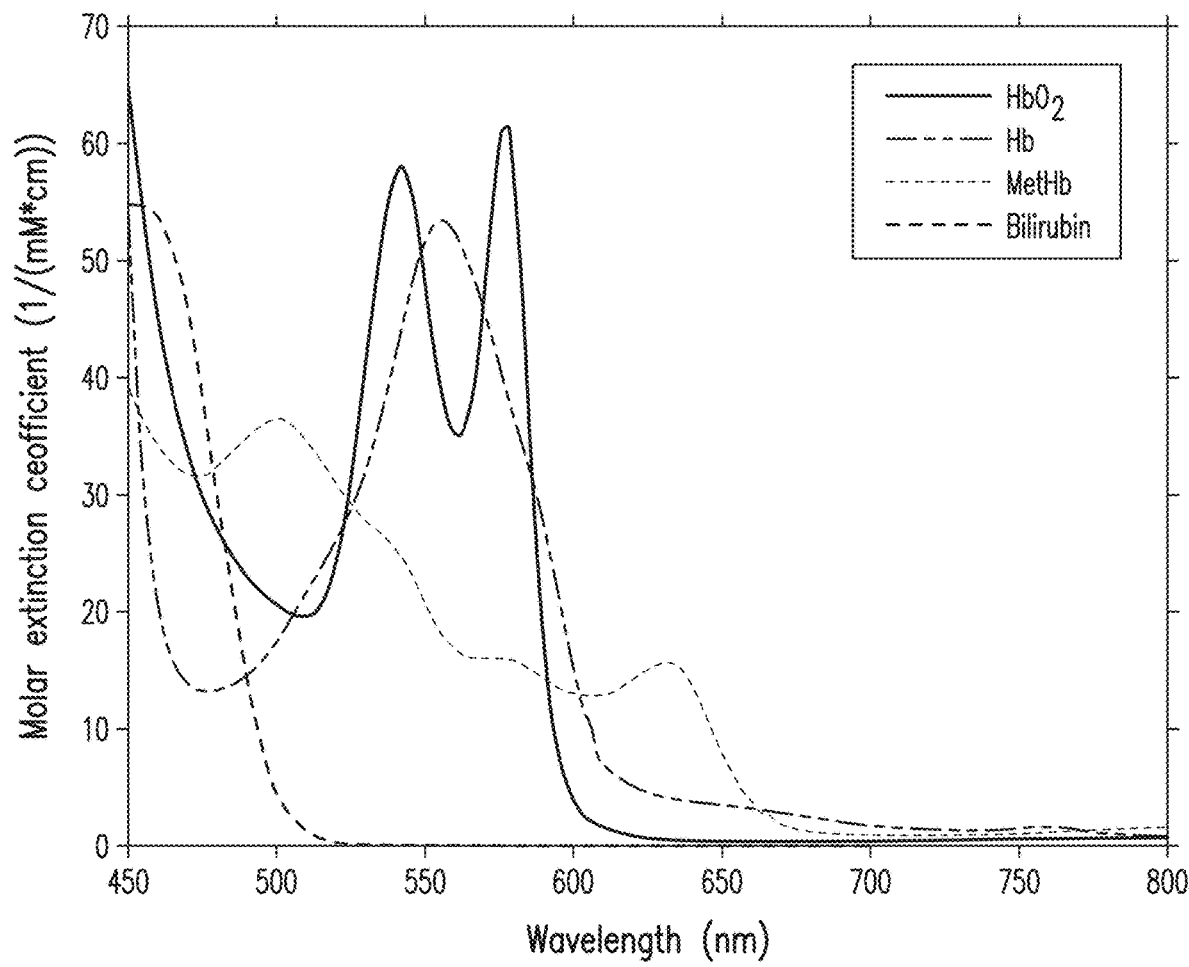
FIG. 19B is a graph illustrating oxy-hemoglobin, de-oxy hemoglobin, methemoglobin, and bilirubin extinction coefficients at different wavelengths.

FIG. 19A is a graph illustrating oxy-hemoglobin ($HbO_2$) and de-oxy hemoglobin (Hb) extinction coefficients at different wavelengths. FIG. 19B is a graph illustrating oxy-hemoglobin ($HbO_2$), de-oxy hemoglobin (Hb), methemoglobin (MetHb), and bilirubin extinction coefficients at different wavelengths. In some aspects, in the step 2008, the system 50 may use the known extinction coefficients of one or more of oxy-hemoglobin ($HbO_2$), de-oxy hemoglobin (Hb), methemoglobin (MetHb), and bilirubin at the wavelengths of one or more of the first excitation light 329 (e.g., 380 nm) and the second excitation light 330 (e.g., 470 nm) along with one or more of the first and second reference measurements to calculate the amount of blood in the medium in proximity to the analyte sensor 100.

In some aspects, the process 2000 may include a step 2010 in which the analyte monitoring system 50 (e.g., the transceiver 101) corrects for an effect on the analyte indicator 207 and/or blood in the medium (e.g., ISF). In some aspects, the step 2010 may include the analyte monitoring system 50 (e.g., the transceiver 101) adjusting a conversion function. In some aspects, the conversion function may be used to calculate an analyte level based on the analyte measurement. In some aspects, the conversion function may be adjusted in step 2010 based on the calculated effect on the analyte indicator 207 (e.g., calculated in step 2006). In some aspects, the conversion function may additionally or alternatively be adjusted in step 2010 based on the calculated blood in the medium (e.g., calculated in step 2008). In some aspects, adjusting the conversion function may include adjusting one or more parameters of the conversion function.

In some aspects, the process 2000 may include a step 2012 in which the analyte monitoring system 50 (e.g., the transceiver 101) calculates an analyte level (e.g., an analyte concentration). In some aspects, the step 2012 may include the analyte monitoring system 50 (e.g., the transceiver 101) using the adjusted conversion function and the analyte measurement. In some aspects, the system 50 may additionally use the temperature measurement to calculate the analyte level.

In some aspects, the process 2000 may include a step 2014 in which the analyte monitoring system 50 displays the calculated analyte level. In some aspects, to display the calculated analyte level in step 2014, the system 50 may display the analyte level on the display 924. In some aspects, to display the calculated analyte level in step 2014, the system 50 may additionally or alternatively convey the calculated analyte level to the display device 107, and the display device 107 may additionally or alternatively convey the calculated analyte level.

In some aspects, the analyte sensor 100 of the analyte monitoring system 50 may be a fully implantable sensor and may utilize a fluorescent, boronic acid glucose-binding moiety as the analyte indicator 207 for the measurement of glucose. In some aspects, the binding affinity of this analyte indicator 207 may be specific for glucose but may also be susceptible to oxidative de-boronation through localized Reactive Oxygen Species (ROS) (e.g., hydrogen peroxide ($H_2O_2$)) present in the interstitial space. In some aspects, the analyte sensor 100 may rely on calibration updates to characterize the rate of oxidation from localized in vivo concentrations of ROS. In some aspects, utilizing the indicator element 106 that includes the interferent indicator 209 to measure ROS concentration may enable reduction of the calibration frequency.

Figure 22:
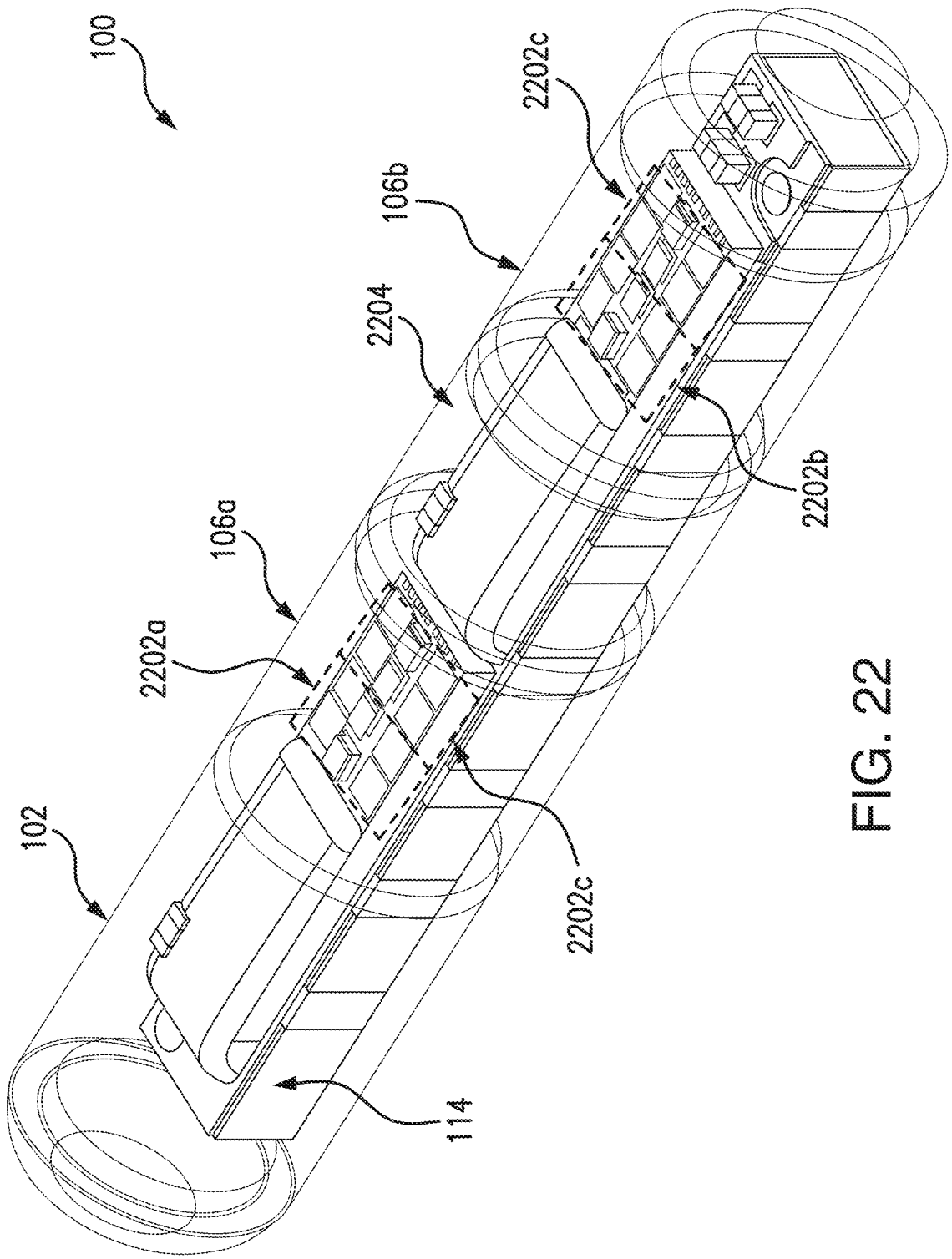
FIG. 22 shows an analyte sensor include multiple sensing areas and multiple indicator elements according to some aspects.

In some aspects, as shown in FIG. 22, the analyte sensor 100 may include multiple sensing areas 2202 (e.g., sensing areas 2202a, 2202b, 2202c, and 2202d). In some aspects, the sensing areas 2202 may each include a measurement electronics (e.g., optical measurement electronics). In some aspects, the measurement electronics in each of the sensing areas 2202 may include one or more light sources (e.g., a light sources 108 and 227) and/or one or more photodetectors (e.g., photodetectors 224, 226, 228, and/or 230). In some aspects, the analyte sensor 100 may include first and second substrates 112, sensing areas 2202a and 2202c may be on the first substrate 112, and sensing areas 2202b and 2202d may be on the second substrate 112. In some aspects, the sensing areas 2202a and 2202c may be long end distal (LED) and long end central (LEC) sensing areas of the analyte sensor 100, respectively, and the sensing areas 2202b and 2202d may be short end central (SEC) and short end distal (SED) sensing areas of the analyte sensor, respectively.

In some aspects, as shown in FIG. 22, the analyte sensor 100 may include one or more indicator elements 106 (e.g., indicator elements 106a and 106b), which may be, for example, one or more hydrogels on the sensor housing 102. In some aspects, as shown in FIGS. 2A and 2B, the one or more indicator elements 106 may each include an analyte indicator 207 and an interferent indicator 209. In some aspects, the analyte sensor 100 may use the analyte indicator 207 to measure the presence, amount, and/or concentration of an analyte (e.g., glucose, oxygen, cardiac markers, low-density lipoprotein (LDL), high-density lipoprotein (HDL), or triglycerides). In some aspects, the analyte sensor 100 may use the interferent indicator 209 to measure ROS induced signal degradation. In some aspects, in the one or more indicator elements 106, the analyte indicator 207 and the interferent indicator 209 may be copolymerized into a single biocompatible hydrogel. In some aspects, the analyte indicator 207 and the interferent indicator 209 may have negligible spectral overlap and undergo similar degradation (e.g., similar degradation of boronic acids) in vivo.

Figure 21A:
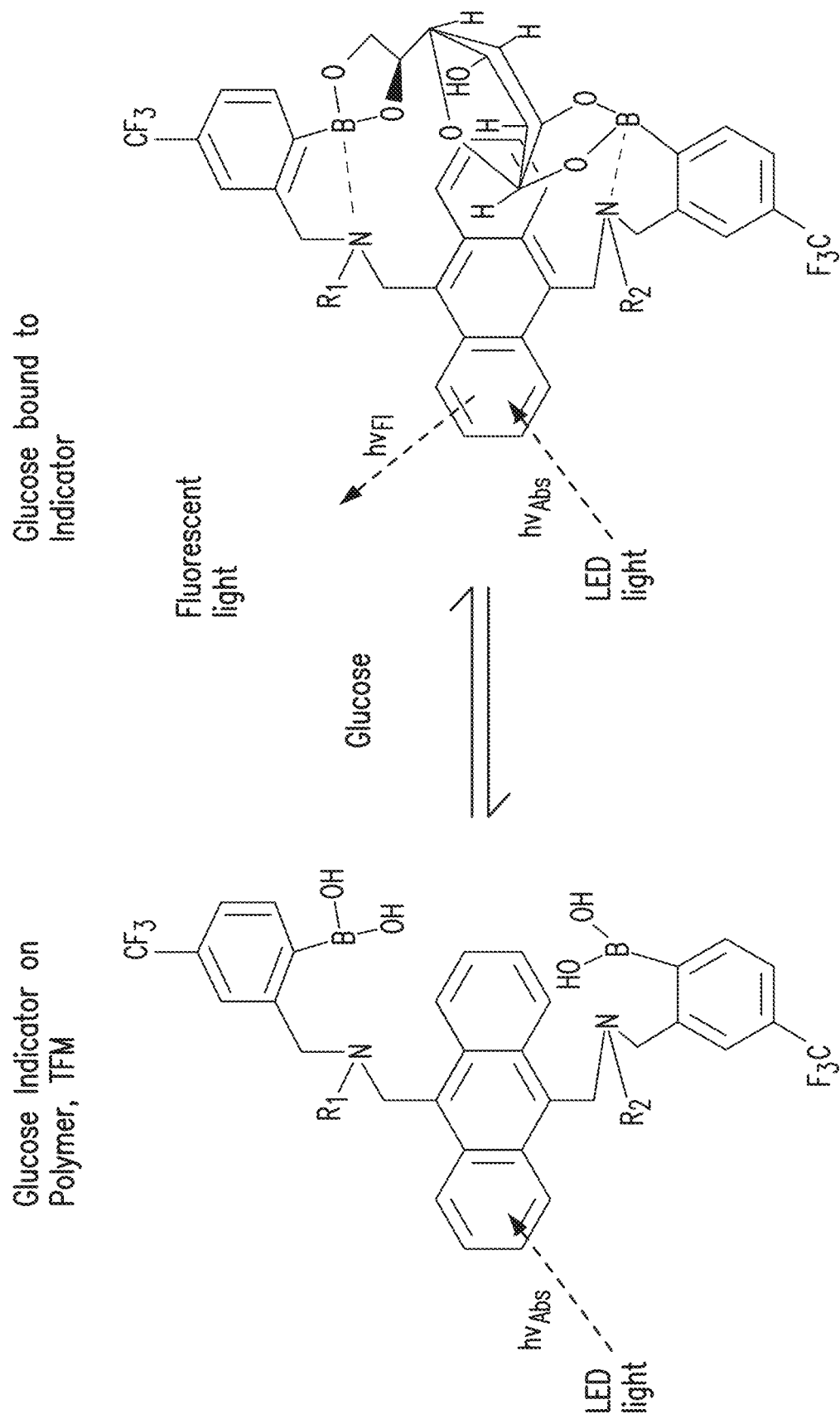
FIGS. 21A and 21B show the chemical structures of the analyte indicator and interference indicator, respectively, according to some aspects.
Figure 21B:
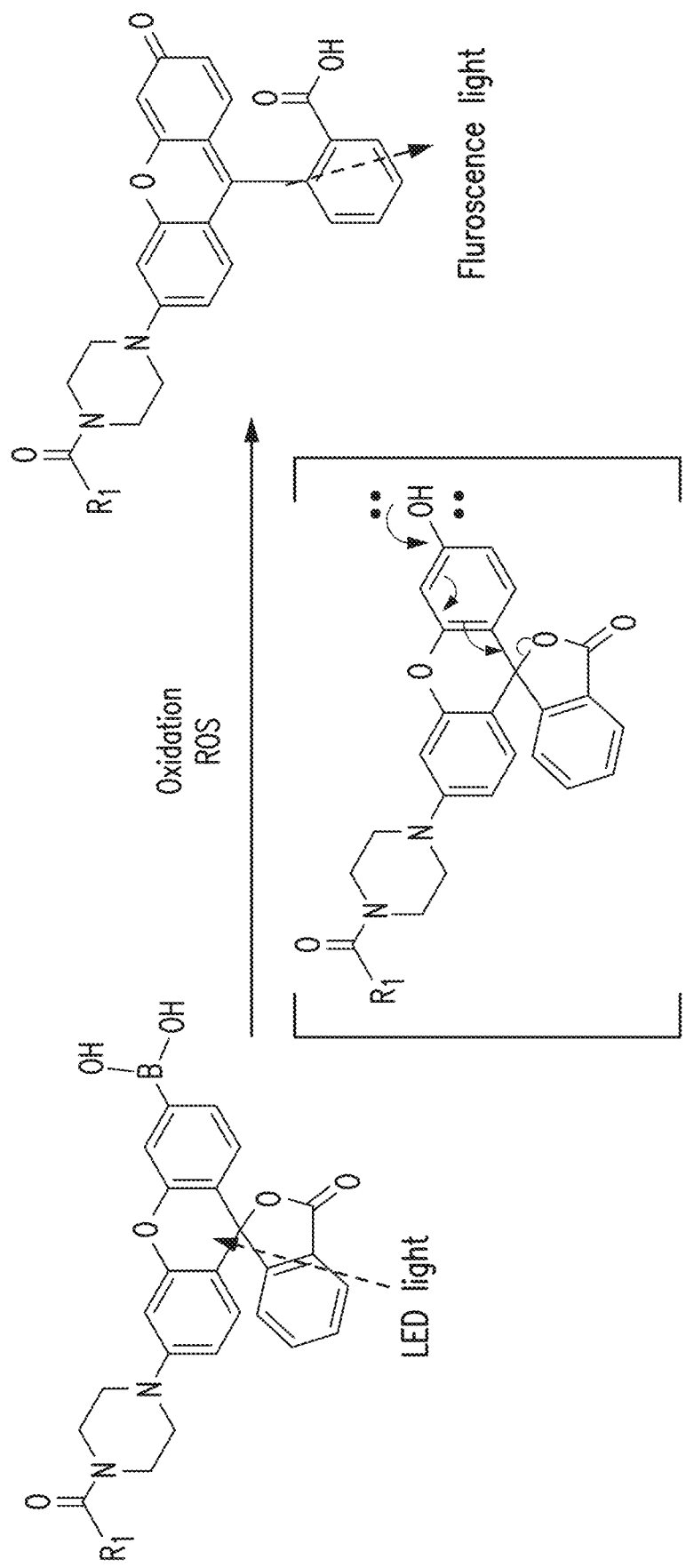

In some aspects, the analyte indicator 207 of the one or more indicator elements 106 may be, for example, TFM. In some aspects, the analyte indicator 207 may have the chemical structure shown in FIG. 21A. In some aspects, as shown in FIG. 21A, an analyte (e.g., glucose) may bind reversibly to the analyte indicator 202, the analyte indicator 207 to which the analyte is bound may emit first emission light 331 (e.g., fluorescent light) when irradiated by the first excitation light 329, and the analyte indicator 207 to which the analyte is not bound may not emit light (or emit only a small amount of light) when irradiated by the first excitation light 329. In some aspects, as shown in FIG. 21B, oxidation of the interferent indicator 209 cause the interferent indicator 209 to emit second emission light 332 (e.g., when irradiated by the second excitation light 330). In some aspects, oxidation of the interferent indicator 209 may additionally or alternatively cause the absorption of the interferent indicator 209 (e.g., absorption of the second excitation light 330 by the interferent indicator 209) to change. In some aspects, as shown in FIG. 22, one or more sensing areas 2202 (e.g., sensing areas 2202a and 2202c) may interact with (e.g., emit first and second excitation lights 329 and 330 to and measure first and second emission lights 331 and 332 emitted by) a first indicator element 106a, and one or more different sensing areas 2202 (e.g., sensing areas 2202b and 2202d) may interact with a second indicator element 106b.

In some aspects, with the interferent indicator 209 in the one or more indicator elements 106, the analyte sensor 100 may be configured to measure in vivo signal degradation and signal changes resulting from ROS, which may reduce the frequency with which calibration based on reference analyte measurements (e.g., finger stick blood glucose measurements).

In some aspects, the analyte sensor 100 may sense an analyte (e.g., glucose) in each of the multiple sensing areas 2202 (e.g., each of the sensing areas 2202a-2022d). In some aspects, the multiple sensing areas 2202 may be redundant sensing areas. In some aspects, in each of the sensing areas 2202, the analyte indicator 207 may be excited by first excitation light 329 emitted by a light source 108 (e.g., a UV LED), and the interferent indicator 209 may be excited by second excitation light 330 emitted by a light source 227 (e.g., a blue LED). In some aspects, the first excitation light 329 and the first emission light 331 emitted by the analyte indicator 207 may be measured by one or more first reference photodetectors 226 (e.g., one or more UV filter coated photodiodes) and one or more signal photodetectors 224 (e.g., one or more blue filter coated photodiodes) respectively. In some aspects, the second excitation light 330 may be measured by one or more signal photodetectors 224 (see FIG. 2A) or one or more second reference photodetectors 230 (see FIG. 2B), which may be, for example, one or more blue filter coated photodiodes. In some aspects, the second emission light 332 emitted by the interferent indicator 209 may be measured by one or more interferent photodetector 228 (e.g., one or more yellow filter coated photodiodes).

In some aspects, as shown in FIG. 22, the analyte sensor 100 may include one or more drug-eluting polymer matrices 2204 on all or a portion of an external surface of the sensor housing 102. In some aspects, one or more therapeutic agents may be dispersed within the one or more drug eluting polymer matrices 2204. In some aspects, the one or more therapeutic agents may reduce or stop the migration of neutrophils from entering the space in which the analyte sensor 100 has been implanted and, thus, reduce or stop the production of hydrogen peroxide and fibrotic encapsulation. Accordingly, in some aspects, the one or more therapeutic agents may reduce deterioration of the one or more indicator elements 106 (e.g., indicator elements 106a and 106b). In some aspects, the one or more therapeutic agents, which may be dispersed within the drug eluting polymer matrix 2204, may include one or more anti-inflammatory drugs, such as, for example, non-steroidal anti-inflammatory drug (e.g., acetylsalicylic acid (aspirin) and/or isobutylphenylpropanoic acid (ibuprofen)). In some aspects, the one or more therapeutic agents dispersed within the drug-eluting polymer matrix may include one or more glucocorticoids. In some non-limiting embodiments, the one or more therapeutic agents may include one or more of dexamethasone, triamcinolone, betamethasone, methylprednisolone, beclometasone, fludrocortisone, derivatives thereof, and analogs thereof. In some aspects, the one or more therapeutic agents may reduce the production of hydrogen peroxide by neutrophils and macrophages.

Figure 23:
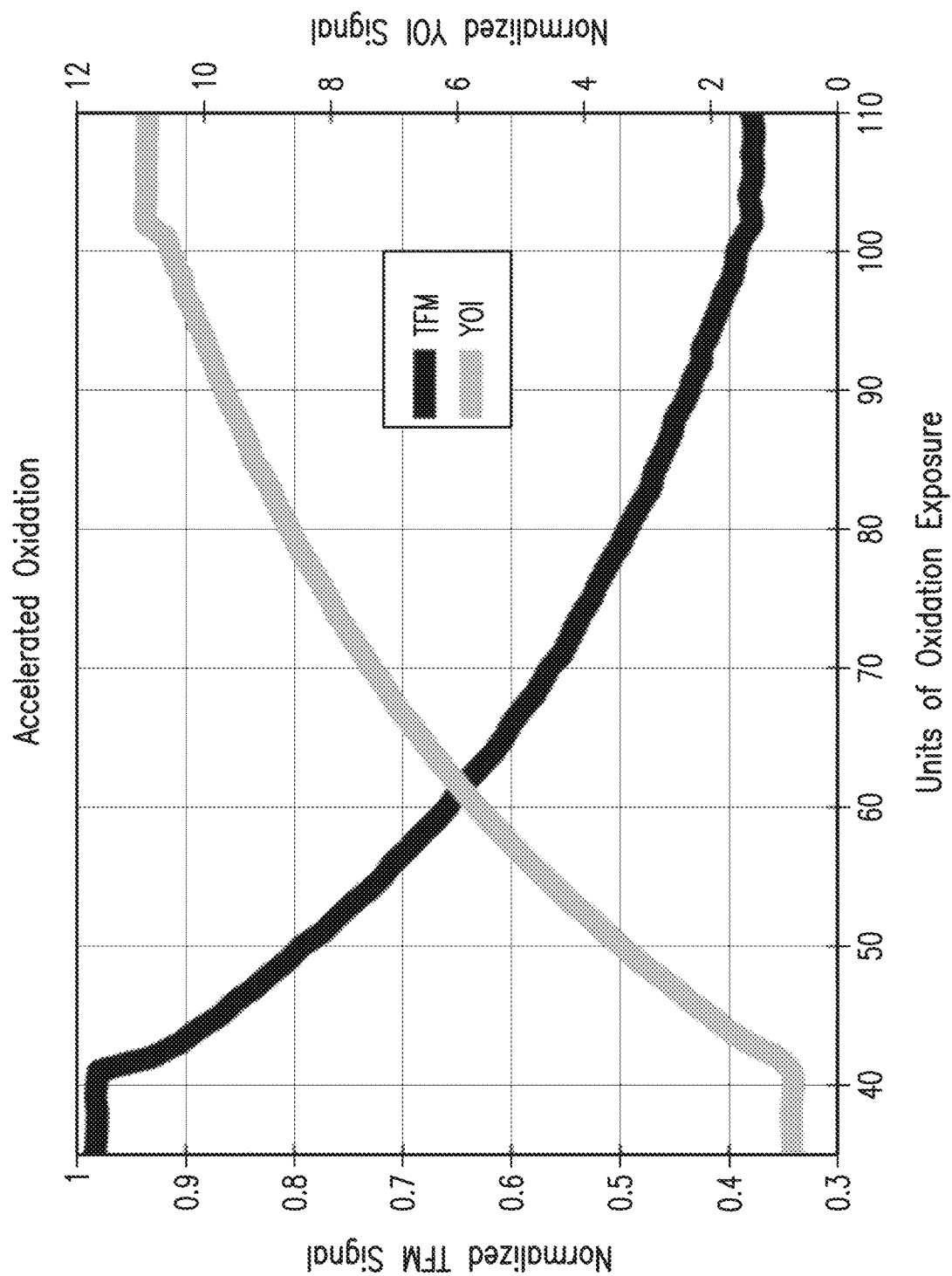
FIG. 23 shows, as oxidation increases, the first emission light emitted by the analyte indicator decreasing and the second emission light emitted by the interferent indicator increasing with similar degradation kinetics according to some aspects.
Figure 24A:
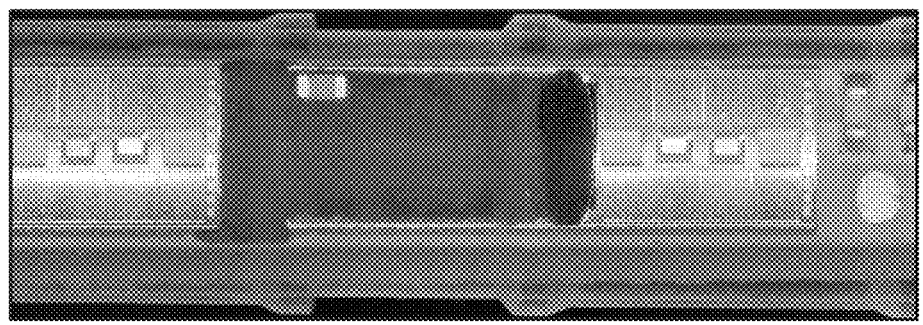
FIGS. 24A-24D show optical and fluorescence images of the analyte sensor after localized oxidation according to some aspects.
Figure 24B:
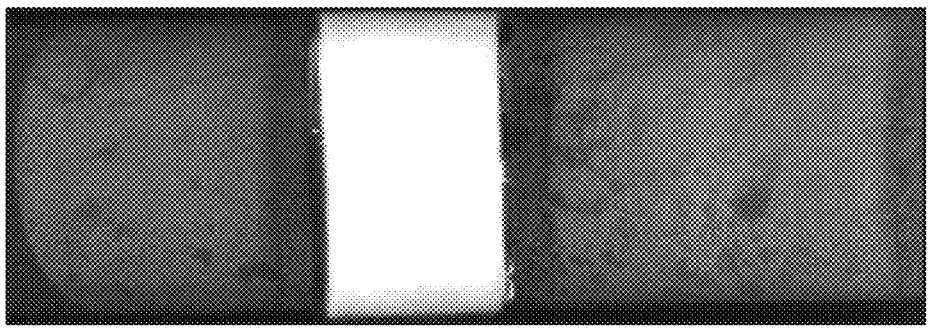
Figure 24C:
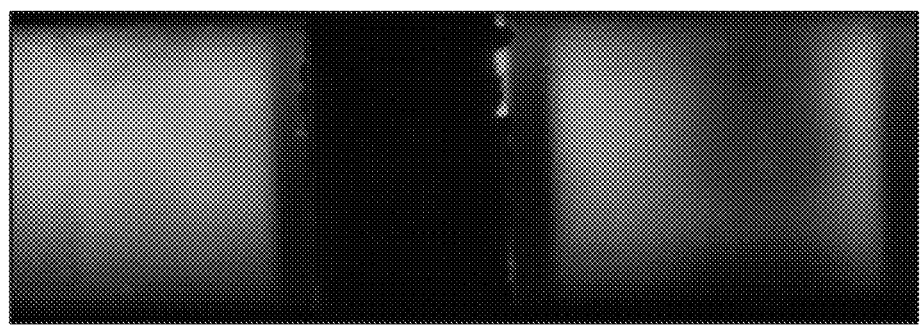
Figure 24D:
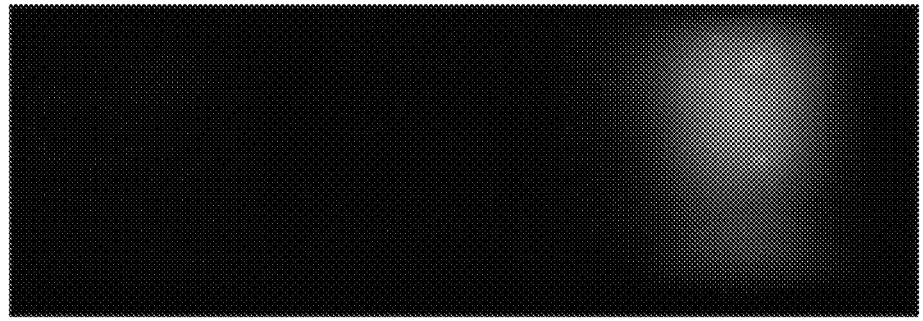
Figure 25A:
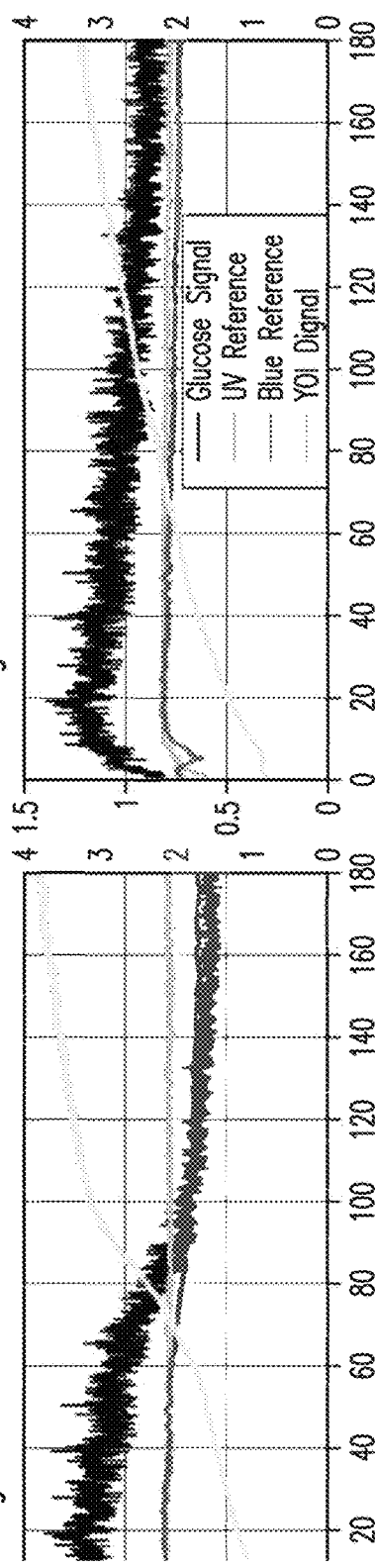
FIGS. 25A-25D show in vivo measurements from the different sensing areas of the analyte sensor shown in FIG. 22 according to some aspects.
Figure 25B:
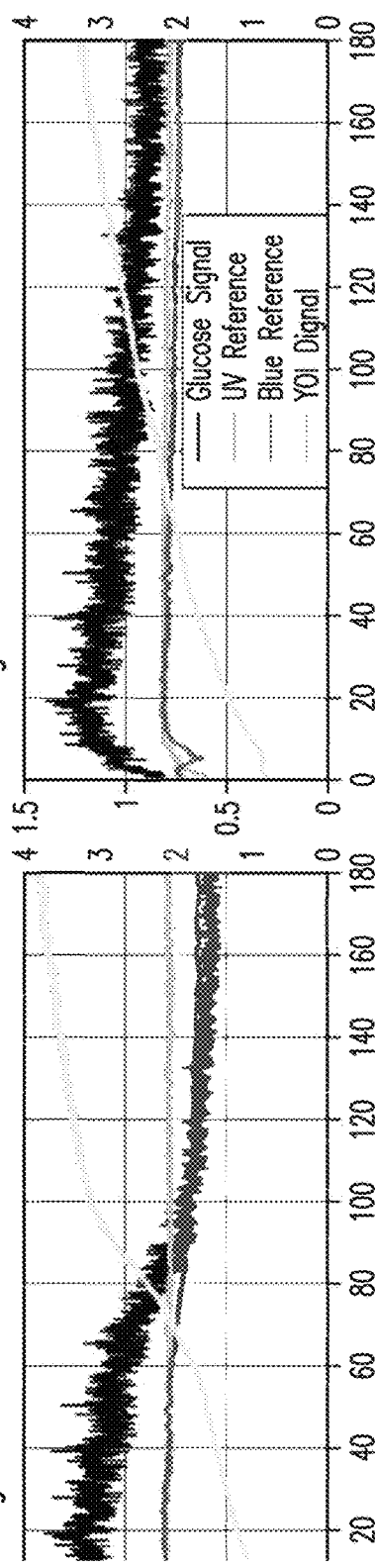
Figure 25C:
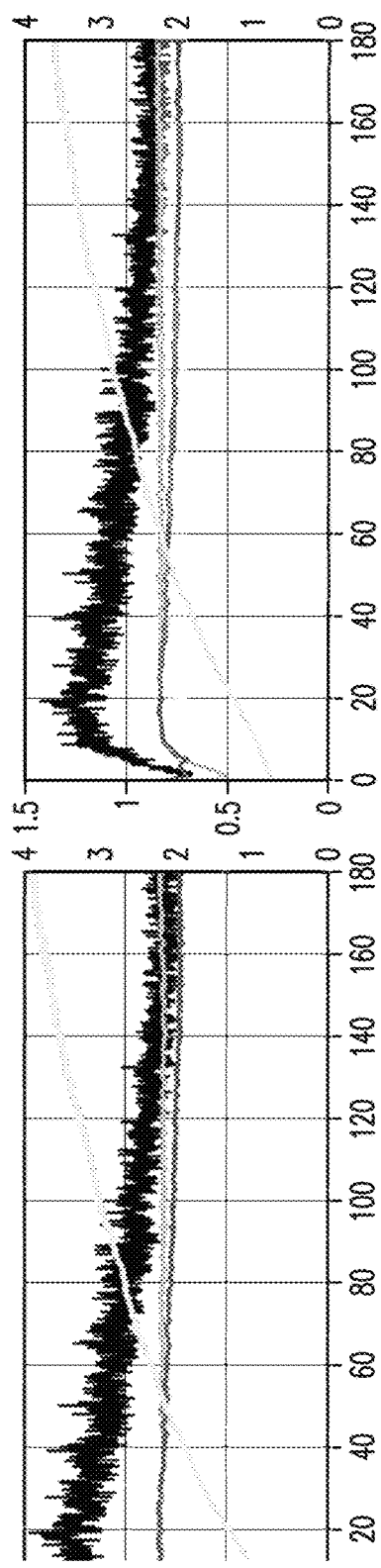
Figure 25D:
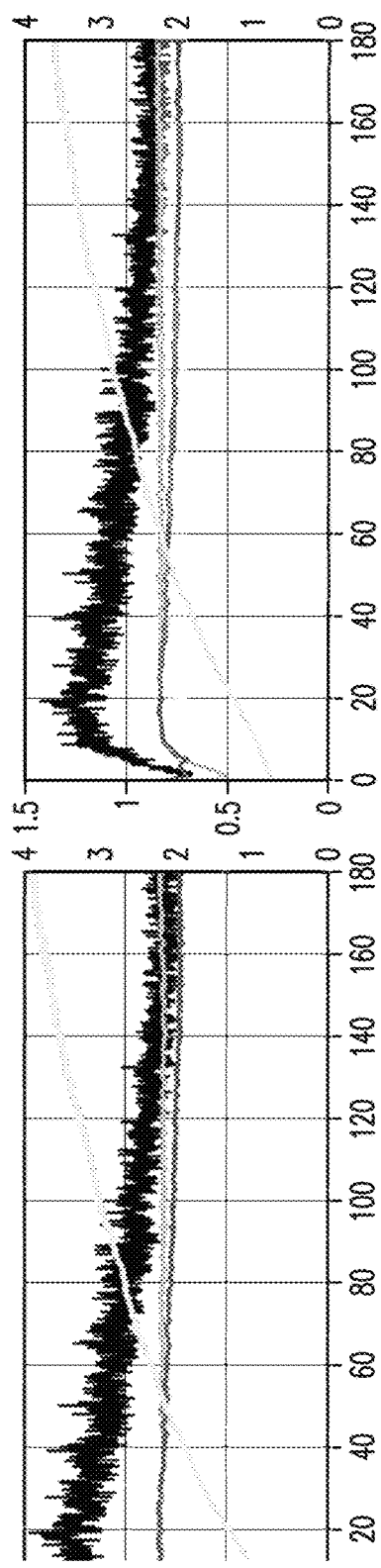

In-vitro oxidation experiments were performed to study the response of the analyte indicator 207 and the interferent indicator 209 to oxidation. As shown in FIG. 23, as oxidation increases, the first emission light 331 emitted by the analyte indicator 207 decreases and the second emission light 332 emitted by the interferent indicator 209 increases with similar degradation kinetics. FIGS. 24A-24D show optical and fluorescence images of the analyte sensor 100 after localized oxidation. FIGS. 24A and 24B show the underlying sensor optics and a bright field image of the analyte sensor 100, respectively. FIG. 24C shows fluorescence imaging of the analyte indicator 207 with a localized decrease in fluorescence due to localized oxidation near the bottom of the analyte indicator 207, and FIG. 24D shows fluorescence imaging of the interferent indicator 209 with a corresponding localized increase in fluorescence due to the localized oxidation near the bottom of the interferent indicator 209. Thus, the fluorescence imaging shown in FIGS. 24C and 24D demonstrate that a decrease in the first emission light 331 emitted by the analyte indicator 207 due to localized oxidation is spatially correlated with an increase in the second emission light 332 emitted by the interferent indicator 209.

In a non-limiting example, after informed consent, clinical feasibility evaluations were performed in 10 adults with type 1 diabetes up to 365 days. Accuracy was evaluated against finger stick glucose measurements during home use. Measurements showed the benefit of assessing localized oxidation to determine the transient de-boronation of the analyte indicator chemistry. FIGS. 25A-25D show in vivo measurements from the sensing areas 2202a, 2202c, 2202b, and 2202d, respectively, of the analyte sensor 100 shown in FIG. 22. In some aspects, the sensing areas 2202a and 2202c may be long end distal (LED) and long end central (LEC) sensing areas of the analyte sensor 100, respectively, and the sensing areas 2202b and 2202d may be short end central (SEC) and short end distal (SED) sensing areas of the analyte sensor, respectively. As shown in FIGS. 25A-25D, the measurements may include measurements of the first and second excitation lights 329 and 330 and the first and second emission lights 331 and 332.

Figure 26A:
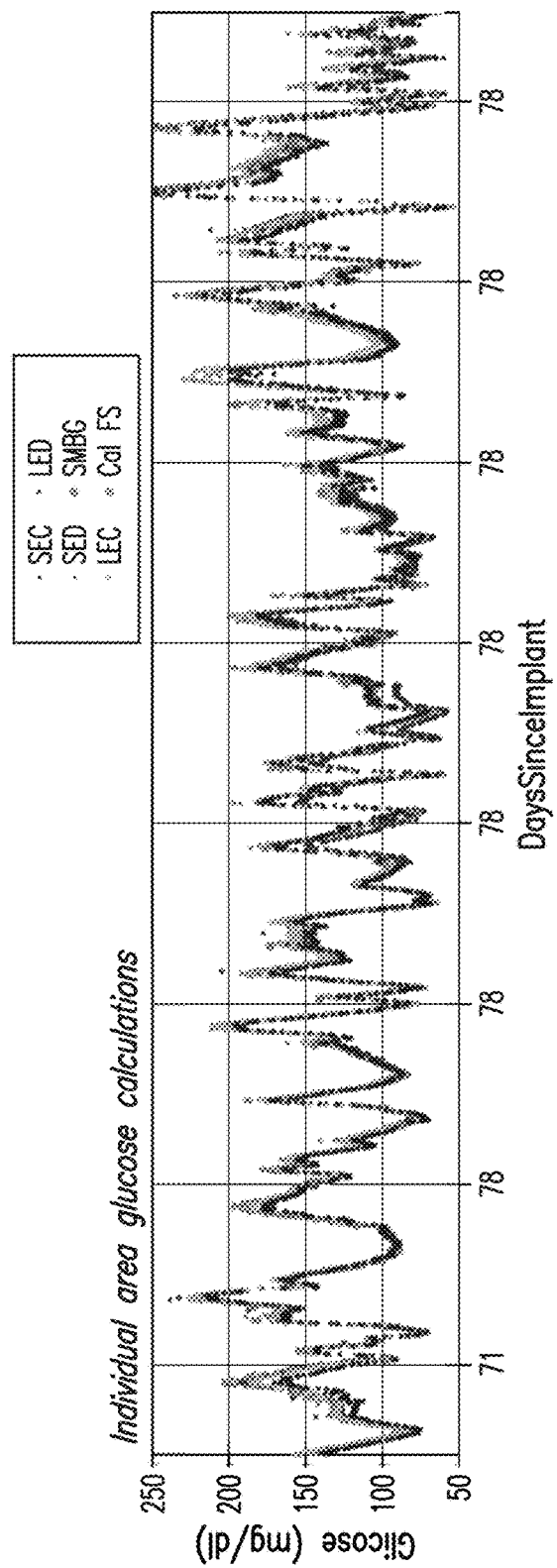
FIG. 26A shows individual glucose concentrations calculated from sensing areas of the analyte sensor 100 shown in FIG. 22 individually according to some aspects.
Figure 26B:
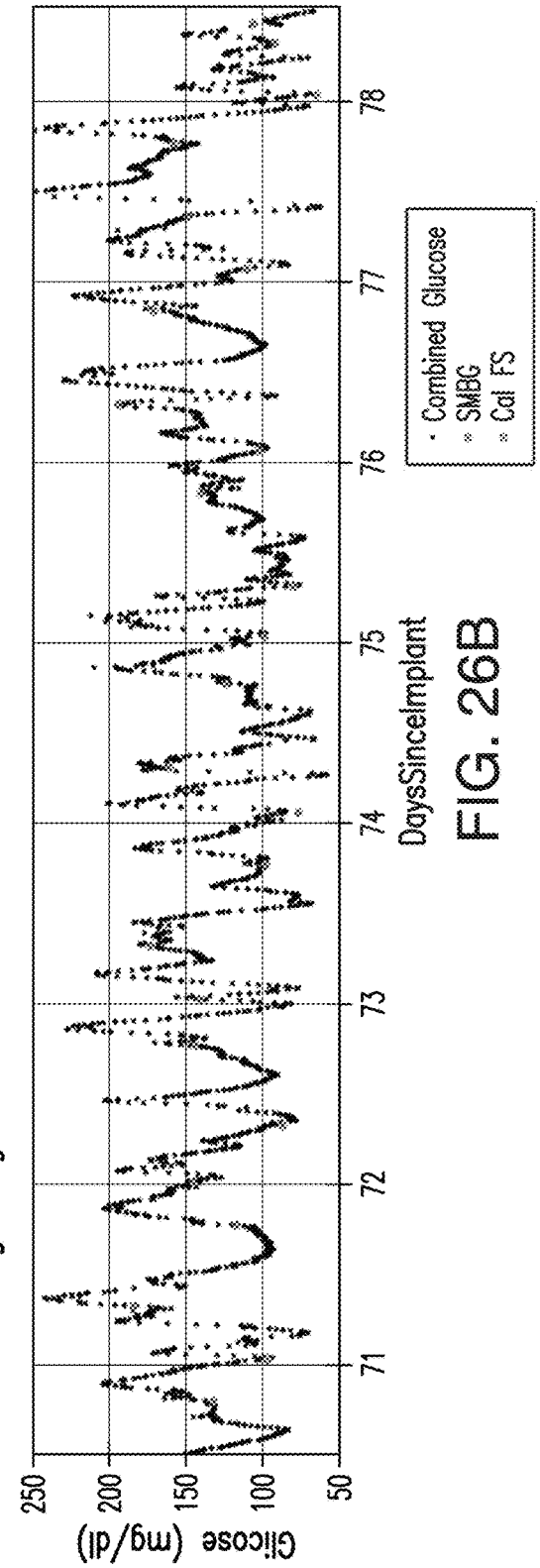
FIG. 26B shows combined glucose concentrations calculated based on a weighted average of the individual glucose concentrations according to some aspects.

In some aspects, the analyte sensor 100 shown in FIG. 22 may combine an interferent indicator 209 used to measure oxidation and redundant sensing areas 2202a-2202d to obtain analyte values using weighted averaging. In some aspects, the analyte monitoring system 50 (e.g., the transceiver 101 of the analyte monitoring system 50) may integrate the oxidation measurements and the analyte measurements into an analyte calculation model that allows for reduced calibration frequency (e.g., one calibration per week after day 14). In some aspects, the analyte monitoring system 50 may selectively utilize information (e.g., measurements) from the sensing areas 2202 from the multi-analyte (e.g., glucose and oxidation), multi-site array to calculate glucose values. In a non-limiting example, FIG. 26A shows individual glucose concentrations calculated from the sensing areas 2202a-2202d of the analyte sensor 100 shown in FIG. 22 individually (e.g., based on measurements of one or more of the first and second excitation lights 329 and 330 and the first and second emission lights 331 and 332 from the sensor areas 2202 individually), and FIG. 26B shows combined glucose concentrations calculated based on a weighted average of the individual glucose concentrations. In some aspects, the sensing areas 2202a and 2202c may be long end distal (LED) and long end central (LEC) sensing areas of the analyte sensor 100, respectively, and the sensing areas 2202b and 2202d may be short end central (SEC) and short end distal (SED) sensing areas of the analyte sensor, respectively.

In a non-limiting example, in the 10 subject feasibility study, as shown in the table below, the analyte monitoring system 50 with the analyte sensor 100 shown in FIG. 22 had an overall MARD of 9.2% at 90-days and 9.3% at 180-days, with one calibration per week using finger stick glucose measurements as a reference.

| Use Duration | MARD | 15/15 | 20/20 | 40/40 |
| --- | --- | --- | --- | --- |
| 3 months | 9.2 | 84.1 | 91.7 | 99.1 |
| 6 months | 9.3 | 84 | 91.7 | 99 |

In a non-limiting example, these studies show that the multiple sensing channels of the analyte sensor 100 shown in FIG. 22 enable accurate measurement of glucose, as well as assessment of oxidation of the indicator element 106. By detecting these multiple analytes (e.g., glucose and oxidation), accuracy can be maintained for up to 365 days with a significant reduction in calibration to one time per week. Future studies are planned to assess the performance of the analyte monitoring system 50 including the analyte sensor 100 shown in FIG. 22.

Aspects of the present invention have been fully described above with reference to the drawing figures. Although the invention has been described based upon these preferred aspects, it would be apparent to those of skill in the art that certain modifications, variations, and alternative constructions could be made to the described aspects within the spirit and scope of the invention. For example, although the aspects of the invention in which the analyte indicator 207 and interferent indicator 209 are distributed throughout the same indicator element 106, this is not required. In some alternative aspects, the analyte sensor 100 may include a first indicator element that includes the analyte indicator 207 and a second indicator element that includes the interferent indicator 209. In these alternative aspects, the analyte indicator 207 and the interferent indicator 209 may be spatially separated from one another.

What is claimed is:

1. An analyte monitoring system comprising:
   an analyte indicator having a first detectable property that varies in accordance with at least (i) an amount or concentration of an analyte in a medium and (ii) an effect on the analyte indicator; and
   an interferent indicator having an absorption that varies in accordance with the effect on the analyte indicator;
   sensor elements configured to generate (i) an analyte measurement based on the first detectable property of the analyte indicator and (ii) a reference measurement based on at least the absorption of the interferent indicator;
   a controller configured to:
      (i) calculate the effect on the analyte indicator based at least on the reference measurement;
      (ii) adjust a conversion function based on at least the calculated effect on the analyte indicator; and (iii) calculate an analyte level using the adjusted conversion function and the analyte measurement.

2. The analyte monitoring system of claim 1, wherein the effect on the analyte indicator is degradation of the analyte indicator.

3. The analyte monitoring system of claim 1, further comprising an indicator element that comprises the analyte indicator and the interferent indicator, wherein the analyte indicator comprises analyte indicator molecules distributed throughout the indicator element, and the interferent indicator comprises interferent indicator molecules distributed throughout the indicator element.

4. The analyte monitoring system of claim 1, wherein the sensor elements comprise:
a first light source configured to emit first excitation light to the analyte indicator; and
a signal photodetector configured to receive first emission light emitted by the analyte indicator and output the analyte measurement, wherein the analyte measurement is indicative of an amount of the first emission light received by the signal photodetector.

5. The analyte monitoring system of claim 4, wherein the sensor elements further comprise a second light source configured to emit second excitation light to the interferent indicator.

6. The analyte monitoring system of claim 5, wherein the signal photodetector is further configured to receive an amount of the second excitation light and output the reference measurement, the reference measurement is indicative of the amount of the received second excitation light, and the amount of the received second excitation light is indicative of the absorption of the interferent indicator.

7. The analyte monitoring system of claim 5, wherein the sensor elements further comprise a reference photodetector configured to receive an amount of the second excitation light and output the reference measurement, the reference measurement is indicative of the amount of the received second excitation light, and the amount of the received second excitation light is indicative of the absorption of the interferent indicator.

8. The analyte monitoring system of claim 5, wherein the sensor elements further comprise an interferent photodetector configured to receive second emission light emitted by the interferent indicator and output an interferent measurement indicative of an amount of the second emission light received by the interferent photodetector.

9. The analyte monitoring system of claim 8, wherein the second emission light varies in accordance with the effect on the analyte indicator.

10. The analyte monitoring system of claim 8, wherein the sensor elements comprise a first reference photodetector configured to receive an amount of the first excitation light and output a first reference measurement indicative of the amount of the received first excitation light.

11. The analyte monitoring system of claim 8, wherein the second emission light emitted by the interferent indicator does not vary in accordance with the amount or concentration of the analyte in the medium.

12. The analyte monitoring system of claim 8, wherein the processor is configured to calculate the effect on the analyte indicator based at least on the reference measurement and the interferent measurement.

13. The analyte monitoring system of claim 8, wherein the processor is configured to calculate the effect on the analyte indicator based at least on a ratio of the interferent measurement and the reference measurement.

14. The analyte monitoring system of claim 1, wherein the absorption of the interferent indicator does not vary in accordance with the amount or concentration of the analyte in the medium.

15. The analyte monitoring system of claim 1, wherein the processor is further configured to calculate an amount of blood in the medium.

16. The analyte monitoring system of claim 15, wherein the processor is configured to adjust the conversion function based on at least the calculated effect on the analyte indicator and the calculated amount of blood in the medium.

17. The analyte monitoring system of claim 15, wherein the reference measurement is a second reference measurement, and the sensor elements comprise:
a first light source configured to emit first excitation light to the analyte indicator;
a second light source configured to emit second excitation light to the interferent indicator;
a first reference photodetector configured to receive an amount of the first excitation light and output a first reference measurement indicative of the amount of the received first excitation light; and
a signal photodetector configured to (i) receive first emission light emitted by the analyte indicator and output the analyte measurement and (ii) receive an amount of the second excitation light and output the second reference measurement, wherein the analyte measurement is indicative of the amount of the received first emission light, and the second reference measurement is indicative of the amount of the received second excitation light.

18. The analyte monitoring system of claim 17, wherein the processor is configured to calculate the amount of blood in the medium based on at least the first and second reference measurements.

19. The analyte monitoring system of claim 17, wherein the processor is configured to calculate the amount of blood in the medium based on at least a ratio of the first and second reference measurements.

20. The analyte monitoring system of claim 15, wherein the reference measurement is a second reference measurement, and the sensor elements comprise:
a first light source configured to emit first excitation light to the analyte indicator;
a second light source configured to emit second excitation light to the interferent indicator;
a first reference photodetector configured to receive an amount of the first excitation light and output a first reference measurement indicative of the amount of the received first excitation light;
a signal photodetector configured to receive first emission light emitted by the analyte indicator and output the analyte measurement, wherein the analyte measurement is indicative of an amount of the received first emission light; and
a second reference photodetector configured to receive an amount of the second excitation light and output the second reference measurement, wherein the second reference measurement is indicative of the amount of the received second excitation light.

21. The analyte monitoring system of claim 15, wherein the sensor elements comprise an interferent photodetector configured to receive emission light emitted by the interferent indicator and output an interferent measurement indicative of an amount of the emission light received by the interferent photodetector, and the processor is configured to calculate the amount of blood in the medium based on at least the interferent measurement.

22. The analyte monitoring system of claim 1, wherein the interferent indicator has a second detectable property that varies in accordance with the effect on the analyte indicator, the sensor elements are further configured to generate an interferent measurement based on the second detectable property of the analyte indicator, and the processor is configured to calculate the effect on the analyte indicator based at least on the reference measurement and the interferent measurement.

23. The analyte monitoring system of claim 22, wherein the processor is configured to calculate the effect on the analyte indicator at least based on a ratio of the interferent measurement and the reference measurement.

24. A method comprising:
using an analyte indicator to generate an analyte measurement indicative of an amount or concentration of an analyte in a medium, wherein the analyte measurement varies in accordance with at least an effect on the analyte indicator;
using an interferent indicator to generate a reference measurement indicative of an absorption of the interferent indicator, wherein the absorption varies in accordance with the effect on the analyte indicator;
calculating the effect on the analyte indicator based at least on the reference measurement;
adjusting a conversion function based on at least the calculated effect on the analyte indicator; and
calculating an analyte level using the adjusted conversion function and the analyte measurement.

25. The method of claim 24, wherein the effect on the analyte indicator is degradation of the analyte indicator.

26. The method of claim 24, wherein using the analyte indicator to generate the analyte measurement comprises:
emitting first excitation light to the analyte indicator; and
using a signal photodetector configured to receive first emission light emitted by the analyte indicator and output the analyte measurement, wherein the analyte measurement is indicative of an amount of the first emission light received by the signal photodetector.

27. The method of claim 26, wherein using the interferent indicator to generate the reference measurement comprises emitting second excitation light to the interferent indicator.

28. The method of claim 27, wherein using the interferent indicator to generate the reference measurement further comprises using the signal photodetector to receive an amount of the second excitation light and output the reference measurement, the reference measurement is indicative of the amount of the received second excitation light, and the amount of the received second excitation light is indicative of the absorption of the interferent indicator.

29. The method of claim 27, wherein using the interferent indicator to generate the reference measurement further comprises using a reference photodetector to receive an amount of the second excitation light and output the reference measurement, the reference measurement is indicative of the amount of the received second excitation light, and the amount of the received second excitation light is indicative of the absorption of the interferent indicator.

30. The method of claim 27, further comprising using an interferent photodetector to receive second emission light emitted by the interferent indicator and output an interferent measurement indicative of an amount of the second emission light received by the interferent photodetector.

31. The method of claim 30, wherein the second emission light varies in accordance with the effect on the analyte indicator.

32. The method of claim 30, further comprising using a first reference photodetector to receive an amount of the first excitation light and output a first reference measurement indicative of the amount of the received first excitation light.

33. The method of claim 30, wherein the effect on the analyte indicator is calculated based at least on the reference measurement and the interferent measurement.

34. The method of claim 30, wherein the effect on the analyte indicator is calculated based at least on a ratio of the interferent measurement and the reference measurement.

35. The method of claim 24, further comprising calculating an amount of blood in the medium.

36. The method of claim 35, wherein the conversion function is adjusted based on at least the calculated effect on the analyte indicator and the calculated amount of blood in the medium.

37. The method of claim 35, wherein the reference measurement is a second reference measurement;
wherein using the analyte indicator to generate the analyte measurement comprises:
emitting first excitation light to the analyte indicator;
using a first reference photodetector to receive an amount of the first excitation light and output a first reference measurement indicative of the amount of the received first excitation light; and
using a signal photodetector to receive first emission light emitted by the analyte indicator and output the analyte measurement, wherein the analyte measurement is indicative of the amount of the received first emission light;
wherein using the interferent indicator to generate the reference measurement comprises:
emitting second excitation light to the interferent indicator; and
using the signal photodetector to receive an amount of the second excitation light and output the second reference measurement, wherein the second reference measurement is indicative of the amount of the received second excitation light; and
wherein the amount of blood in the medium is calculated based on at least the first and second reference measurements.

38. The method of claim 37, wherein the amount of blood in the medium is calculated based on at least a ratio of the first and second reference measurements.

39. The method of claim 35, wherein the reference measurement is a second reference measurement;
wherein using the analyte indicator to generate the analyte measurement comprises:
emitting first excitation light to the analyte indicator;
using a first reference photodetector to receive an amount of the first excitation light and output a first reference measurement indicative of the amount of the received first excitation light; and
using a signal photodetector to receive first emission light emitted by the analyte indicator and output the analyte measurement, wherein the analyte measurement is indicative of the amount of the received first emission light;
wherein using the interferent indicator to generate the reference measurement comprises:
emitting second excitation light to the interferent indicator; and using a second reference photodetector to receive an amount of the second excitation light and output the second reference measurement, wherein the second reference measurement is indicative of the amount of the received second excitation light; and wherein the amount of blood in the medium is calculated based on at least the first and second reference measurements.

40. The method of claim 35, further comprising using an interferent photodetector to receive emission light emitted by the interferent indicator and output an interferent measurement indicative of an amount of the emission light received by the interferent photodetector, and the amount of blood in the medium is calculated based on at least the interferent measurement.

* * * * *